(12) United States Patent
Wischik et al.

(10) Patent No.: US 12,263,175 B2
(45) Date of Patent: *Apr. 1, 2025

(54) OPTIMISED DOSAGE OF DIAMINOPHENOTHIAZINES IN POPULATIONS

(71) Applicant: WisTa Laboratories Ltd., Singapore (SG)

(72) Inventors: Claude Michel Wischik, Aberdeen (GB); Bjorn Olaf Schelter, Aberdeen (GB); Helen Christine Shiells, Aberdeen (GB)

(73) Assignee: WisTa Laboratories Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/961,961

(22) Filed: Oct. 7, 2022

(65) Prior Publication Data

US 2023/0115931 A1    Apr. 13, 2023

Related U.S. Application Data

(63) Continuation of application No. 17/262,902, filed as application No. PCT/EP2019/069428 on Jul. 18, 2019.

(30) Foreign Application Priority Data

Jul. 26, 2018  (GB) ..................... 1812193
Jul. 1, 2019   (GB) ..................... 1909458

(51) Int. Cl.
| | |
|---|---|
| *A61K 31/5415* | (2006.01) |
| *A23L 33/00* | (2016.01) |
| *A23L 33/105* | (2016.01) |
| *A23L 33/15* | (2016.01) |
| *A23L 33/175* | (2016.01) |
| *A23L 33/29* | (2016.01) |
| *A61K 9/00* | (2006.01) |
| *A61K 9/20* | (2006.01) |
| *A61K 9/48* | (2006.01) |
| *A61K 31/13* | (2006.01) |
| *A61P 25/28* | (2006.01) |

(52) U.S. Cl.
CPC ........ *A61K 31/5415* (2013.01); *A23L 33/105* (2016.08); *A23L 33/15* (2016.08); *A23L 33/175* (2016.08); *A23L 33/29* (2016.08); *A23L 33/30* (2016.08); *A61K 9/0053* (2013.01); *A61K 9/20* (2013.01); *A61K 9/48* (2013.01); *A61K 31/13* (2013.01); *A61P 25/28* (2018.01)

(58) Field of Classification Search
CPC .... A61P 25/28; A61K 31/5415; A61K 9/0053
See application file for complete search history.

(56) References Cited

U.S. PATENT DOCUMENTS

| | | | |
|---|---|---|---|
| 9,283,230 B2 * | 3/2016 | Clunas ................ | A61P 25/00 |
| 10,525,061 B2 | 1/2020 | Wischik et al. | |
| 10,537,578 B2 | 1/2020 | Storey et al. | |
| 10,842,796 B2 | 11/2020 | Wischik et al. | |
| 10,864,216 B2 | 12/2020 | Marshall et al. | |
| 10,968,174 B2 | 4/2021 | Sinclair et al. | |
| 11,045,477 B2 | 6/2021 | Wischik et al. | |
| 11,065,256 B2 * | 7/2021 | Wischik ................ | A61P 21/00 |
| 11,116,772 B2 | 9/2021 | Storey et al. | |
| 11,180,464 B2 | 11/2021 | Storey et al. | |
| 11,344,558 B2 | 5/2022 | Wischik et al. | |
| 11,759,469 B2 | 9/2023 | Wischik et al. | |
| 2013/0184268 A1 | 7/2013 | Pahnke | |
| 2016/0051559 A1 | 2/2016 | Wischik et al. | |
| 2018/0078562 A1 | 3/2018 | Storey et al. | |
| 2018/0263999 A1 | 9/2018 | Wischik et al. | |
| 2019/0046537 A1 | 2/2019 | Marshall et al. | |
| 2019/0151329 A1 | 5/2019 | Wischik et al. | |
| 2019/0192530 A1 | 6/2019 | Wischik et al. | |
| 2020/0016165 A1 | 1/2020 | Wischik et al. | |
| 2020/0115335 A1 | 4/2020 | Sinclair et al. | |
| 2020/0246350 A1 | 8/2020 | Storey et al. | |
| 2020/0261465 A1 | 8/2020 | Wischik et al. | |
| 2020/0268767 A1 | 8/2020 | Storey et al. | |
| 2021/0236509 A1 | 8/2021 | Schelter et al. | |

(Continued)

FOREIGN PATENT DOCUMENTS

| | | |
|---|---|---|
| WO | WO 96/30766 A1 | 10/1996 |
| WO | WO 02/055720 A2 | 7/2002 |

(Continued)

OTHER PUBLICATIONS

International Search Report and Written Opinion for Application No. PCT/EP2019/069428, mailed Nov. 7, 2019.
International Preliminary Report on Patentability for Application No. PCT/EP2019/069428, mailed Feb. 4, 2021.
Alda et al., Methylene blue treatment for residual symptoms of bipolar disorder: randomised crossover study. Br J Psychiatry. Jan. 2017;210(1):54-60. doi: 10.1192/bjp.bp.115.173930. Epub Jun. 9, 2016.
Auchter et al., Methylene Blue Preserves Cytochrome Oxidase Activity and Prevents Neurodegeneration and Memory Impairment in Rats With Chronic Cerebral Hypoperfusion. Front Cell Neurosci. May 20, 2020;14:130. doi: 10.3389/fncel.2020.00130. eCollection 2020.

(Continued)

*Primary Examiner* — Michael B. Pallay
(74) *Attorney, Agent, or Firm* — Wolf, Greenfield & Sacks, P.C.

(57) ABSTRACT

The invention provides novel dosing regimens for Leuco-Methylthioninium (LMT) compounds which maximise the proportion of subjects in which the MT concentration will exceed concentrations in which therapeutic efficacy in relation to treatment of neurodegenerative disorders such as Alzheimer's disease and rontotemporal dementias can be achieved, while maintaining a desirable clinical profile. Also provided are LMT-containing dosage units and other compositions.

20 Claims, 25 Drawing Sheets

(56) References Cited

U.S. PATENT DOCUMENTS

Figure 1:
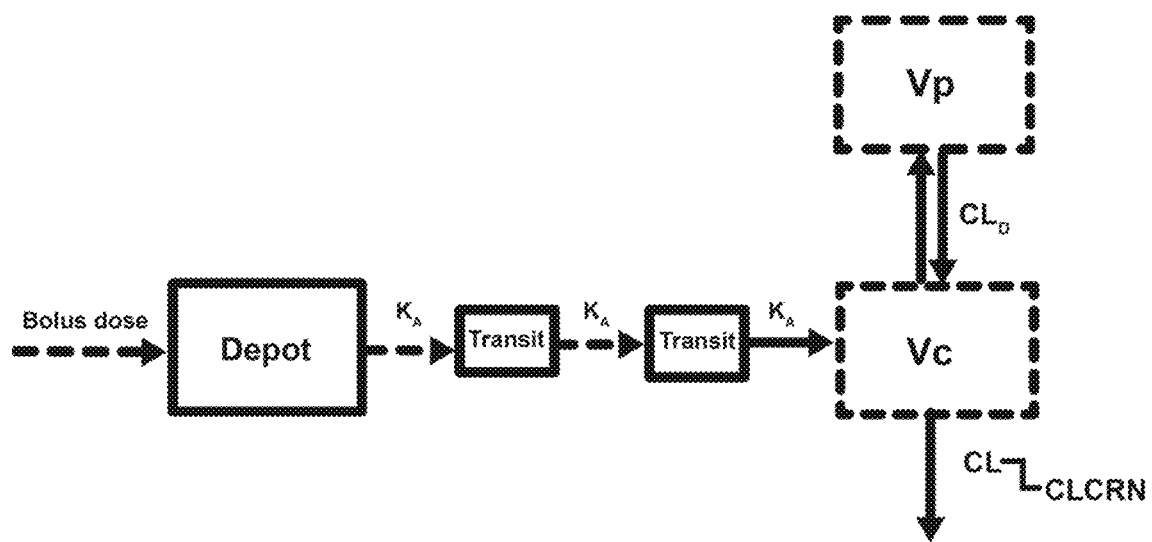

| | | |
|---|---|---|
| 2021/0322435 A1 | 10/2021 | Wischik et al. |
| 2022/0008431 A1 | 1/2022 | Wischik et al. |
| 2022/0098161 A1 | 3/2022 | Marshall et al. |
| 2022/0152038 A1 | 5/2022 | Wischik et al. |
| 2022/0330594 A1 | 10/2022 | Riedel et al. |
| 2022/0370470 A1 | 11/2022 | Riedel et al. |
| 2023/0031369 A1 | 2/2023 | Riedel et al. |
| 2023/0165877 A1 | 6/2023 | Wischik et al. |
| 2023/0346794 A1 | 11/2023 | Wischik et al. |

FOREIGN PATENT DOCUMENTS

| | | | |
|---|---|---|---|
| WO | WO 2003/101458 A1 | 12/2003 | |
| WO | WO 2006/032879 A2 | 3/2006 | |
| WO | WO 2007/110627 A2 | 10/2007 | |
| WO | WO 2007/110629 A1 | 10/2007 | |
| WO | WO 2007/110630 A1 | 10/2007 | |
| WO | WO 2008/155533 A2 | 12/2008 | |
| WO | WO 2009/044127 A1 | 4/2009 | |
| WO | WO 2009/060191 A2 | 5/2009 | |
| WO | WO-2010104394 A1 * | 9/2010 | ........... A23L 1/3004 |
| WO | WO 2011/036561 A2 | 3/2011 | |
| WO | WO 2012/107706 A1 | 8/2012 | |
| WO | WO 2018/019823 A1 | 2/2018 | |
| WO | WO 2018/041739 A1 | 3/2018 | |
| WO | WO 2020/020751 A1 | 1/2020 | |

OTHER PUBLICATIONS

Bruchey et al., Behavioral, Physiological and Biochemical Hormetic Responses to the Autoxidizable Dye Methylene Blue. Am J Pharmacol Toxicol. Jan. 1, 2008;3(1):72-79. doi: 10.3844/ajptsp.2008.72.79.
Gauthier et al., Efficacy and safety of tau-aggregation inhibitor therapy in patients with mild or moderate Alzheimer's disease: a randomised, controlled, double-blind, parallel-arm, phase 3 trial. Lancet. Dec. 10, 2016;388(10062):2873-2884. doi: 10.1016/S0140-6736(16)31275-2. Epub Nov. 16, 2016.
Gonzalez-Lima et al., Protection against neurodegeneration with low-dose methylene blue and near-infrared light. Front Cell Neurosci. May 12, 2015;9:179. doi: 10.3389/fncel.2015.00179. eCollection 2015.
Naylor et al., A Two-Year Double-Blind Crossover Trial of the Prophylactic Effect of Methylene Blue in Manic-Depressive Psychosis. Biol Psychiatry. Aug. 1986;21(10):915-20. doi: 10.1016/0006-3223(86)90265-9.
Naylor et al., A Controlled Trial of Methylene Blue in Severe Depressive Illness. Biol Psychiatry. May 1987;22(5):657-9. doi: 10.1016/0006-3223(87)90194-6.
Panza et al., Tau-Centric Targets and Drugs in Clinical Development for the Treatment of Alzheimer's Disease. Biomed Res Int. 2016;2016:3245935. doi: 10.1155/2016/3245935. Epub Jun. 26, 2016.
Rodriguez et al., Multimodal Randomized Functional MR Imaging of the Effects of Methylene Blue in the Human Brain. Radiology. Nov. 2016;281(2):516-526. doi: 10.1148/radiol.2016152893. Epub Jun. 28, 2016.
Schelter et al., Concentration-Dependent Activity of Hydromethylthionine on Cognitive Decline and Brain Atrophy in Mild to Moderate Alzheimer's Disease. J Alzheimers Dis. 2019;72(3):931-946. doi: 10.3233/JAD-190772.
Schelter et al., Meta-analysis of two tau aggregation inhibitor Phase 3 trials in mild Alzheimer's disease with low dose hydromethylthionine. JPAD. 2018; 5(1):S66.
Shiells et al., Concentration-Dependent Activity of Hydromethylthionine on Clinical Decline and Brain Atrophy in a Randomized Controlled Trial in Behavioral Variant Frontotemporal Dementia. J Alzheimers Dis. 2020;75(2):501-519. doi: 10.3233/JAD-191173.
Telch et al., Effects of post-session administration of methylene blue on fear extinction and contextual memory in adults with claustrophobia. Am J Psychiatry. Oct. 2014;171(10):1091-8. doi: 10.1176/appi.ajp.2014.13101407.
Wilcock et al., Potential of Low Dose Leuco-Methylthioninium Bis(Hydromethanesulphonate) (LMTM) Monotherapy for Treatment of Mild Alzheimer's Disease: Cohort Analysis as Modified Primary Outcome in a Phase III Clinical Trial. J Alzheimers Dis. 2018;61(1):435-457. doi: 10.3233/JAD-170560.
International Search Report and Written Opinion for Application No. PCT/EP2017/068749, mailed May 10, 2017.
International Preliminary Report on Patentability for Application No. PCT/EP2017/068749, mailed Feb. 7, 2019.
International Search Report and Written Opinion for Application No. PCT/EP2017/071437, mailed Nov. 24, 2017.
International Preliminary Report on Patentability for Application No. PCT/EP2017/071437, mailed Mar. 14, 2019.
International Search Report and Written Opinion for Application No. PCT/EP2020/068422, mailed Sep. 28, 2020.
International Preliminary Report on Patentability for Application No. PCT/EP2020/068422, mailed Jan. 13, 2022.
Al-Hilaly et al., Cysteine-Independent Inhibition of Alzheimer's Disease-like Paired Helical Filament Assembly by Leuco-Methylthioninium (LMT). J Mol Biol. Oct. 19, 2018;430(21):4119-4131. doi: 10.1016/j.jmb.2018.08.010. Epub Aug. 16, 2018.
Atamna et al., Mitochondrial pharmacology: electron transport chain bypass as strategies to treat mitochondrial dysfunction. Biofactors. Mar.-Apr. 2012;38(2):158-66. doi: 10.1002/biof.197. Epub Mar. 15, 2012.
Baddeley et al., Complex disposition of methylthioninium redox forms determines efficacy in tau aggregation inhibitor therapy for Alzheimer's disease. J Pharmacol Exp Ther. Jan. 2015;352(1):110-8. doi: 10.1124/jpet.114.219352. Epub Oct. 15, 2014.
Congdon et al., Tau-targeting therapies for Alzheimer disease. Nat Rev Neurol. Jul. 2018;14(7):399-415. doi: 10.1038/s41582-018-0013-z.
Douaud et al., Preventing Alzheimer's disease-related gray matter atrophy by B-vitamin treatment. Proc Natl Acad Sci U S A. Jun. 4, 2013;110(23):9523-8. doi: 10.1073/pnas.1301816110. Epub May 20, 2013.
Feldman et al., A phase 3 trial of the tau and TDP-43 aggregation inhibitor, leuco-methylthioninium-bis (hydromethanesulfonate) (LMTM), for behavioural variant frontotemporal dementia (bvFTD). J Neurochemistry. Jul. 18, 2016;138(1):255.
Harrington et al., Cellular models of aggregation-dependent template-directed proteolysis to characterize tau aggregation inhibitors for treatment of Alzheimer's disease. J Biol Chem. Apr. 24, 2015;290(17):10862-75. doi: 10.1074/jbc.M114.616029. Epub Mar. 10, 2015.
Jaber et al., Addressing Alzheimer's Disease (AD) Neuropathology Using Anti-microRNA (AM) Strategies. Mol Neurobiol. Dec. 2019;56(12):8101-8108. doi: 10.1007/s12035-019-1632-0. Epub Jun. 10, 2019.
Kazim et al., Neural Regeneration as a Disease-Modifying Therapeutic Strategy for Alzheimer's Disease. Chapter 2 in: Neuroprotection in Alzheimer's Disease. 2017; 3-29. https://doi.org/10.1016/B978-0-12-803690-7.00002-8.
McGleenon et al., Acetylcholinesterase inhibitors in Alzheimer's disease. Br J Clin Pharmacol. 1999;48(4):471-480. doi: 10.1046/j.1365-2125.1999.00026.x.
Mecocci et al., Nutraceuticals in cognitive impairment and Alzheimer's disease. Front Pharmacol. Jun. 23, 2014;5:147. doi: 10.3389/fphar.2014.00147. eCollection 2014.
Melis et al., Different pathways of molecular pathophysiology underlie cognitive and motor tauopathy phenotypes in transgenic models for Alzheimer's disease and frontotemporal lobar degeneration. Cell Mol Life Sci. Jun. 2015;72(11):2199-222. doi: 10.1007/s00018-014-1804-z. Epub Dec. 19, 2014.
Melis et al., Effects of oxidized and reduced forms of methylthioninium in two transgenic mouse tauopathy models. Behav Pharmacol. Jun. 2015;26(4):353-68. doi: 10.1097/FBP.0000000000000133.
Oz et al., Methylene blue and Alzheimer's disease. Biochem Pharmacol. Oct. 15, 2009;78(8):927-32. doi: 10.1016/j.bcp.2009.04.034. Epub May 9, 2009.
Panza et al., A critical appraisal of amyloid-β-targeting therapies for Alzheimer disease. Nat Rev Neurol. Feb. 2019;15(2):73-88. doi: 10.1038/s41582-018-0116-6.

(56) References Cited

OTHER PUBLICATIONS

Pappas, Statistical Analysis Plan—Randomized Double-Blind, Placebo-Controlled, Parallel-Griup, 18-Month Safety and Efficacy Study of Leuco-methylthioninium bis(hydromethanesulfonate) in Subjects with Mild Alzheimer's Disease. Version 2.0. TauRx Therapeutics Ltd. TRx-237-005. Jun. 20, 2016. 89 pages.

Pappas, Statistical Analysis Plan (Addendum)—Randomized Double-Blind, Placebo-Controlled, Parallel-Griup, 18-Month Safety and Efficacy Study of Leuco-methylthioninium bis(hydromethanesulfonate) in Subjects with Mild Alzheimer's Disease. Version 1.0. TauRx Therapeutics Ltd. TRx-237-005. Jul. 4, 2016. 4 pages.

Schirmer et al., "Lest we forget you—methylene blue . . . ". Neurobiol Aging. Dec. 2011;32(12):2325.e7-16. doi: 10.1016/j.neurobiolaging.2010.12.012. Epub Feb. 12, 2011.

Smith, B vitamins can slow the disease process in early Alzheimer's disease. University of Oxford Impact case study (REF3b). Research Excellence Framework. 2014. 4 pages.

Stack et al., Methylene blue upregulates Nrf2/ARE genes and prevents tau-related neurotoxicity. Hum Mol Genet. Jul. 15, 2014;23(14):3716-32. doi: 10.1093/hmg/ddu080. Epub Feb. 20, 2014.

Tsai et al., Therapy and clinical trials in frontotemporal dementia: past, present, and future. J Neurochem. Aug. 2016;138 Suppl 1:211-21. doi:10.1111/jnc.13640. Epub Jun. 15, 2016.

Tsai et al., Treatment of frontotemporal dementia. Curr Treat Options Neurol. Nov. 2014;16(11):319. doi: 10.1007/s11940-014-0319-0.

Ustyugo et al., New Therapeutic Property of Dimebon as a Neuroprotective Agent. Curr Med Chem. 2018;25(39):5315-5326. doi: 10.2174/0929867323666160804122746.

Wilkinson, Alzheimer's drug 'halts' decline. BBC News Jul. 29, 2008. Accessed at http://news.bbc.co.uk/go/pr/fr/-/2/hi/health/7525115.stm on Sep. 21, 2017.

Wischik et al., Modeling prion-like processing of tau protein in Alzheimer's disease for pharmaceutical development. J Alzheimers Dis. 2018;62(3):1287-1303. doi: 10.3233/JAD-170727.

Wischik et al., Structural characterization of the core of the paired helical filament of Alzheimer disease. Proc Natl Acad Sci U S A. Jul. 1988;85(13):4884-8. doi: 10.1073/pnas.85.13.4884.

Yamashita et al., Methylene blue and dimebon inhibit aggregation of TDP-43 in cellular models. FEBS Lett. Jul. 21, 2009;583(14):2419-24. doi: 10.1016/j.febslet.2009.06.042. Epub Jun. 26, 2009.

Zhao et al., Methylene blue exerts a neuroprotective effect against traumatic brain injury by promoting autophagy and inhibiting microglial activation. Mol Med Rep. Jan. 2016;13(1):13-20. doi: 10.3892/mmr.2015.4551. Epub Nov. 11, 2015.

Kertesz, Behavioral and Psychological Symptoms and Frontotemporal Dementia (Pick's Disease). International Psychogeriatrics. 2000; 12(1): 183-187.

Albert et al., The diagnosis of mild cognitive impairment due to Alzheimer's disease: recommendations from the National Institute on Aging-Alzheimer's Association workgroups on diagnostic guidelines for Alzheimer's disease. Alzheimers Dement. Author manuscript; available in PMC Mar. 25, 2012. Published in final edited form as: Alzheimers Dement. May 2011; 7(3): 270-279. Published online Apr. 21, 2011. doi: 10.1016/j.jalz.2011.03.008.

Benedetti et al., Increasing uncertainty in CNS clinical trials: the role of placebo, nocebo, and Hawthorne effects. Lancet Neurol. Jun. 2016; 15(7):736-747. doi: 10.1016/S1474-4422(16)00066-1. Epub Apr. 19, 2016.

Boxer et al., The advantages of frontotemporal degeneration drug development (part 2 of frontotemporal degeneration: the next therapeutic frontier). Alzheimers Dement. Mar. 2013;9(2):189-98. doi: 10.1016/j.jalz.2012.03.003. Epub Oct. 10, 2012.

Cummings et al., The "rights" of precision drug development for Alzheimer's disease. Alzheimers Res Ther. Aug. 31, 2019;11(1):76. doi: 10.1186/s13195-019-0529-5.

Desmarais et al., Therapeutic trial design for frontotemporal dementia and related disorders. J Neurol Neurosurg Psychiatry. Apr. 2019;90(4):412-423. doi: 10.1136/jnnp-2018-318603. Epub Oct. 25, 2018.

Franzen et al., Diversity in Alzheimer's disease drug trials: The importance of eligibility criteria. Alzheimers Dement. Apr. 2022;18(4):810-823. doi: 10.1002/alz.12433. Epub Sep. 30, 2021.

Irwin, Tauopathies as clinicopathological entities. Parkinsonism Relat Disord. Jan. 2016;22 Suppl 1(01):S29-33. doi: 10.1016/j.parkreldis.2015.09.020. Epub Sep. 8, 2015.

Jutten et al., The Cognitive-Functional Composite is sensitive to clinical progression in early dementia: Longitudinal findings from the Catch-Cog study cohort. Alzheimers Dement (N Y). Apr. 17, 2020;6(1):e12020. doi: 10.1002/trc2.12020. eCollection 2020.

Jutten et al., Why a clinical trial is as good as its outcome measure: A framework for the selection and use of cognitive outcome measures for clinical trials of Alzheimer's disease. Alzheimers Dement. Feb. 2023;19(2):708-720. doi: 10.1002/alz.12773. Epub Sep. 10, 2022.

Kim et al., Data-driven prognostic features of cognitive trajectories in patients with amnestic mild cognitive impairments. Alzheimers Res Ther. Jan. 22, 2019;11(1):10. doi: 10.1186/s13195-018-0462-z.

No Author Listed, TauRx Pharmaceuticals Press Release. Sep. 4, 2016. 3 pages.

Panza et al., Development of disease-modifying drugs for frontotemporal dementia spectrum disorders. Nat Rev Neurol. Apr. 2020;16(4):213-228. doi: 10.1038/s41582-020-0330-x. Epub Mar. 23, 2020.

Schneider et al., Current Alzheimer's disease clinical trials: Methods and placebo outcomes. Alzheimers Dement. Sep. 2009;5(5):388-97. doi: 10.1016/j.jalz.2009.07.038.

Snyder et al., Assessing cognition and function in Alzheimer's disease clinical trials: Do we have the right tools? Alzheimers Dement. Nov. 2014;10(6):853-60. doi: 10.1016/j.jalz.2014.07.158. Epub Nov. 15, 2014.

Sperling et al., Toward defining the preclinical stages of Alzheimer's disease: recommendations from the National Institute on Aging-Alzheimer's Association workgroups on diagnostic guidelines for Alzheimer's disease. Alzheimers Dement. May 2011; 7(3): 280-292. Published online Apr. 21, 2011. doi: 10.1016/j.jalz.2011.03.003.

Tariot et al., The Alzheimer's Prevention Initiative Autosomal-Dominant Alzheimer's Disease Trial: A study of crenezumab versus placebo in preclinical PSEN1 E280A mutation carriers to evaluate efficacy and safety in the treatment of autosomal-dominant Alzheimer's disease, including a placebo-treated noncarrier cohort. Alzheimers Dement (N Y). Mar. 8, 2018:4:150-160. doi: 10.1016/j.trci.2018.02.002. eCollection 2018.

Vos et al., Prevalence and prognosis of Alzheimer's disease at the mild cognitive impairment stage. Brain. May 2015;138(Pt 5):1327-38. doi: 10.1093/brain/awv029. Epub Feb. 17, 2015.

Weintraub et al., Measuring cognition and function in the preclinical stage of Alzheimer's disease. Alzheimers Dement (N Y). Feb. 13, 2018:4:64-75. doi: 10.1016/j.trci.2018.01.003. eCollection 2018.

\* cited by examiner 8 mg/day ca. 200 mg/day

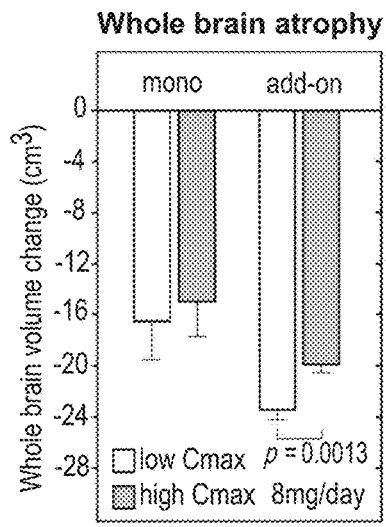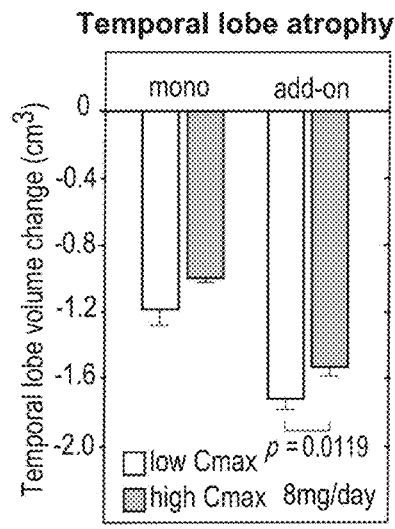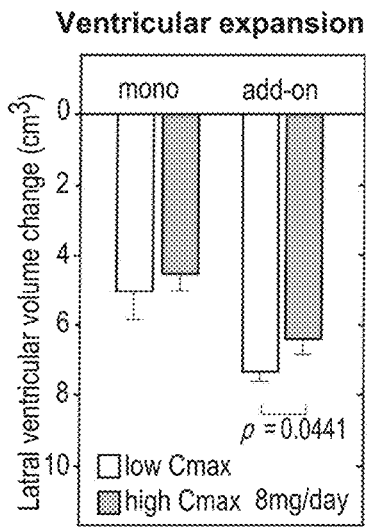
FIG. 4A Whole brain atrophy
FIG. 4B Temporal lobe atrophy
FIG. 4C Ventricular expansion
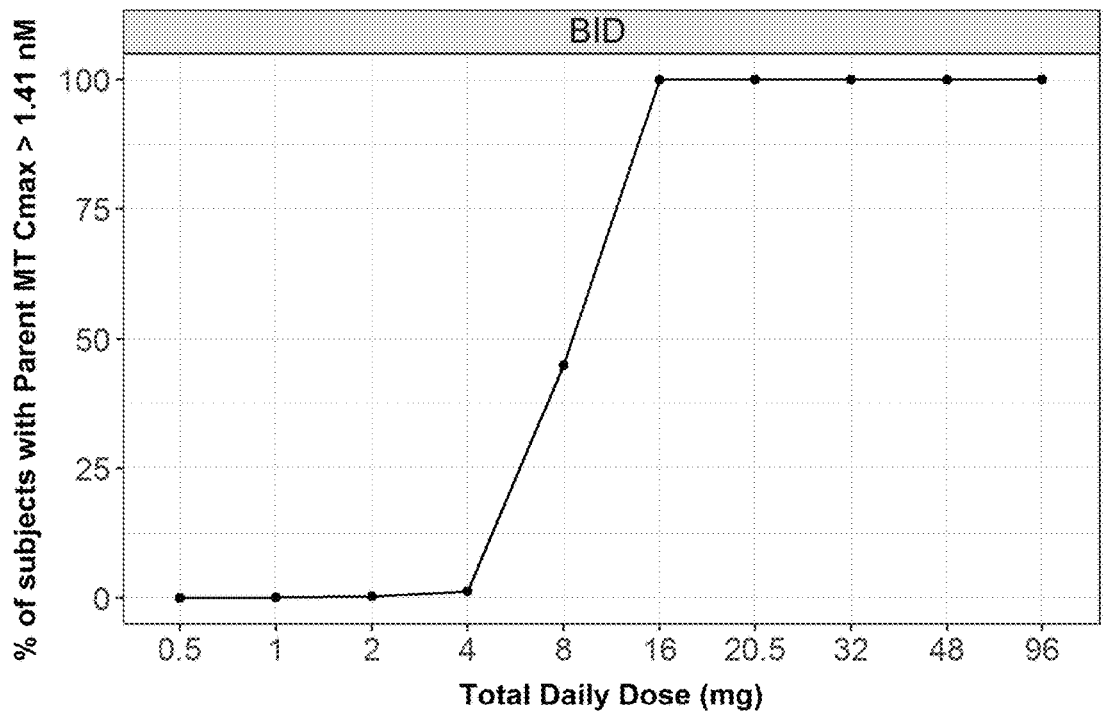
FIG. 5

8 mg/day 200 mg/day

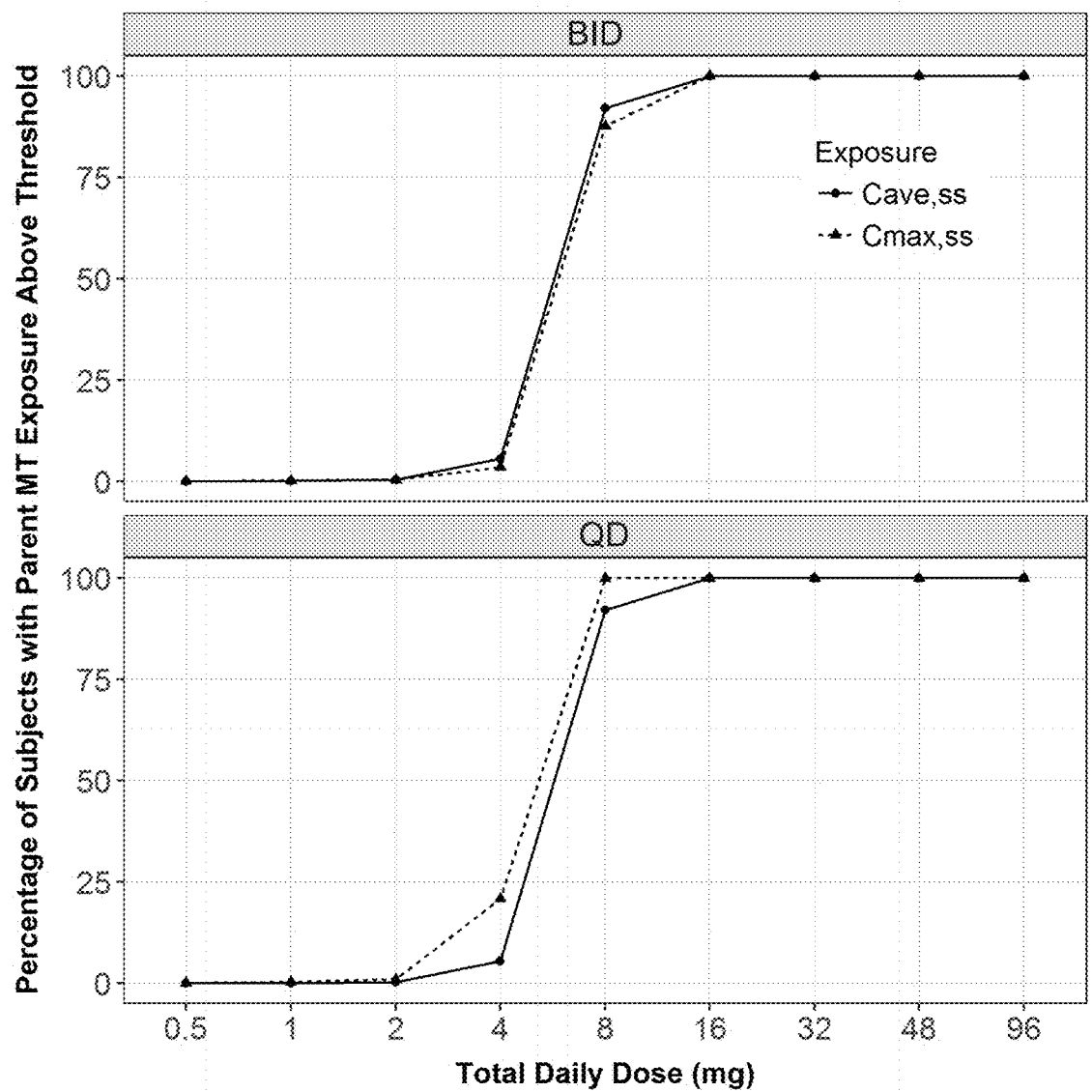

ADAS-cog$_{11}$

ADCS-ADL$_{23}$

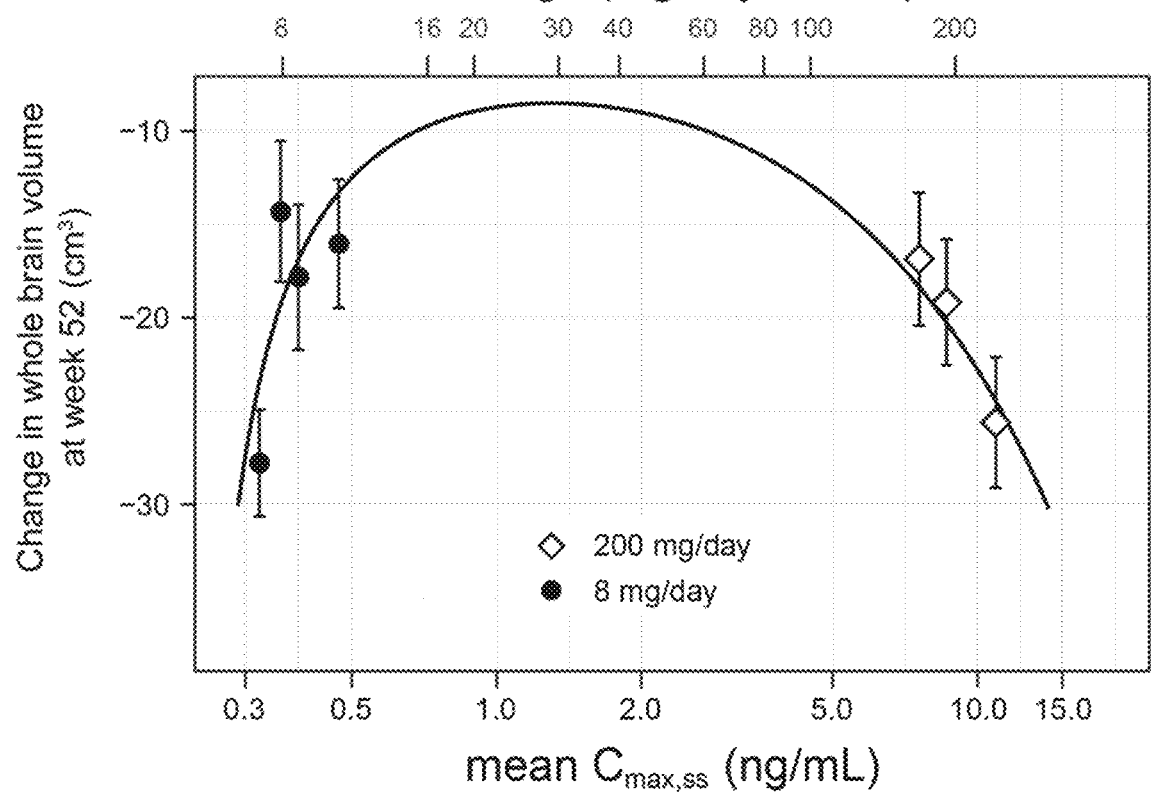

OPTIMISED DOSAGE OF DIAMINOPHENOTHIAZINES IN POPULATIONS

CROSS-REFERENCE TO RELATED APPLICATIONS

This Application is a Continuation application of U.S. application Ser. No. 17/262,902, filed Jan. 25, 2021, which is a National Stage filing under 35 U.S.C. 371 of International Patent Application Serial No. PCT/EP2019/069428, filed Jul. 18, 2019, which claims priority to Great Britain Application No. 1812193.9, filed Jul. 26, 2018, and Great Britain Application No. 1909458.0, filed Jul. 1, 2019. The contents of these applications are incorporated herein by reference in their entirety.

TECHNICAL FIELD

The present invention relates generally to optimised dosing regimens of diaminophenothiazines in the treatment or prophylaxis of neurodegenerative disorders, particularly within populations of individuals having different pharmacokinetic responses.

BACKGROUND ART

Aberrant protein aggregation is believed to be a proximal cause of numerous disease states, which may be manifested as neurodegeneration, clinical dementia, and other pathological symptoms.

In general, the aberrant protein aggregation is that which arises from an induced conformational polymerisation interaction, i.e., one in which a conformational change of the protein, or in a fragment thereof, gives rise to templated binding and aggregation of further (precursor) protein molecules in a self-propagating manner.

Once nucleation is initiated, an aggregation cascade may ensue which involves the induced conformational polymerisation of further protein molecules, leading to the formation of toxic product fragments in aggregates which are substantially resistant to further proteolysis.

For example certain conditions of dementia may be characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (see, e.g., Mukaetova-Ladinska et al., 2000).

Current approved treatments for Alzheimer's disease include acetylcholinesterase inhibitors (AChEIs) and the N-methyl-D-aspartate receptor antagonist memantine. These are symptomatic and do not address the underlying disease pathology. Therapies targeting the amyloid pathology have so far proved unsuccessful in late stage clinical trials (Geerts et al., 2013; Mullane and Williams, 2013). According to a recent Lancet Neurology Commission, "an effective treatment for AD is perhaps the greatest unmet medical need facing modern medicine", (Winblad et al., 2016) not least because the global economic cost of dementia is estimated to be $818 billion, or 0.65% of global gross domestic product (Alzheimer's Disease International, 2015).

NFTs (the pathology discovered by Alois Alzheimer, (Alzheimer, 1907)) are made up of paired helical filaments (PHFs), composed predominantly of a 12-kDa repeat-domain fragment of the microtubule-associated protein tau (Wischik et al., 1985; Wischik et al., 1988a,b). Numerous studies have confirmed a quantitative link for the spread of neurofibrillary tangle pathology and the quantity of aggregated tau with both the extent of clinical dementia and functional molecular imaging deficits in Alzheimer's disease (Arriagada et al., 1992; Brier et al., 2016; Giannakopoulos et al., 2003; Josephs et al., 2003; Maruyama et al., 2013). Since pathological aggregation of tau protein begins at least 20 years prior to any of the clinical manifestations (Braak and del Tredici, 2013), targeting this pathology offers a rational approach to both treatment and prevention of AD and related tau aggregation disorders (Huang and Mucke, 2012; Wischik et al., 2014; Wischik et al., 2010).

The tau fragment originally identified as an intrinsic structural constituent of the PHF core has prion-like properties in vitro in that it captures normal tau protein with very high affinity (Lai et al., 2016) and converts it to a proteolytically stable replicate of itself (Wischik et al., 1996; Harrington et al., 2015) in a process which is self-propagating and autocatalytic. Phosphorylation of tau is inhibitory to its aggregation (Lai et al., 2016) and is unlikely to drive the cascade (Mukaetova-Ladinska et al., 2000; Schneider et al., 1999; Wischik et al., 1995). Direct inhibition of tau aggregation represents a plausible point for therapeutic intervention.

Methylthioninium (MT) acts as a tau aggregation inhibitor (TAI) in vitro (Wischik et al., 1996; Harrington et al., 2015), dissolves PHFs from Alzheimer's disease brain tissue, (Wischik et al., 1996) and reduces tau pathology and associated behavioural deficits in transgenic mouse tau models at brain concentrations consistent with human oral dosing (Melis et al., 2015; Baddeley et al., 2015).

MT has also been shown to inhibit other disease-associated protein aggregation (see e.g. WO2007/110629 and references therein).

MT is a redox molecule and, depending on environmental conditions (e.g., pH, oxygen, reducing agents), exists in equilibrium between a reduced [leucomethylthioninium (LMT)] and oxidized form ($MT^+$).

WO96/30766 describes such MT-containing compounds for use in the treatment and prophylaxis of various diseases, including AD and Lewy Body Disease. One example compound was methylthioninium chloride ("MTC") commonly known as methylene blue, which is the chloride salt of the oxidized form of methylthioninium (MT) i.e. $MT^+$.

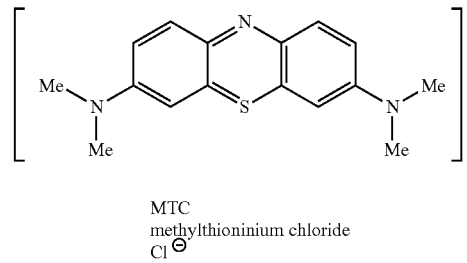

MTC
methylthioninium chloride
$Cl^{\ominus}$

WO96/30766 describes, in the case of oral administration, a daily dosage of about 50 mg to about 700 mg, preferably about 150 mg to about 300 mg, divided in preferably 1-3 unit doses.

WO2007/110630 discloses certain specific diaminophenothiazine compounds related to MTC, including (so-called) ETC, DEMTC, DMETC, DEETC, MTZ, ETZ, MTI, MTILHI, ETI, ETLHI, MTN, and ETN, which are useful as drugs, for example in the treatment of Alzheimer's disease and other diseases such as Frontotemporal dementia (FTD).

WO2007/110630 describes dosage units comprising 20 to 300 mg of 3,7-diaminophenothiazine (DAPTZ) compounds described therein e.g. 30 to 200 mg, for example 30 mg, 60 mg, 100 mg, 150 mg, 200 mg. A suitable dose of the DAPTZ compound is suggested in the range of about 100 ng to about 25 mg (more typically about 1 µg to about 10 mg) per kilogram body weight of the subject per day e.g. 100 mg, 3 times daily, 150 mg, 2 times daily, 200 mg, 2 times daily. A dosage of 50 mg 3 or 4 times daily is also discussed.

A preliminary pharmacokinetic model for methylene blue, based on studies of urinary excretion data sets in humans, dogs and rats, was proposed by DiSanto and Wagner, J Pharm Sci 1972, 61:1086-1090 and 1972, 61:1090-1094 and Moody et al., Biol Psych 1989, 26: 847-858.

Peter et aL. (2000) Eur J Clin Pharmacol 56: 247-250 provided a model which integrated blood level data, which contradicted the earlier data from DiSanto and Wagner as regards terminal elimination half-life.

May et al. (Am J Physiol Cell Physiol, 2004, Vol. 286, pp. C1390-C1398) showed that human erythrocytes sequentially reduce and take up MTC i.e. that MTC itself is not taken up by the cells but rather that it is the reduced from of MT that crosses the cell membrane. They also showed that the rate of uptake is enzyme dependent; and that both oxidised and reduced MT are concentrated in cells (reduced MT re-equilibrates once inside the cell to form oxidised MT).

Based on these and other disclosures, it is believed that orally administered MTC and similar drugs are taken up in the gut and enter the bloodstream, while unabsorbed drug percolates down the alimentary canal, to the distal gut. One important undesired side-effect is the effect of the unabsorbed drug in the distal gut, for example, sensitisation of the distal gut and/or antimicrobial effects of the unabsorbed drug on flora in the distal gut, both leading to diarrhoea.

MTC was tested clinically in a phase 2 study (Wischik et al., 2015). Although the minimum safe and effective dose was identified as 138 mg/day, a higher dose of 218 mg/day had limited efficacy due to absorption limitations, most likely due to the need for the $MT^+$ to be reduced to the leuco-MT (LMT) form to permit efficient absorption by passive diffusion.

WO2009/044127 disclosed the results of a phase 2 clinical trial, which indicated that MTC had two systemic pharmacological actions: cognitive effects and haematological effects, but that these actions were separable. Specifically the cognitive effects did not show a monotonic dose-response relationship, whereas the haematological effects did. It was proposed that two distinct species were responsible for the two types of pharmacological activity: MTC absorbed as the uncharged LMT form being responsible for the beneficial cognitive activity, and MTC absorbed as an oxidised dimeric species being responsible for the oxidation of haemoglobin. WO2009/044127 described how dosage forms could be used to maximise the bioavailability of the therapeutically active (cognitively effective) species whether dosing with oxidised or leuco-DAPTZ compounds.

Since it is the reduced form of MT that is taken up by cells, it has been proposed to administer a reduced form to patients. This may also reduce reliance on the rate-limiting step of enzymatic reduction.

MTC, a phenothiazin-5-ium salt, may be considered to be an "oxidized form" in relation to the corresponding 10H-phenothiazine compound, N,N,N',N'-tetramethyl-10H-phenothiazine-3,7-diamine, which may be considered to be a "reduced form":

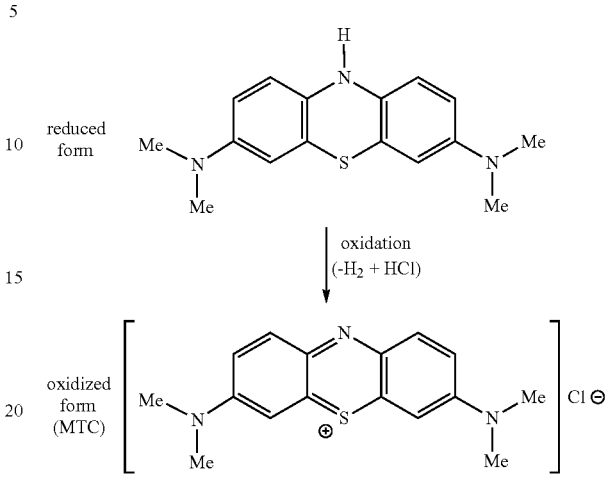

The "reduced form" (or "leuco form") is known to be unstable and can be readily and rapidly oxidized to give the corresponding "oxidized" form.

WO 02/055720 discloses the use of reduced forms of certain diaminophenothiazines for the treatment of protein aggregating diseases, primarily tauopathies. Based on in vitro activity for the reduced forms of diaminophenothiazines therein, a suggested daily dosage was 3.2-3.5 mg/kg, and dosages of 20 mg t.d.s., 50 mg t.d.s. or 100 mg t.d.s., combined with 2× mg ratio of ascorbic acid in such a manner as to achieve more than 90% reduction prior to ingestion were also described.

WO2007/110627 disclosed certain 3,7-diamino-10H-phenothiazinium salts, effective as drugs or pro-drugs for the treatment of diseases including Alzheimer's disease and other diseases such as Frontotemporal dementia (FTD). These compounds are also in the "reduced" or "leuco" form when considered in respect of MTC. These leucomethylthioninium compounds were referred to as "LMTX" salts, and included the following salts:

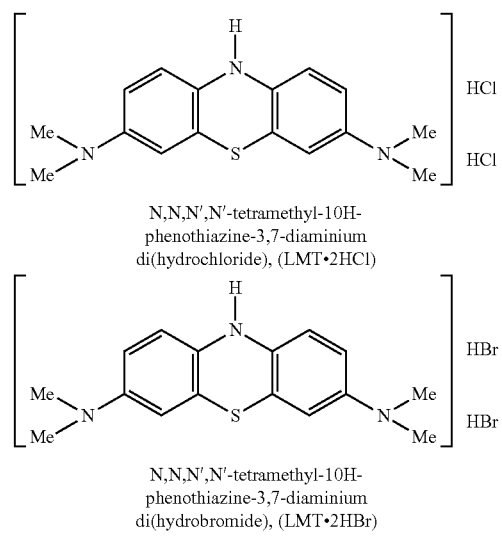

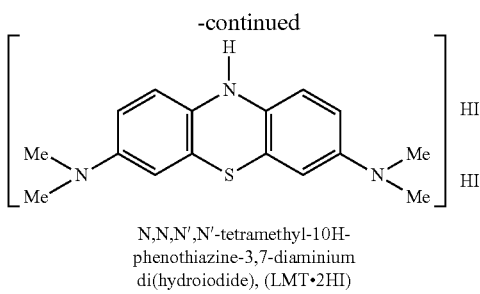

N,N,N',N'-tetramethyl-10H-
phenothiazine-3,7-diaminium
di(hydroiodide), (LMT·2HI)

WO2012/107706 described other LMTX salts having superior properties to the LMTX salts listed above, including leuco-methylthioninium bis(hydromethanesulfonate) (LMTM):

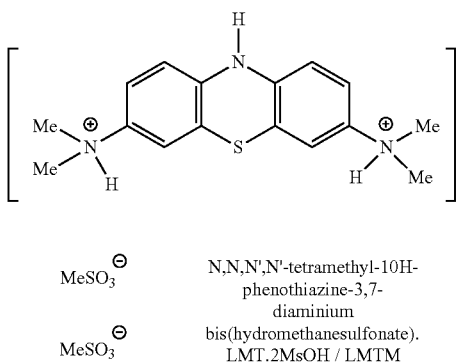

MeSO$_3^{\ominus}$   N,N,N',N'-tetramethyl-10H-
              phenothiazine-3,7-
              diaminium
MeSO$_3^{\ominus}$   bis(hydromethanesulfonate).
              LMT.2MsOH / LMTM Specifically LMTM retains TAI activity in vitro and in vivo (Harrington et al., 2015; Melis et al., 2015) has superior pharmaceutic properties in terms of solubility and pKa, and is not subject to the absorption limitations of the MT$^+$ form (Baddeley et al., 2015).

WO2007/110627 and WO2012/107706 describes dosage units comprising 20 to 300 mg of the DAPTZ compounds described therein e.g. 30 to 200 mg, for example 30 mg, 60 mg, 100 mg, 150 mg, 200 mg. A suitable dose of the DAPTZ compound is suggested in the range of about 100 ng to about 25 mg (more typically about 1 µg to about 10 mg) per kilogram body weight of the subject per day e.g. 100 mg, 3 times daily, 150 mg, 2 times daily, 200 mg, 2 times daily.

WO2018/019823 describes novel regimens for treatment of neurodegenerative disorders utilising methylthioninium (MT)-containing compounds. Briefly, these regimens identified two key factors. The first was in relation to the dosage of MT compounds, and the second was their interaction with symptomatic treatments based on modulation of acetylcholinesterase levels.

In the analysis described in WO2018/019823, low doses of MT compounds (for example 4 mg b.i.d) showed therapeutic benefits when monotherapy was compared against add-on. The efficacy profiles were similar in mild and moderate subjects for most of the measured outcomes.

Furthermore, treatment benefit in AD (according to the trial criteria) was restricted to patients taking LMTM as monotherapy. By contrast, the decline seen at corresponding doses in patients taking LMTM in combination with AD-labelled treatments (acetylcholinesterase inhibitors [AChEIs] and\or memantine), who were the majority, was indistinguishable on all parameters from that seen in the control arm.

The potential for LMT compounds to be active at the low dose, and the apparent lack of a dose-response, are discussed in WO2018/019823 and it is hypothesised that there may be a critical threshold for activity at the tau aggregation inhibitor target, and that the effect of higher doses may plateau or may even become negative at brain concentrations above 1 M (Melis, 2015). Based on these analyses, and given that lower doses (4 mg twice a day) had a better overall clinical profile than the high dose (100 mg twice a day), WO2018/019823 teaches methods of treatment of neurodegenerative disorders of protein aggregation which comprise oral administration of MT-containing compounds, wherein said administration provides a total of between 0.5 and 20 mg of MT to the subject per day, optionally as a single dose or split into 2 or more doses.

Other publications using "low dose" or "low dosage" in relation to MT-containing compounds are described in WO2018/019823. For example:

Telch, Michael J., et al. "Effects of post-session administration of methylene blue on fear extinction and contextual memory in adults with claustrophobia." American Journal of Psychiatry 171.10 (2014): 1091-1098: this publication refers to the use of "low-dose methylene blue" on retention of fear extinction and contextual memory following fear extinction training. The paper reports that "Methylene blue is a diamino phenothiazine drug that at low doses (0.5-4 mg/kg) has neurometabolic-enhancing properties. The dosages used in the publication were 260 mg/day for adult participants, corresponding to a 4 mg/kg dose.

Gonzalez-Lima F and Auchter A (2015) "Protection against neurodegeneration with low-dose methylene blue and near-infrared light". Front. Cell. Neurosci. 9:179. doi: 10.3389/fncel.2015.00179: this publication discusses the cellular mechanisms mediating the neuroprotective effects of low doses of methylene blue and near-infrared light. It refers to earlier work citing 0.5-4 mg/kg of methylene blue as safe and effective.

Alda, Martin, et al. "Methylene blue treatment for residual symptoms of bipolar disorder: randomised crossover study." The British Journal of Psychiatry (2016): doi: 10.1192/bjp.bp.115.173930: this publication described the use of a 15 mg "low dose" of methylene blue as a placebo in a 6 month trial. The "active dose" was 195 mg. In each case the dose was split three times daily.

Rodriguez, Pavel, et al. "Multimodal Randomized Functional MR Imaging of the Effects of Methylene Blue in the Human Brain." Radiology (2016): 152893: this publication also refers to the 'known' pharmacokinetic and side effects of "low-dose" (0.5-4.0 mg/kg) methylene blue, which are contrasted with the effects of dosages greater than 10 mg/kg. The dosages used in the publication were 280 mg/day for adult participants, approximating to a 4 mg/kg dose.

Naylor et al. (1986) "A two-year double-blind crossover trial of the prophylactic effect of methylene blue in manic-depressive psychosis". Biol. Psychiatry 21:915-920 and Naylor et al. (1987) A controlled trial of methylene blue in severe depressive psychosis. Biol. Psychiatry 22:657-659: these studies used 15 mg/day methylene, nominally as a placebo vs. a treatment of 300 mg/day methylene blue. However, in the latter paper the authors proposed that the placebo dosage may act as an antidepressant.

As discussed above, because of their activity in respect of tau aggregation and TDP-43 aggregation, MT-based compounds have been suggested for the treatment of FTD (see WO2007/110630; WO2007/110627; WO2009/044127; WO2012/107706, all described supra).

WO2018/041739 describes the results of a phase 3 clinical trial investigating the treatment of Frontotemporal dementia (FTD) disease using LMTM.

The results indicated that even a relatively low dose of the MT compound (which was used in the trial as a control) may show benefit in FTD, as compared to the cognitive decline seen in historical controls.

Furthermore, unexpectedly, the results indicated strong interaction effects when MT is co-medicated with AD treatments which modify synaptic neurotransmission in the brain. There appeared significant cognitive benefits in FTD patients taking MT in combination with such AD treatments (e.g. acetylcholinesterase inhibitors and/or memantine) compared to MT alone. WO2018/041739 further describes how MT compounds can be combined with acetylcholinesterase inhibitors and/or memantine without apparent incompatibility.

The insights provided in WO2018/019823 and WO2018/041739 provide an important contribution to the art in relation to the minimum dosing of MT compounds to achieve cognitive benefit in subjects suffering from, or at risk of, neurodegenerative disorders such as AD and FTD.

Nevertheless it is well known that there is inter-individual variability between subjects in respect of how a given dosage of a drug will translate into the concentration of the drug in the subject's body fluids. It is advantageous that any dosing regimen which is to be applied to populations of such subjects can as far as possible take such variability into account, in order to ensure maximal therapeutic benefit for all subjects, without the need for personalised regimes, and while nevertheless maintaining a desirable clinical profile.

DISCLOSURE OF THE INVENTION

The present inventors have devised a novel pharmacokinetic (PK) model for dosing MT compounds in patient populations. This versatile model was derived from a Phase 1 study in elderly volunteers, and is described in the Examples hereinafter.

The novel population PK model was then used to estimate Cmax of parent MT in patients who received LMTM in the two phase 3 trials of AD studies described in WO2018/019823 (Studies "005" and "015", for treatment of mild, or mild to moderate, AD patients respectively). Once the Cmax was estimated in each of the subjects, a distribution of Cmax estimates for each of the treated population could be derived.

As expected, there was substantial variability in the MT Cmax values across the population for the given low dosage. Analysis of this distribution confirmed the findings in WO2018/019823 that low dosages (4 mg MT bid) were efficacious (as measured, for example, by reduced decline on the Alzheimer's Disease Assessment Scale-cognitive subscale (ADAS-cog). It further confirmed that monotherapy gave a substantial benefit by this criterion compared to add-on therapy with AChEIs and\or memantine (with the mean benefit of between monotherapy and add-on being ~4 ADAS-cog units over 65 weeks)(see FIG. 3a).

Figure 12:
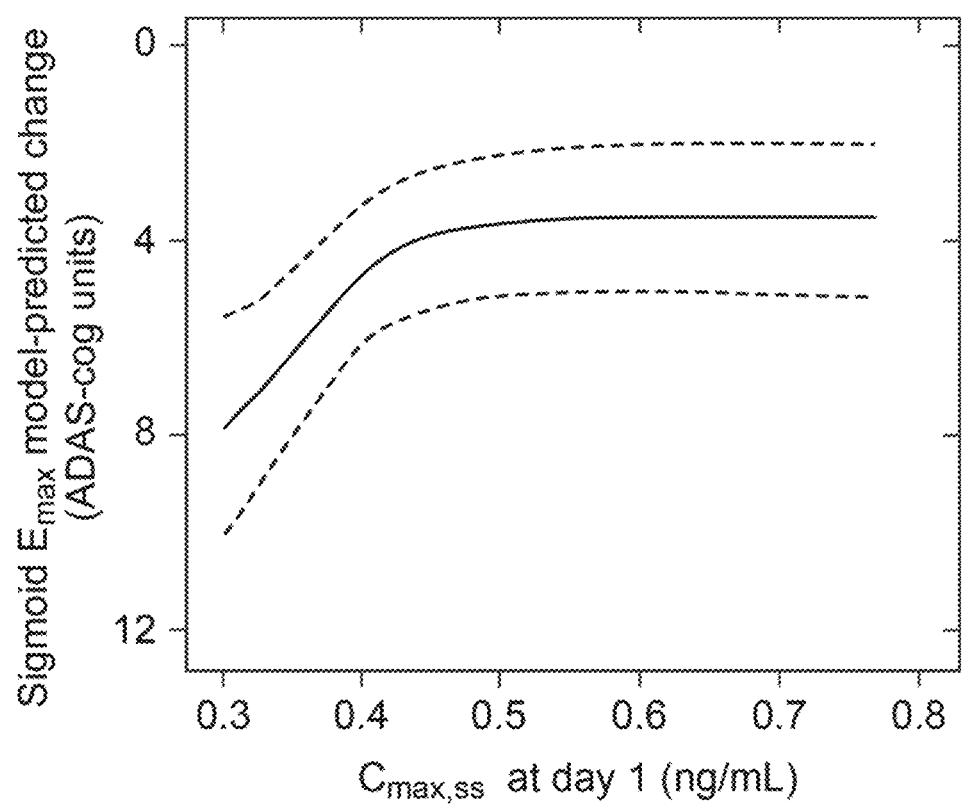
Figure 13A:
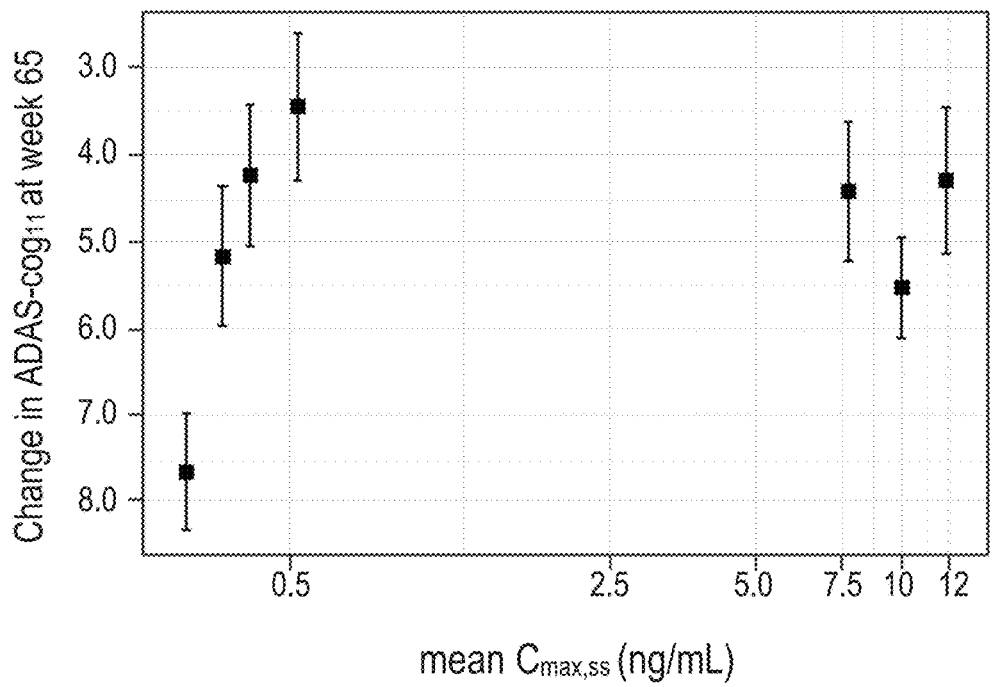
Figure 13B:
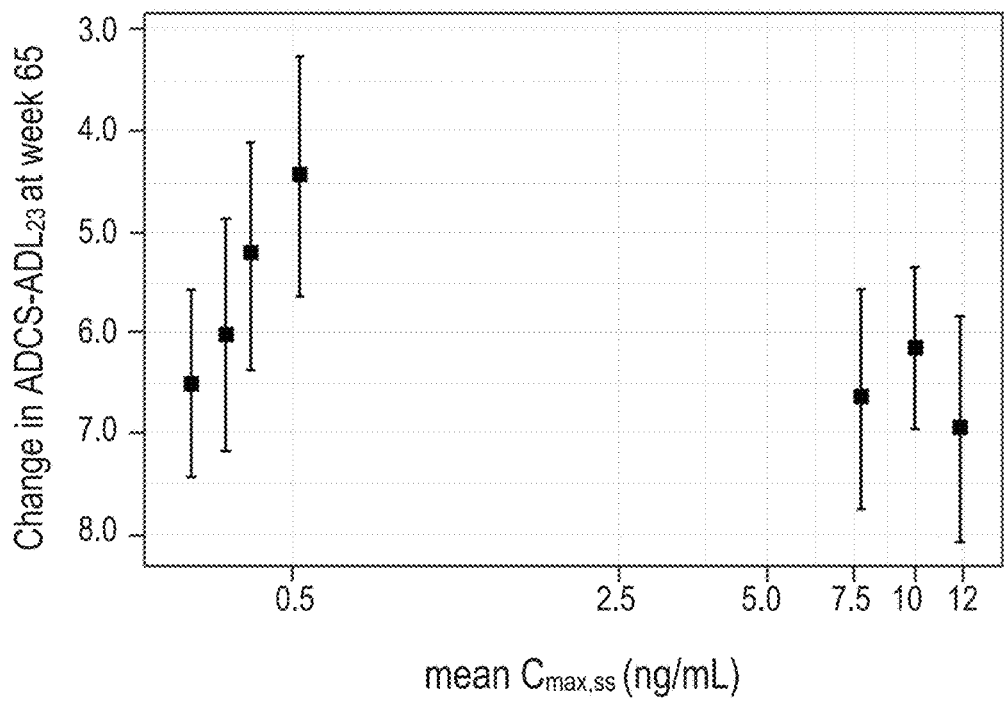
Figure 13C:
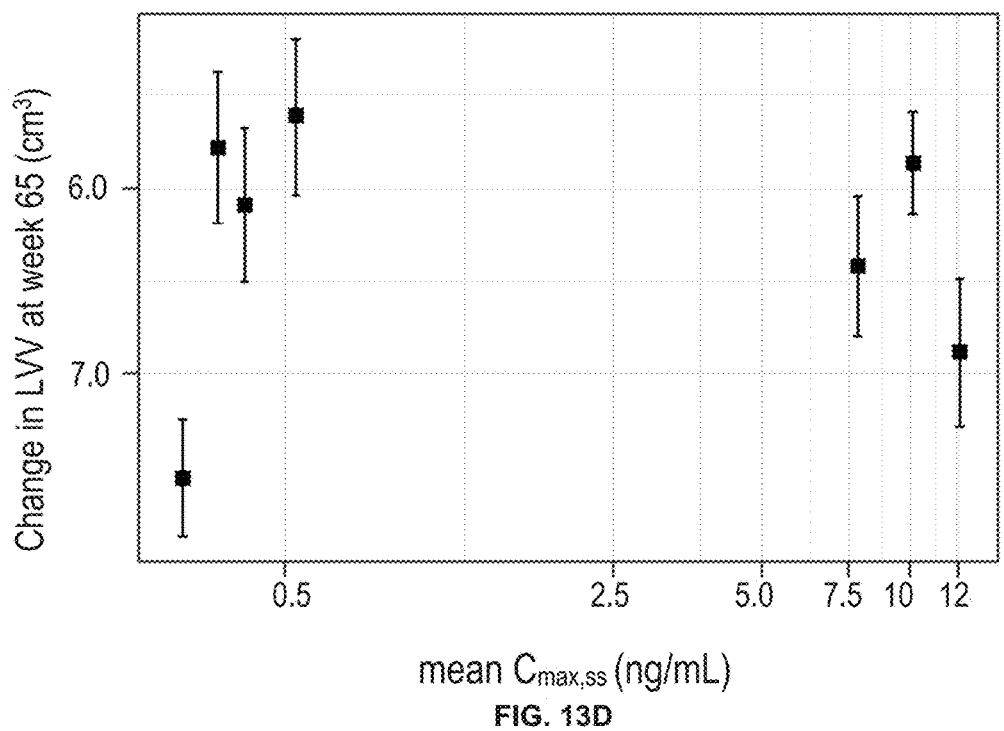
Figure 13D:
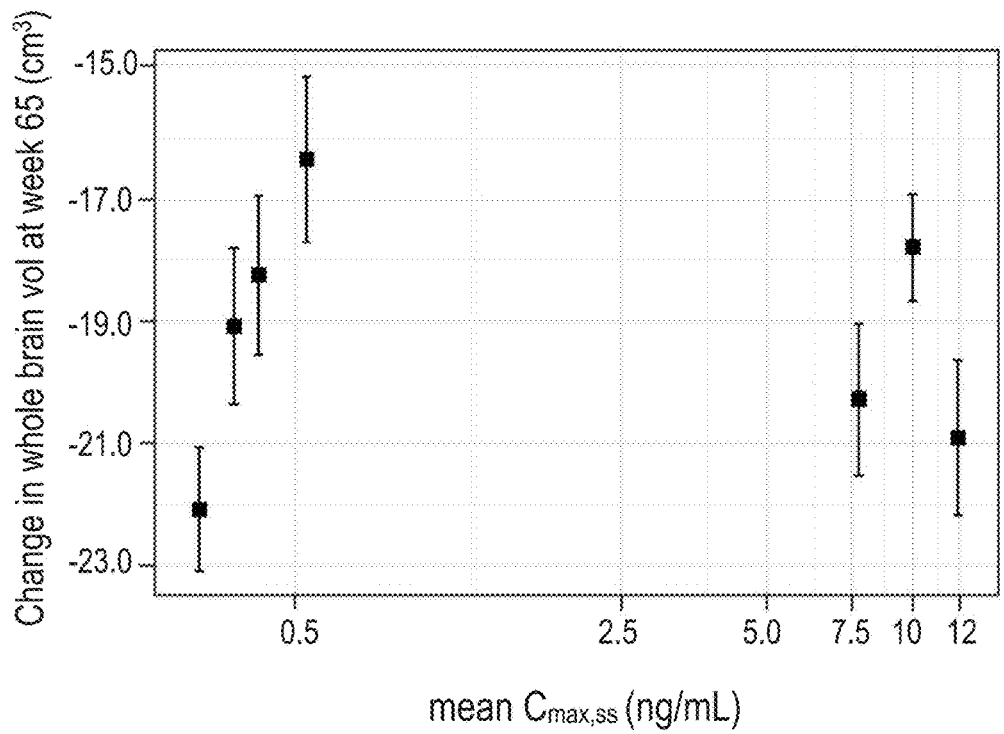
Figure 14A:
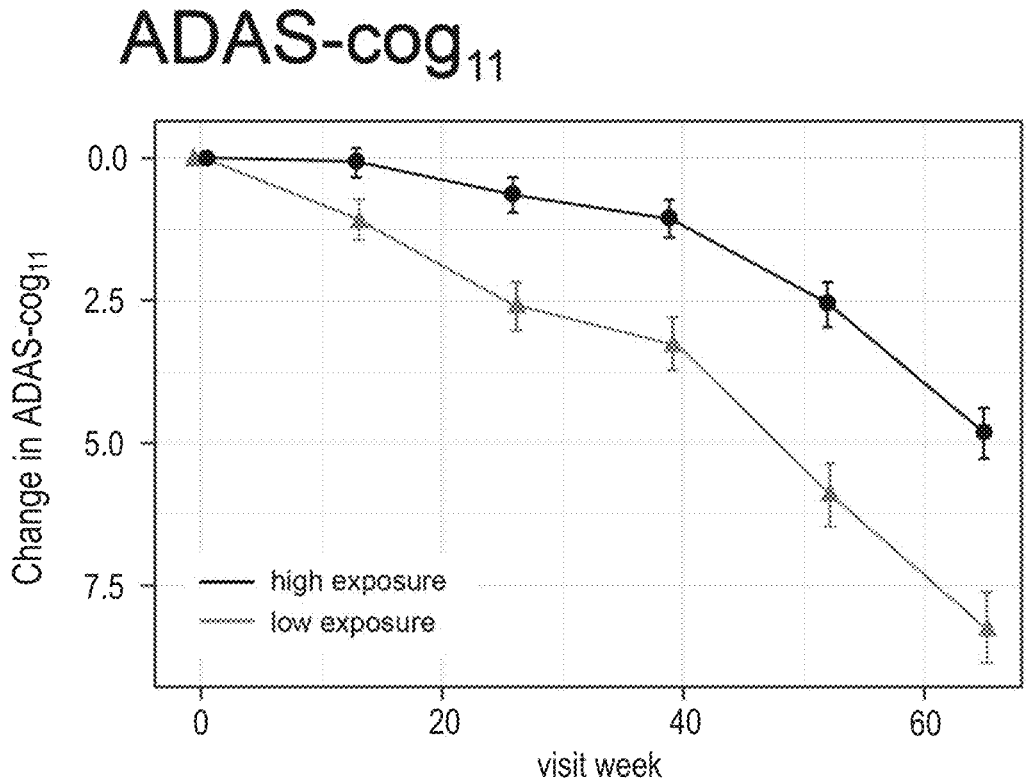
Figure 14B:
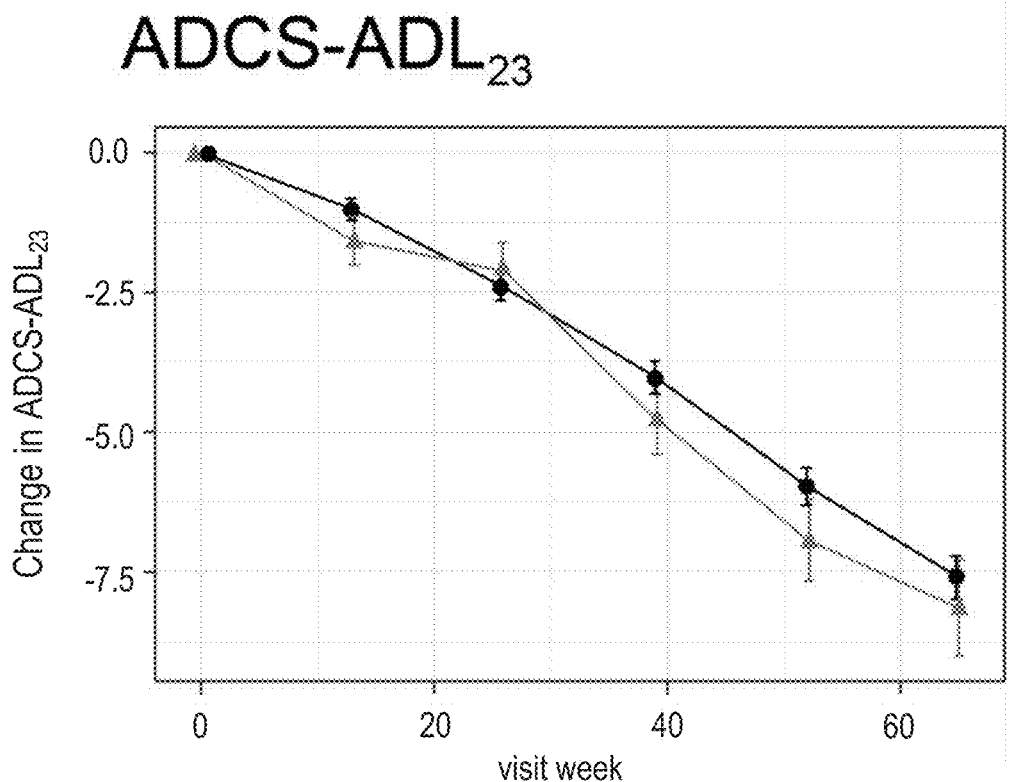
Figure 14C:
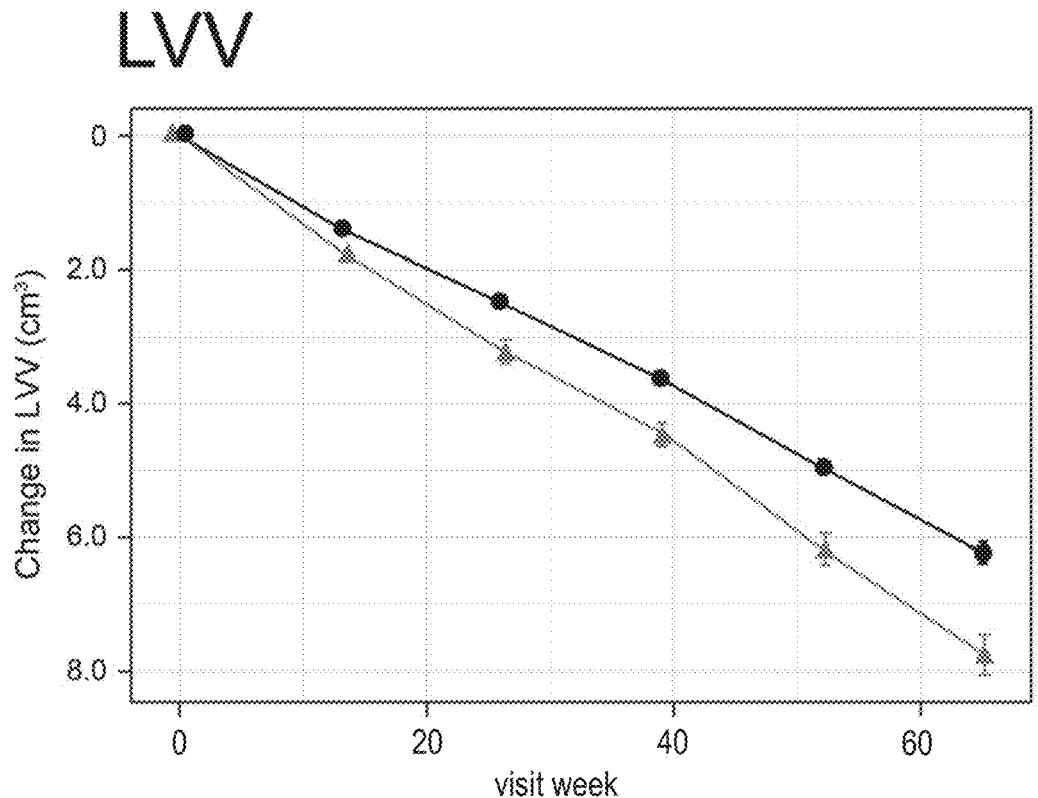
Figure 14D:
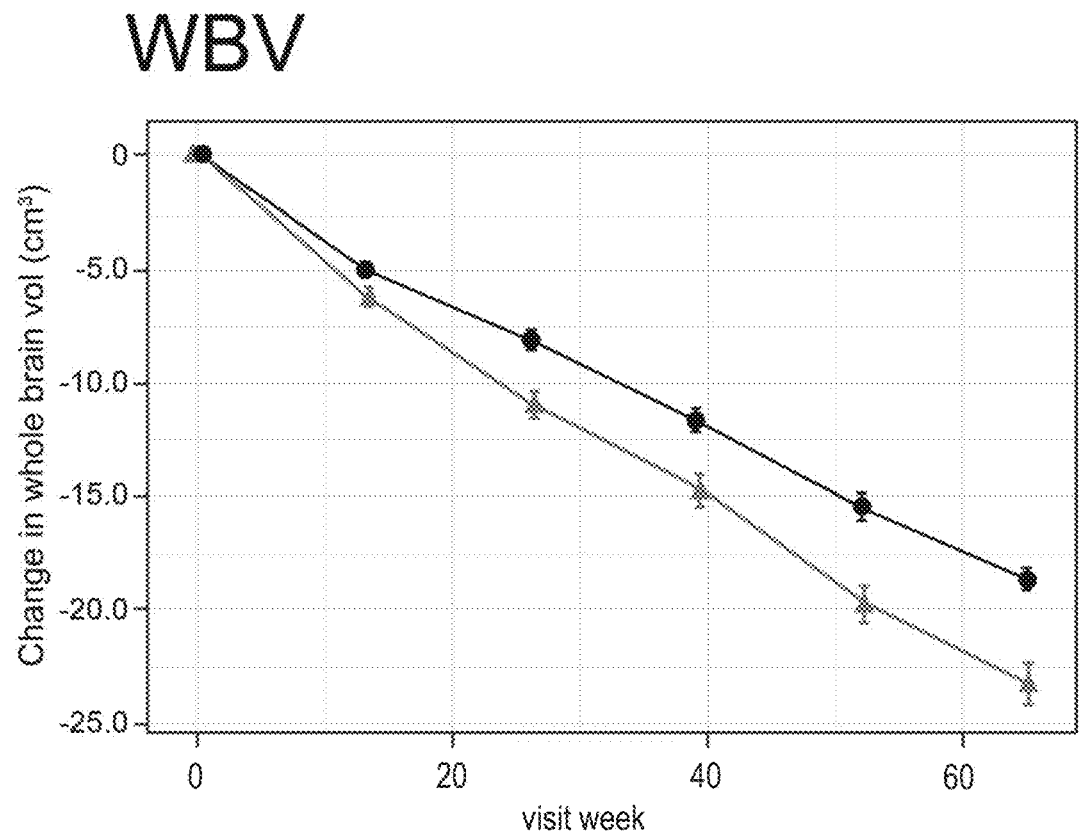
Figure 16A:
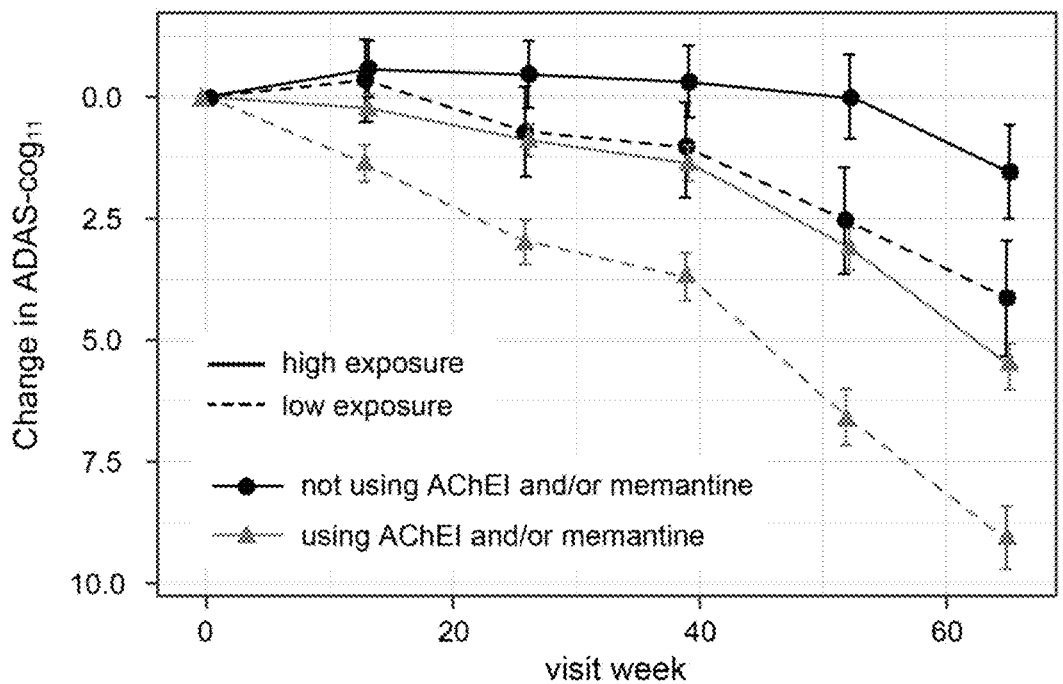
Figure 16B:
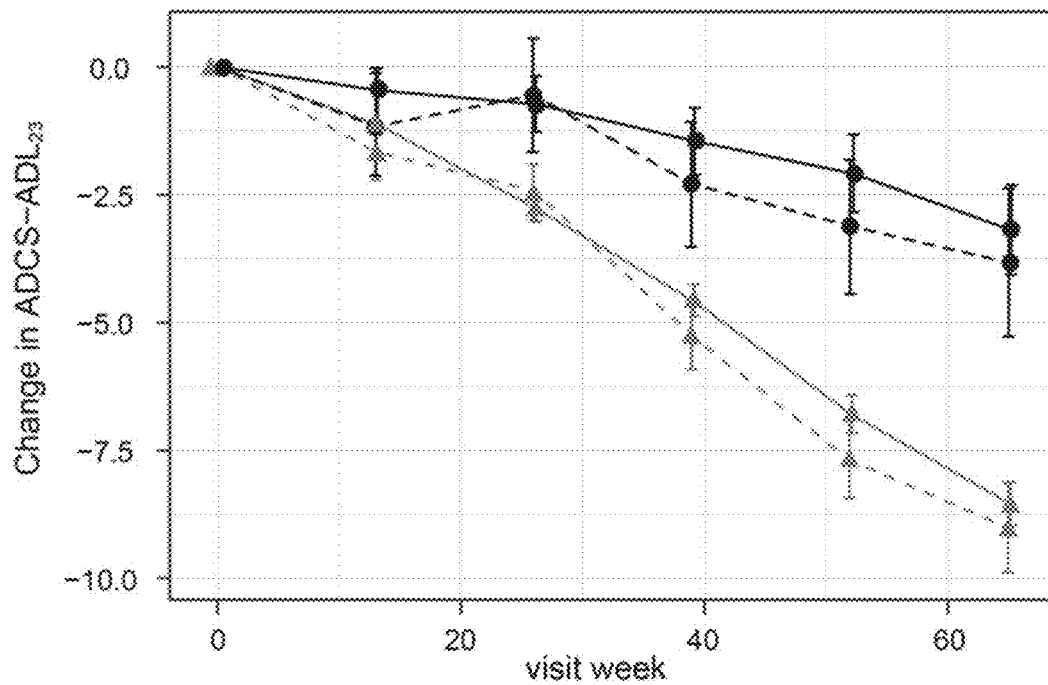
Figure 16C:
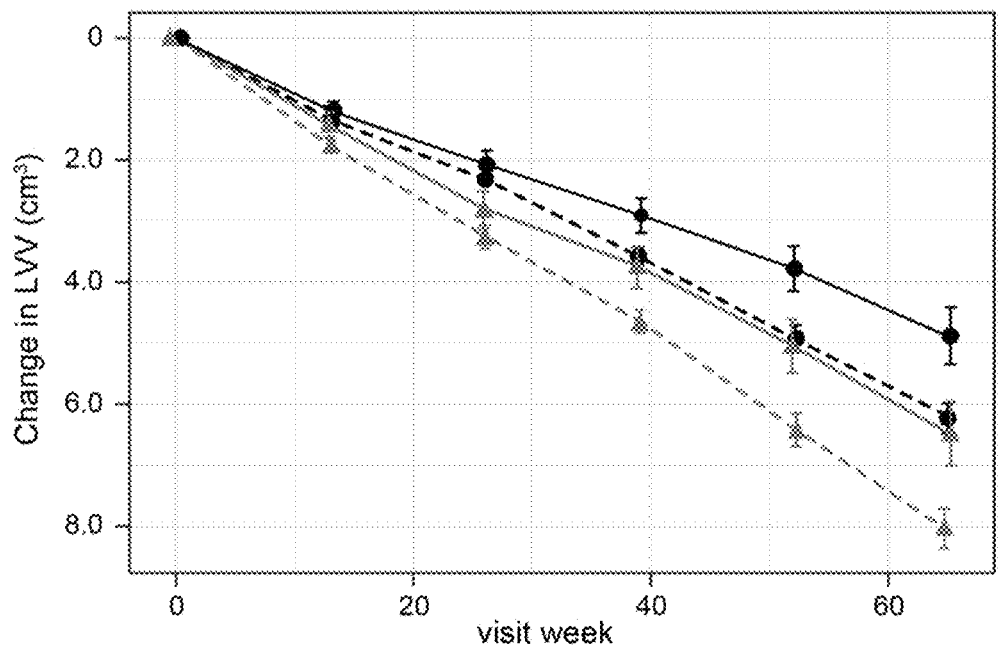
Figure 16D:
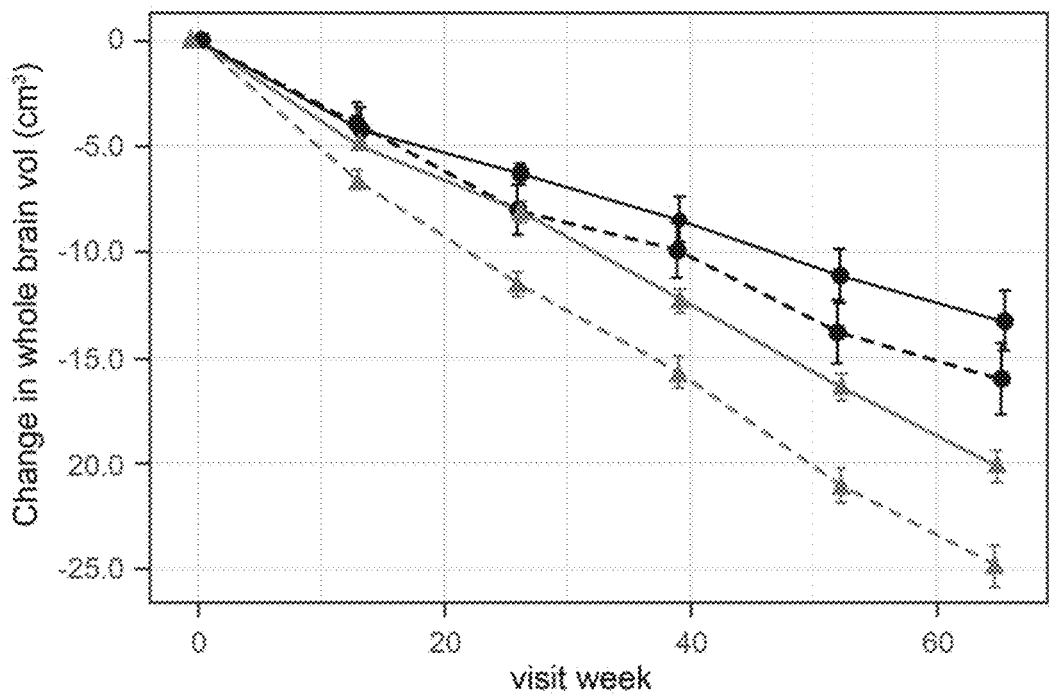

However, unexpectedly in view of the published literature which described a lack of recognisable dose response, the novel analysis revealed that there exists a concentration response within the low dose treated population. This can be shown for patients receiving the 8 mg/day using a sigmoid $E_{max}$ analysis for for ADAS-cog$_{11}$ decline over 65 weeks in patients pooled from Studies 015 and 005 (FIG. 12).

Figure 3A:
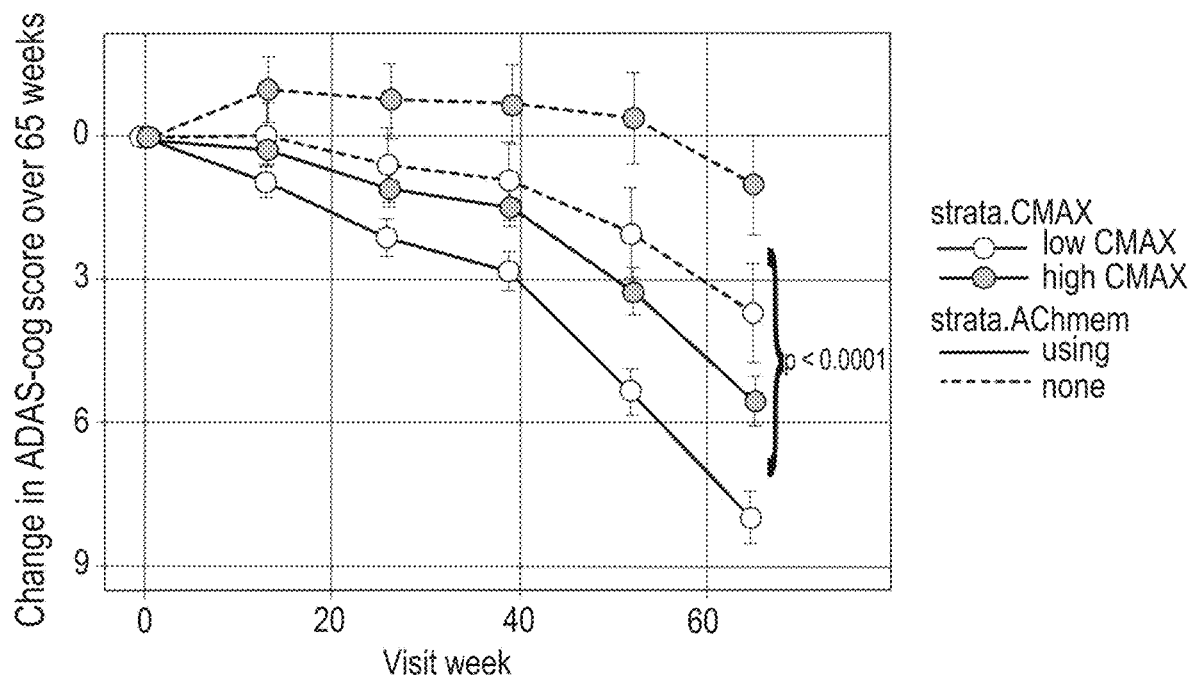

Based on a median Cmax threshold split of the population, the group of individuals with "high" estimated Cmax showed an improvement of around ~2 to 3 ADAS-cog units compared to the group of individuals with "low" estimated Cmax (see FIG. 3a).

However based on splitting of patients according to the threshold of 0.373 ng/ml, that encompasses the 35% of patients with the lowest values, the treatment difference in patients receiving the 8 mg/day dose is −3.4 ADAS-cog units (see FIG. 14).

These insights suggest that it is advantageous to adopt a dosing regimen which both maximises the proportion of subjects in which the MT concentration will exceed the $C_{max}$ or $C_{ave}$ threshold, and also maximises the expected therapeutic efficacy of LMTM whether it is taken alone or in combination with (or at least preceded by) symptomatic treatments, while nevertheless maintaining a relatively low dose so as to maintain a desirable clinical profile in relation to being well tolerated with minimal side-effects.

Figure 17:
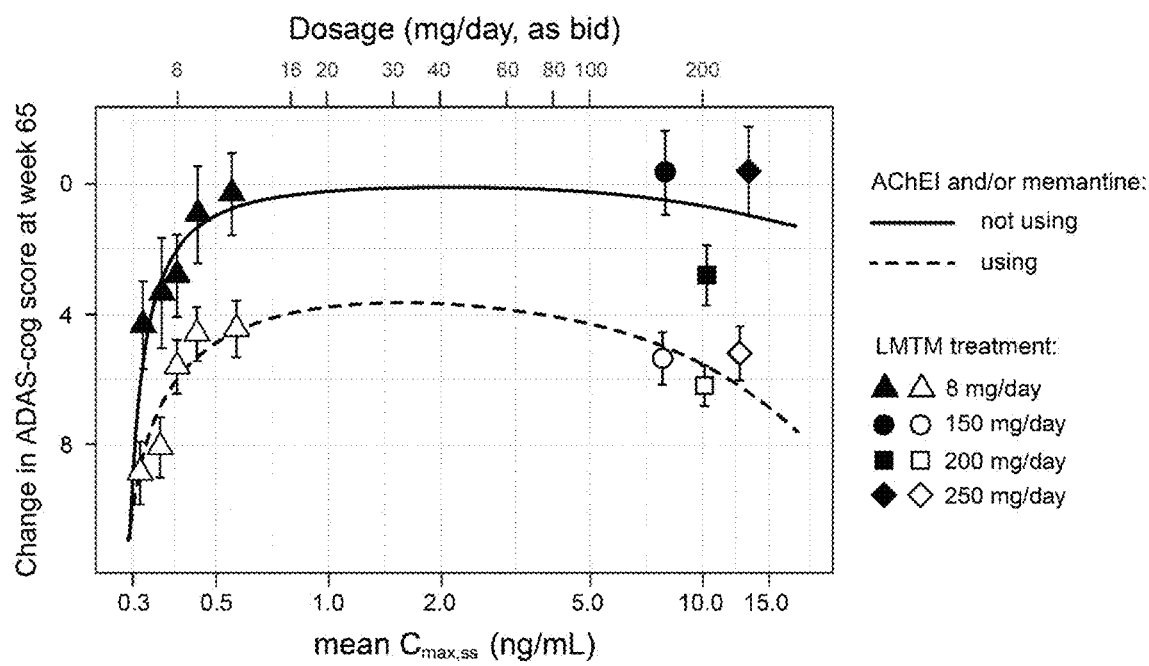
Figure 18A:
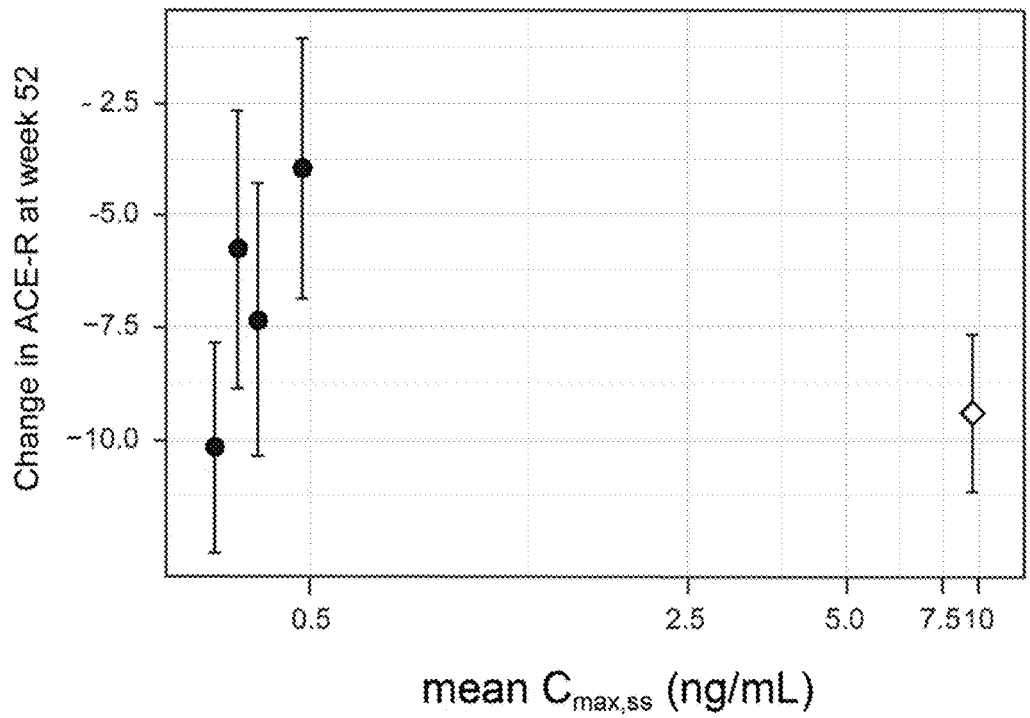
Figure 18B:
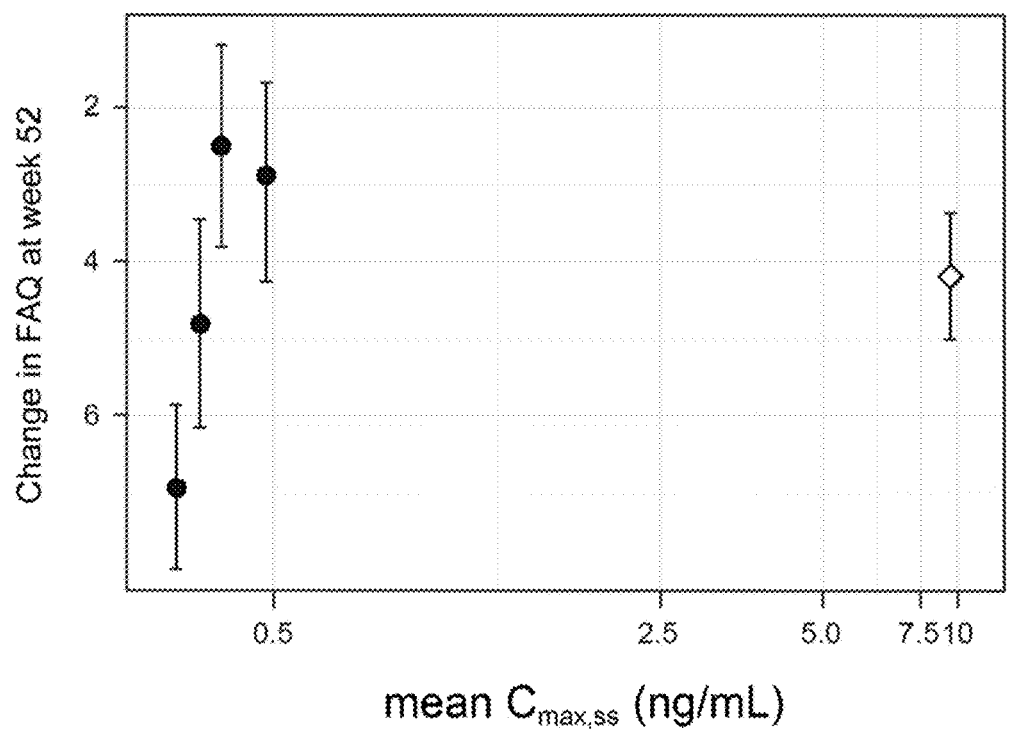
Figure 18C:
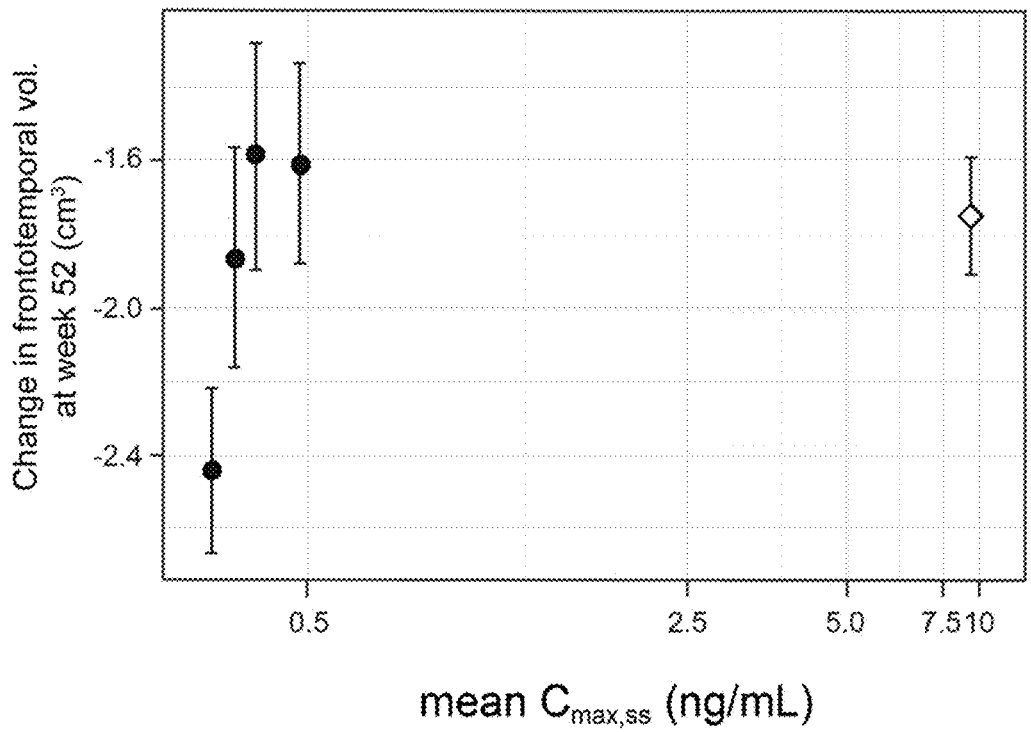
Figure 18D:
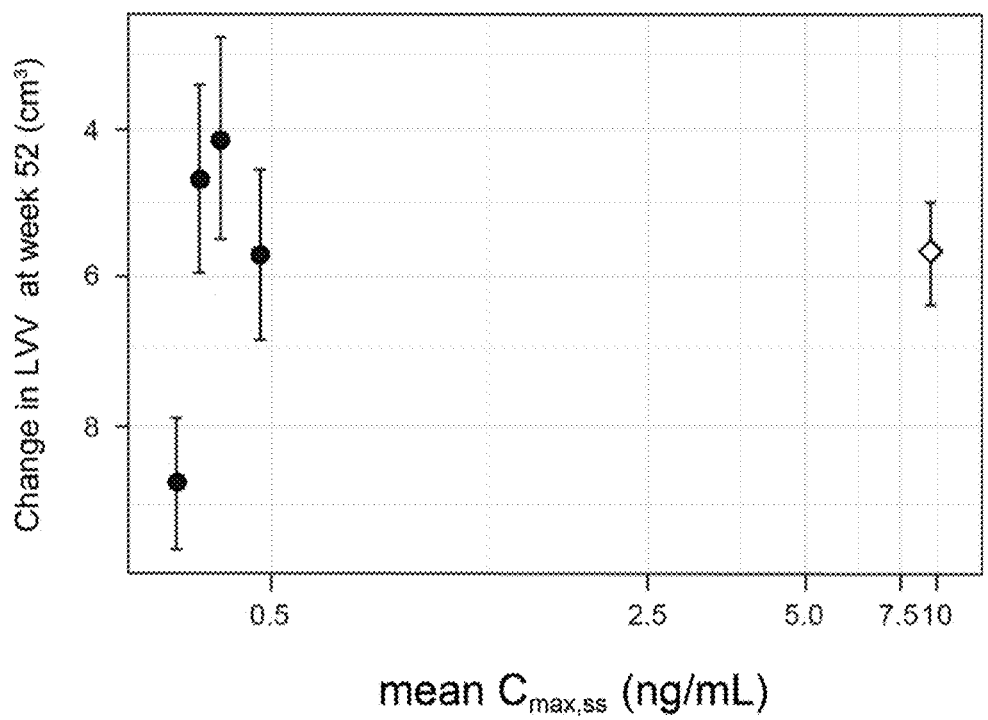
Figure 18E:
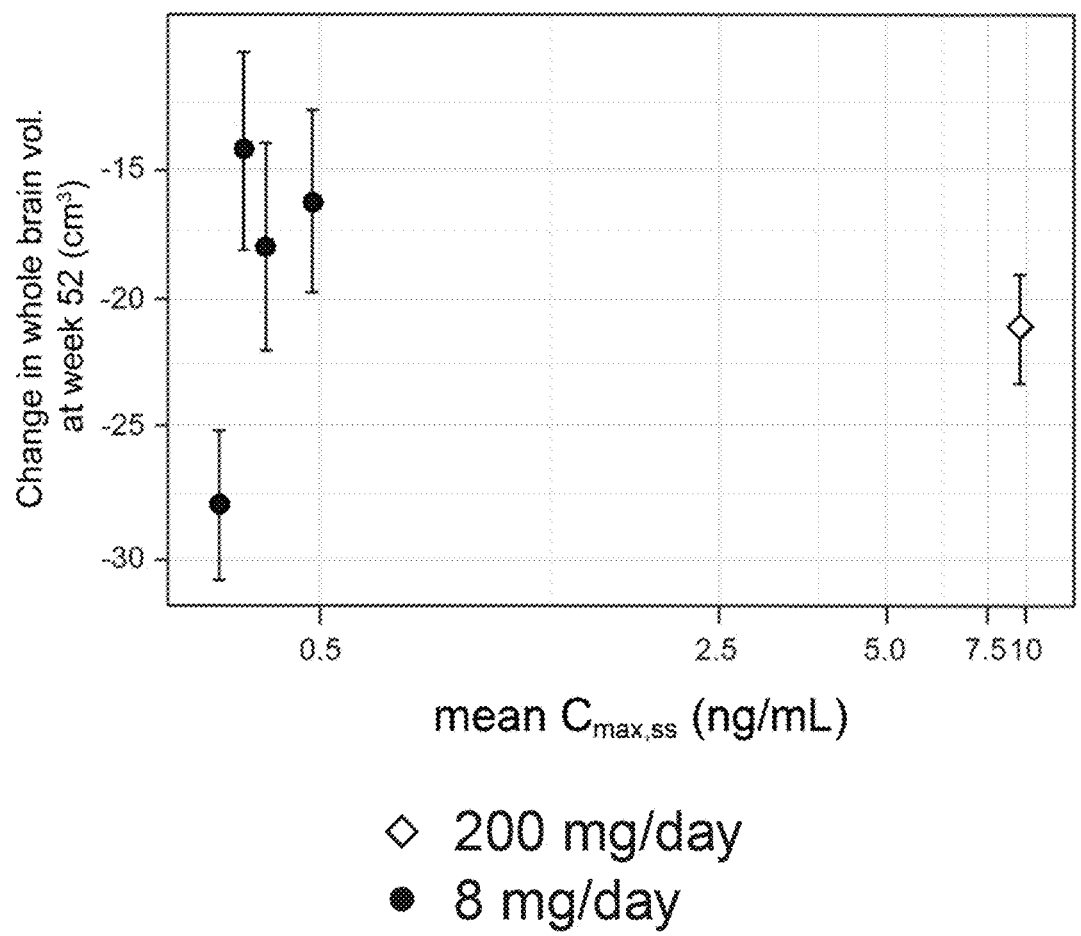
Figure 19A:
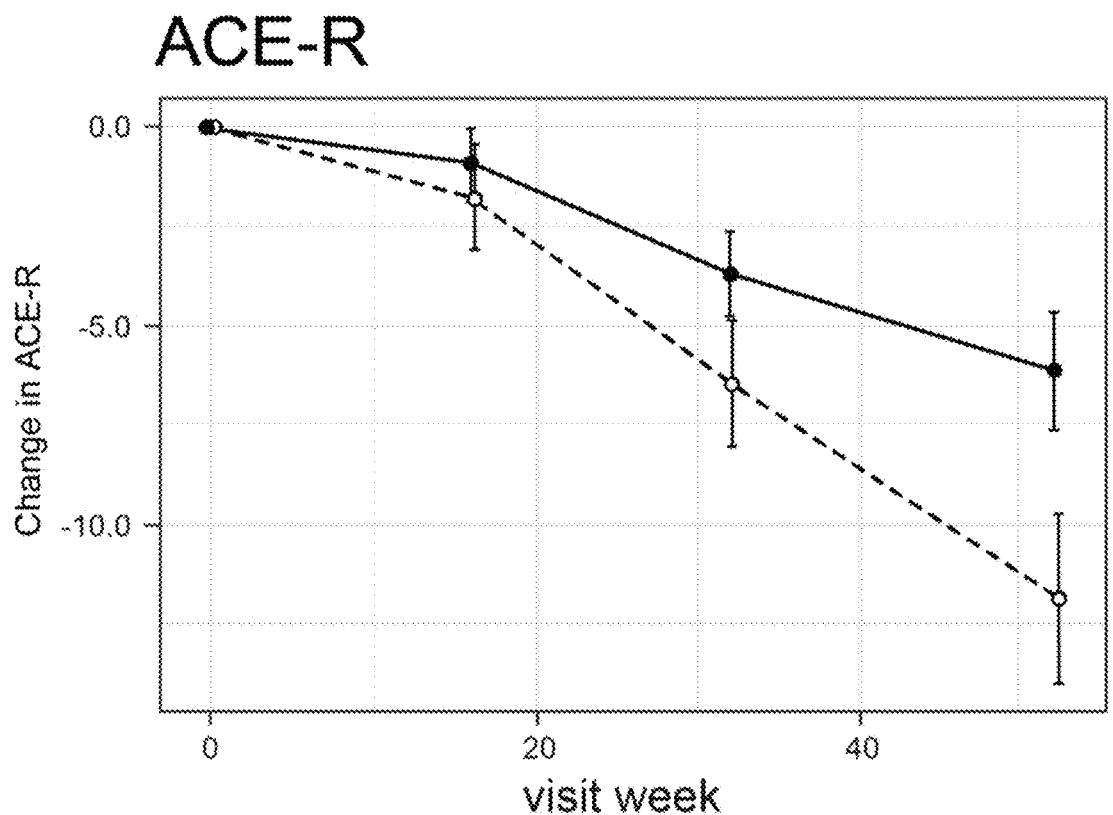
Figure 19B:
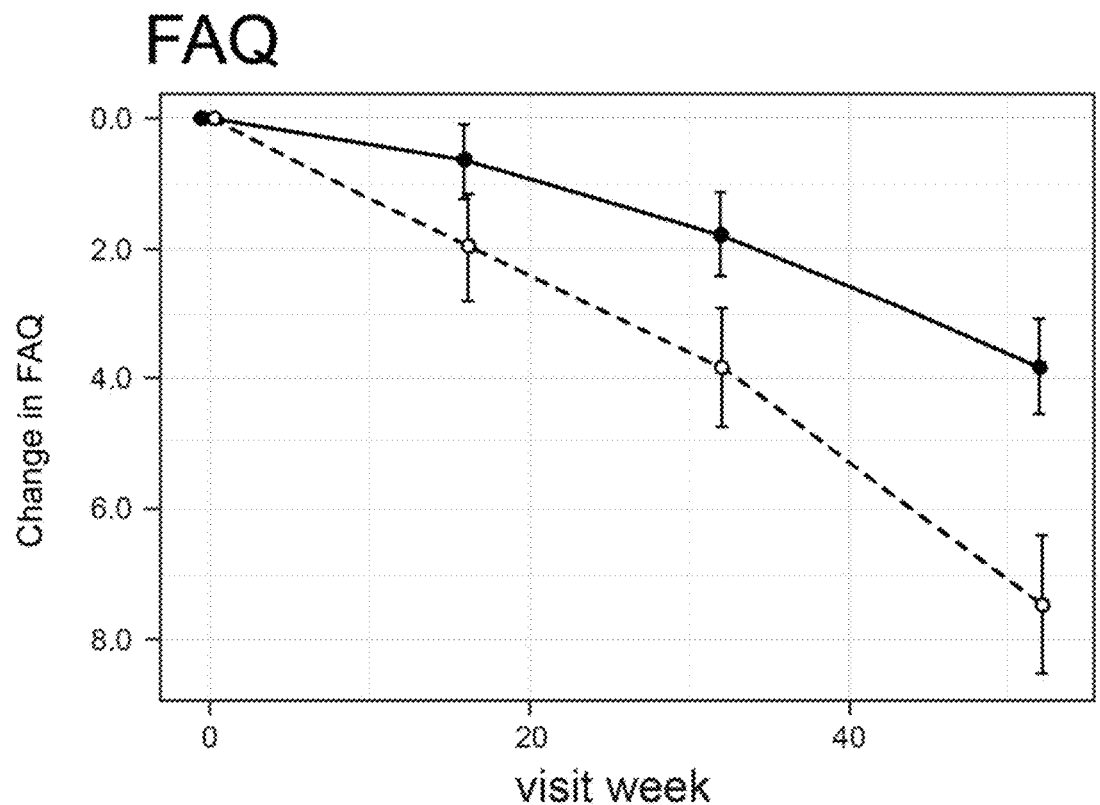
Figure 19C:
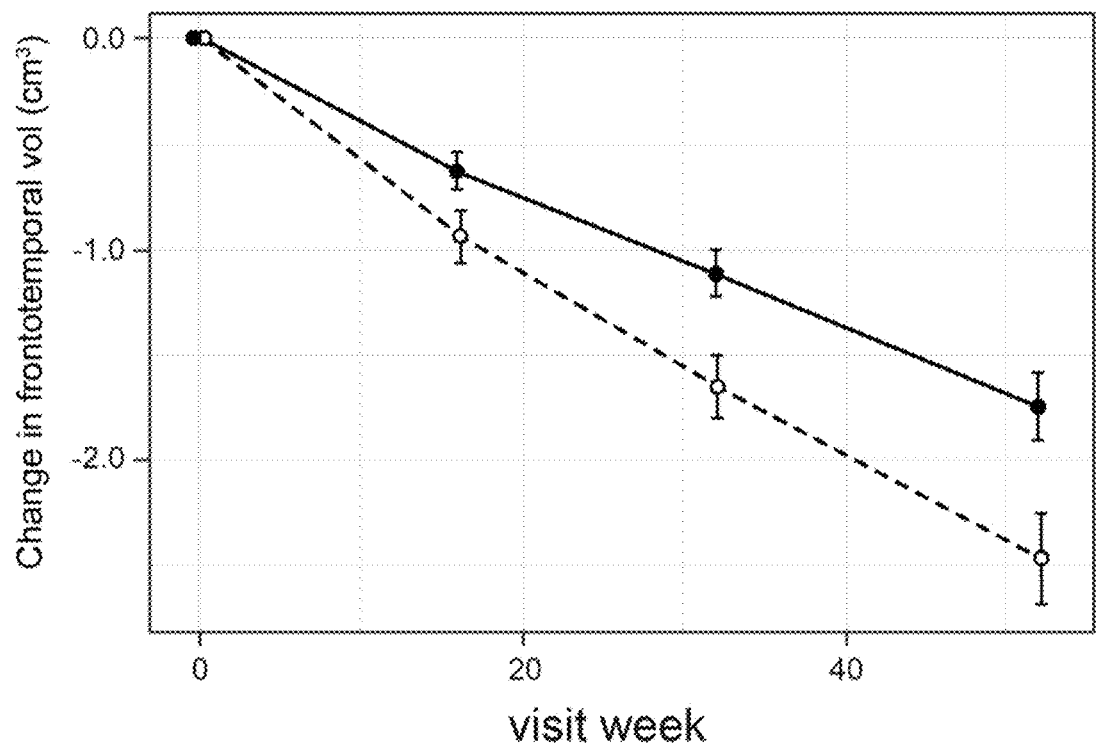
Figure 19D:
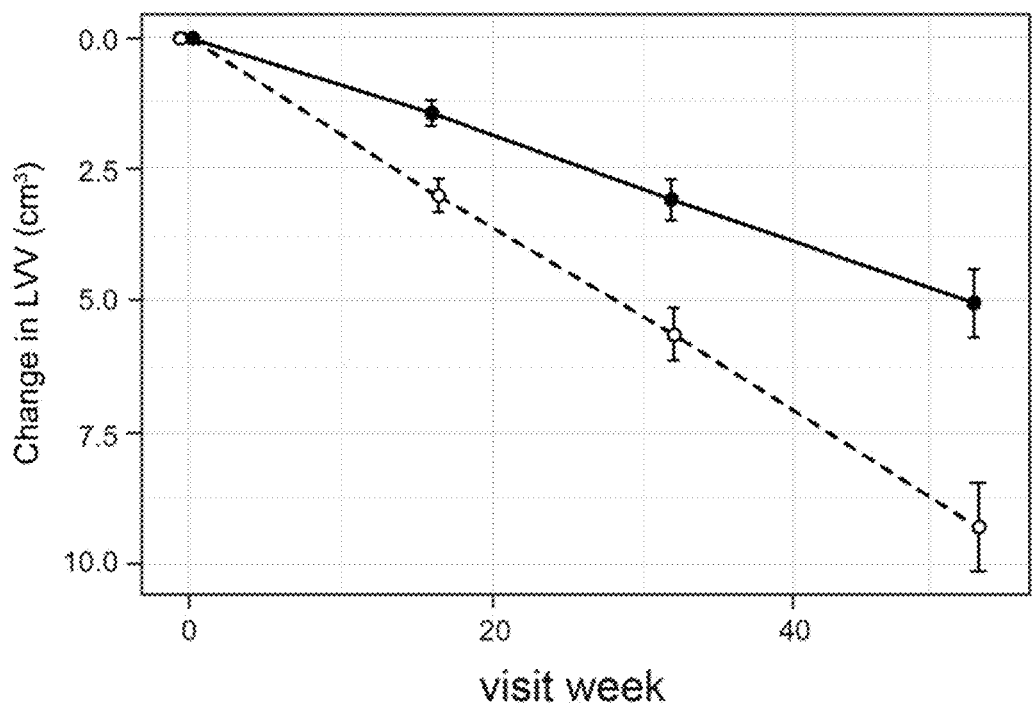
Figure 19E:
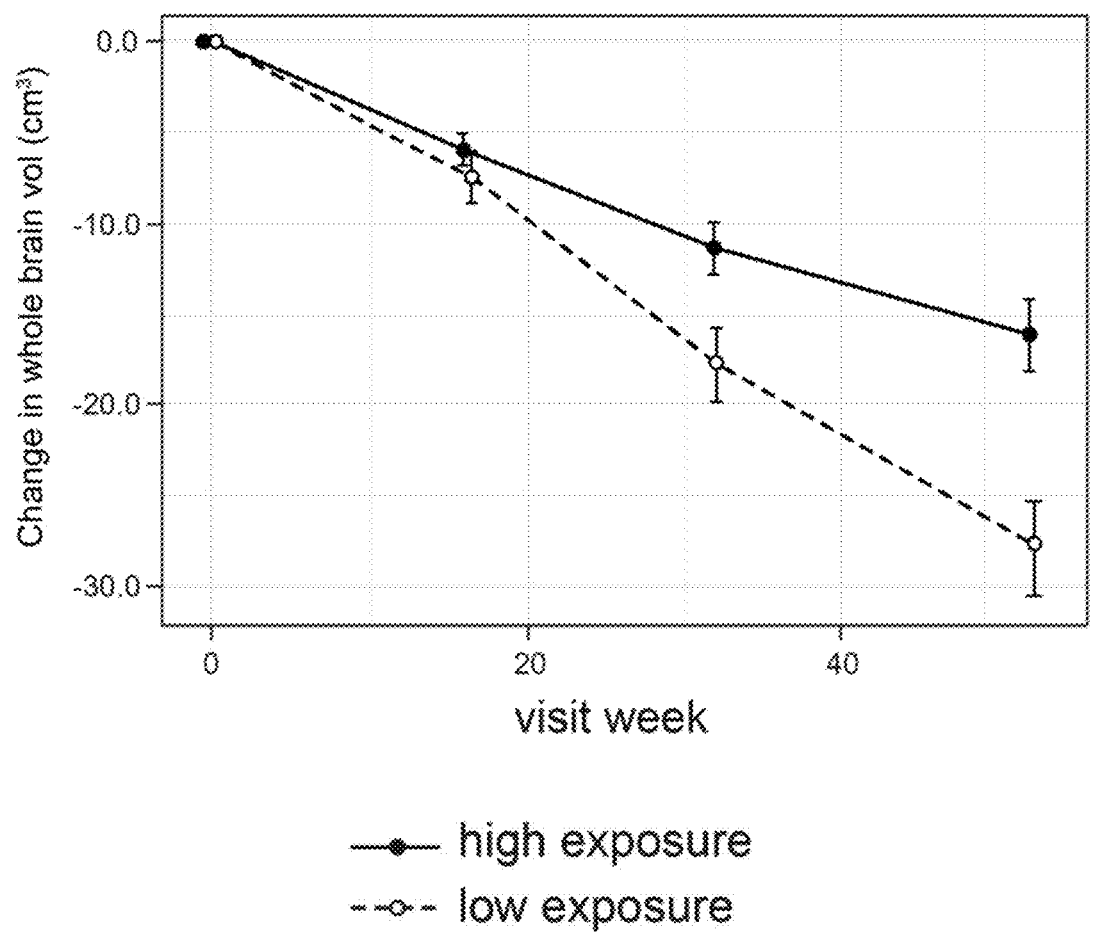

The overall biphasic concentration-response for LMTM shown in FIG. 17 supports the proposition that the minimum dose which achieves all these objectives is at least 20 mg/day, and doses in the range 20-40 mg/day, or 20-60 mg/day would be expected to maximise the therapeutic benefit, although good efficacy, particularly in AD patients not pre-treated with symptomatic treatments, can still be seen at dosages of 100 mg or more.

The novel population PK model was additionally used to estimate Cmax of parent MT in patients who received different dosages of LMTM bid in the phase 3 clinical trial investigating the treatment of bvFTD described in WO2018/041739.

These results confirmed the concentration-response relationship for low dose monotherapy for clinical benefit measured by change over 52 weeks on the cognitive scale (ACE-R) and on the functional scale (FAQ) similar to that seen in AD. There is a similar concentration-response relationship for measures of progression of brain atrophy by MRI (frontotemporal volume, lateral ventricular volume, whole brain volume). This is shown in FIG. 18.

As can be seen comparing the corresponding expanded Hill equation plots of AD and bvFTD (FIG. 17 and FIG. 20), the biphasic nature of the concentration-response relationship is more evident in bvFTD. This implies that the optimum dosing range to achieve maximum treatment benefit in bvFTD is somewhat narrower in bvFTD, namely 20-40 mg/day, or less preferably 20-60 mg/day.

As previously seen in in WO2018/041739, there is an additional benefit from combination with symptomatic treatments, which can particularly be seen in patients with plasma levels below the population mean for $C_{max,ss}$.

In the light of the results described herein, it can be seen that there are at least two distinct benefits to use the minimal dose of MT compound which maximises the benefit treatment effect. Firstly certain rare adverse events or side effects associated with MT occur in a dose-related fashion. Hence avoiding higher dosages than are necessary is clearly desirable in order to maintain an optimal clinical profile. Secondly, there is evidence of an inverse dose-response relationship for certain therapeutic criteria at high doses: thus benefit may actually be attenuated at high doses.

Overall these novel findings indicate that there is benefit in using slightly higher "low dose" LMT treatments than had previously been assumed, and further indicate that LMT treatments can, in some contexts, be advantageously used as add-on to symptomatic treatments, which increases the versatility of MT-based therapeutic regimes.

Further analysis by the inventors indicated that dosing above 20 mg MT (for example administered as LMTM) will achieve a Cmax above the median-derived threshold value in 90 to 100% of subjects (see FIG. 5), with the precise percentage being dependent on the number of split doses being employed.

In respect of AD treatments, such treatments would preferably be a monotherapy, or at least introduced either prior to or following cessation of the currently available AD treatments AChEIs and memantine. However, importantly, and as explained above, the analysis described herein indicates that even when using MT treatments as an add-on therapy, there can be benefit (of ~2 ADAS-cog units, or more) in dosing to achieve a Cmax above the threshold value, compared to a low Cmax value.

Thus in one aspect there is disclosed a method of therapeutic treatment of a neurodegenerative disorder, for example a neurodegenerative disorder (for example of protein aggregation, in a subject, which method comprises orally administering to said subject a methylthioninium (MT)-containing compound, wherein said administration provides a total daily dose of between 20.5 and 40, 20.5 and 50, 20.5 and 60, 20.5 and 70, 20.5 and 80, or 20.5 and 99 or 100 mg of MT to the subject per day, optionally split into 2 or more doses, wherein the MT-containing compound is a salt of

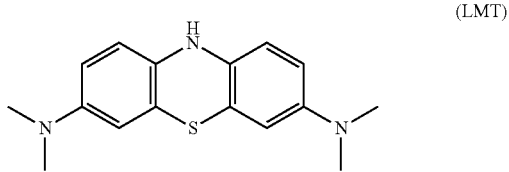

(LMT)

or a hydrate or solvate thereof.

The total daily MT dose may be between 20.5 or 21 and 60 mg.

The total daily dose may be about 20.5, 21, 21.5, 22, 22.5, 23, 23.5, 24 mg to around any of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 mg.

The total daily dose may be about 20.5, 21, 22, 23, 24, 25, 26, 27, 28, 29, 30, 31, 32, 33, 34, 35, 36, 37, 38, 39, 40 mg.

An example dosage is 20.5 or 21 to 40 mg.

A further example dosage is 22 to 35 mg.

A further example dosage is 23 to 30 mg.

The present invention concerns administering MT in the reduced (LMT) form.

The total daily dose of the compound may be administered as a split dose twice a day or three times a day.

As explained below, when administering the MT dose split in a larger number of doses/day it may be desired to use a smaller total amount within the recited range, compared to a single daily dosing, or a smaller number of doses per day.

As explained herein, in some embodiments, particularly in respect of treatment of AD, the treatment will be a monotherapy, or at least will exclude co-medication with AChEIs and memantine. In some embodiments subjects are selected who have had not had recent prior treatment which AChEIs or memantine or other symptomatic treatments, but such treatment is optionally started or re-started after commencement of treatment with LMT.

Thus, as explained herein, in other embodiments the treatment will be an add-on therapy, for example co-medication with AChEIs and\or memantine. Thus patients already receiving AChEIs and\or memantine may benefit from receiving these dosages of MT compound, while patients receiving these dosages of MT compound, may benefit from AChEIs and\or memantine.

In some embodiments the treatment is part of a treatment regimen which comprises:

(i) orally administering to said subject the MT-containing compound for a first period of time, wherein said administration provides a total daily dose of between 1 and 10 mg of MT to the subject per day, optionally 8 mg per day, optionally split into 2 or more doses;

(ii) orally administering to said subject the MT-containing compound for an immediately subsequent period of time, wherein said administration provides a total daily dose of between 20.5 and 40 mg, 20.5 and 60, 20.5 and 80 or 20.5 and 100 mg of MT to the subject per day, optionally about 21 to 40, 50, or 60 mg per day, optionally split into 2 or more doses;

(iii) optionally combining the treatment in (ii) with administration of a neurotransmission modifying compound which is a modifier of the activity of acetylcholine or glutamate neurotransmitters, such as an AChEI and\or memantine.

These different phases of the regimen will typically immediately follow each other.

Also provided herein are methods of prophylactic treatment of neurodegenerative disorders of protein aggregation.

These aspects and embodiments will now be described in more detail:

Methylthioninium Moiety

| Structure | |
|---|---|
| IUPAC | N3,N3,N7,N7-tetramethyl-10H-phenothiazine-3,7-diamine |
| Composition | Formula Weight: 285.41(1) |
| | Exact Mass : 285.1299683(1) |
| | Formula : $C_{16}H_{19}N_3S$ |
| | Composition : C 67.33% H 6.71% |
| | N 14.72% S 11.23% |
| Synonym | leucomethylthioninium (LMT) |

The MT-containing compounds used in the present invention contain an MT moiety as active ingredient in reduced form (termed "LMT"). The LMT moiety per se described above is not stable. It will therefore be administered as an LMT compound—for example an LMT salts.

LMT-containing compounds will generally be stabilised, for example by the presence of one or more protic acids e.g. two protic acids.

The MT content of such salts can be readily calculated by those skilled in the art based on the molecular weight of the compound, and the molecular weight of the MT moiety. Examples of such calculations are given herein.

LMT Compounds

Preferably the LMT compound is an "LMTX" compound of the type described in WO2007/110627 or WO2012/107706.

Thus the compound may be selected from compounds of the following formula, or hydrates or solvates thereof:

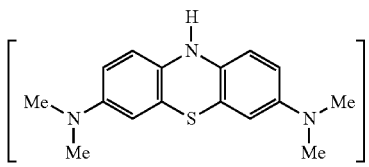

p(H$_n$A)
p(H$_n$B)
Options:
p = 1, 2
q = 0, 1
n = 1, 2
(p + q) × n = 2

Each of H$_n$A and H$_n$B (where present) are protic acids which may be the same or different.

By "protic acid" is meant a proton (H$^+$) donor in aqueous solution. Within the protic acid A$^-$ or B$^-$ is therefore a conjugate base. Protic acids therefore have a pH of less than 7 in water (that is the concentration of hydronium ions is greater than $10^{-7}$ moles per litre).

In one embodiment the salt is a mixed salt that has the following formula, where HA and HB are different mono-protic acids:

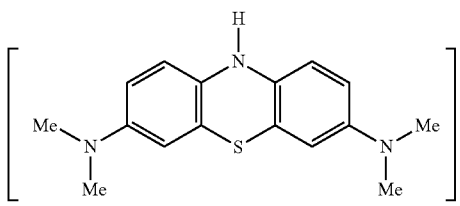

HA
HB
when:
p = 1
q = 1
n = 1
(1 + 1) × 1 = 2

However preferably the salt is not a mixed salt, and has the following formula:

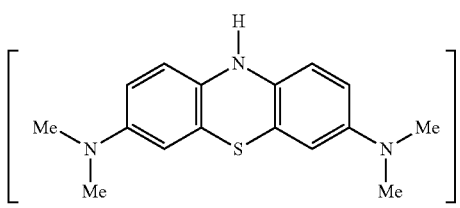

p(H$_n$X)
when:
p = 1, 2
n = 1, 2
p × n = 2 wherein each of H$_n$X is a protic acid, such as a di-protic acid or mono-protic acid.

In one embodiment the salt has the following formula, where H$_2$A is a di-protic acid:

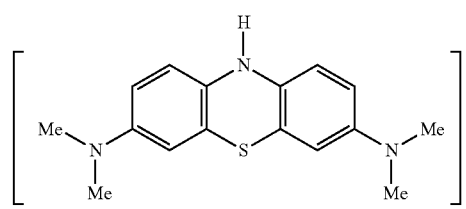

H$_2$A
when:
p = 1
q = 0
n = 2
(1 + 0) × 2 = 2

Preferably the salt has the following formula which is a bis monoprotic acid:

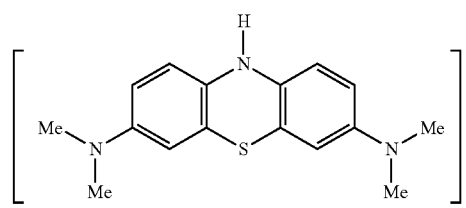

2(HA)
when:
p = 2
q = 0
n = 1
(2 + 0) × 1 = 2

Examples of protic acids which may be present in the LMTX compounds used herein include:

Inorganic acids: hydrohalide acids (e.g., HCl, HBr), nitric acid (HNO$_3$), sulphuric acid (H$_2$SO$_4$)

Organic acids: carbonic acid (H$_2$CO$_3$), acetic acid (CH$_3$COOH), methanesulfonic acid, 1,2-ethanedisulfonic acid, ethansulfonic acid, Naphthalenedisulfonic acid, p-toluenesulfonic acid, Preferred acids are monoprotic acid, and the salt is a bis(monoprotic acid) salt.

A preferred MT compound is LMTM:

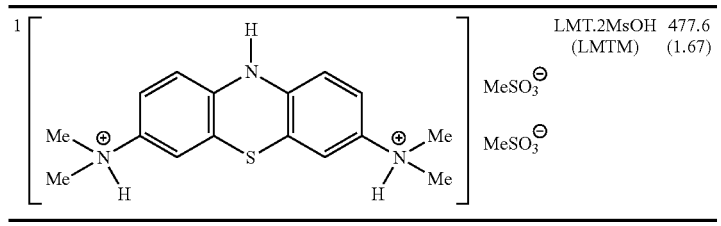

LMT.2MsOH 477.6
(LMTM) (1.67)

Weight Factors

The anhydrous salt has a molecular weight of around 477.6. Based on a molecular weight of 285.1 for the LMT core, the weight factor for using this MT compound in the invention is 1.67. By "weight factor" is meant the relative weight of the pure MT-containing compound vs. the weight of MT which it contains.

Other weight factors can be calculated for example MT compounds herein, and the corresponding dosage ranges can be calculated therefrom.

Therefore the invention embraces a total daily dose of around 34 to 67, 34 to 100, 34 to 134, or 34 to 167 mg/day of LMTM.

Other example LMTX compounds are as follows. Their molecular weight (anhydrous) and weight factor is also shown:

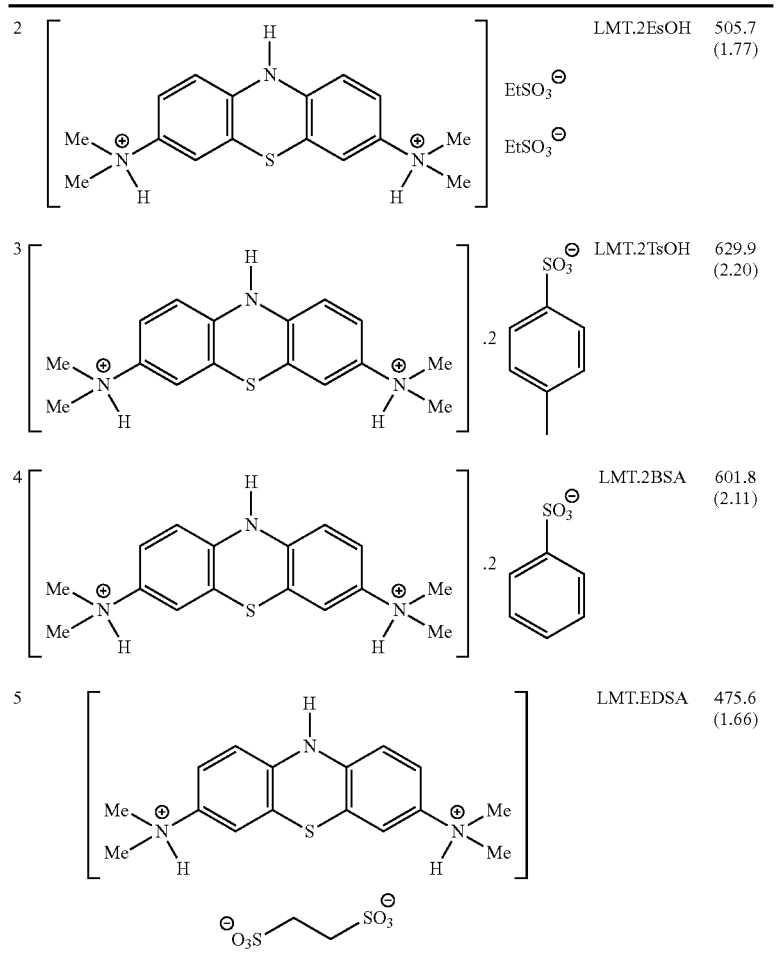

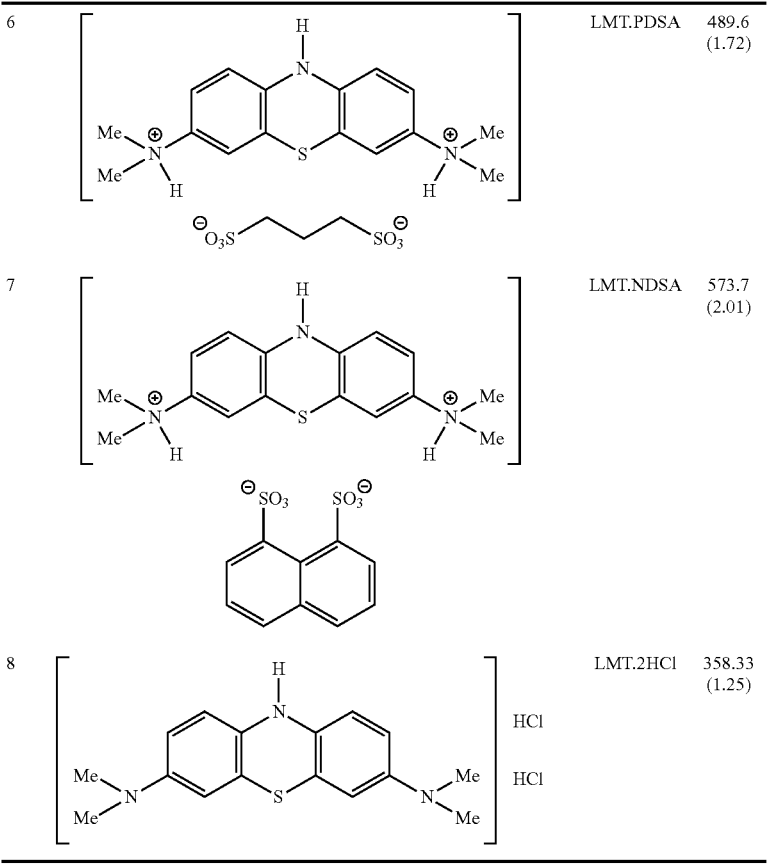

The dosages described herein with respect to MT thus apply mutatis mutandis for these MT-containing compounds, as adjusted for their molecular weight.

Accumulation Factors

As will be appreciated by those skilled in the art, for a given daily dosage, more frequent dosing can lead to greater accumulation of a drug.

Therefore in certain embodiments of the claimed invention, the total daily dosed amount of MT compound may be relatively lower, when dosing more frequently (e.g. twice a day [bid] or three times a day [tid]), or higher when dosing once a day [qd].

Treatment and Prophylaxis

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition.

The term "therapeutically-effective amount," as used herein, pertains to that amount of a compound of the invention, or a material, composition or dosage from comprising said compound, which is effective for producing some desired therapeutic effect, commensurate with a reasonable benefit/risk ratio, when administered in accordance with a desired treatment regimen. The present inventors have demonstrated that a therapeutically-effective amount of an MT compound in respect of the diseases of the invention can be much lower than was hitherto understood in the art.

The invention also embraces treatment as a prophylactic measure. Thus the invention also provides a method of prophylaxis of a neurodegenerative disorder (e.g. of protein aggregation) in a subject, which method comprises orally administering to said patient an MT-containing compound, wherein said administration provides a total of between 20 or 21 and 40 mg, 20.5 and 60, 20.5 and 80, or 20.5 and 99 or 100 mg of MT to the subject per day, optionally split into 2 or more doses, as described above.

The term "prophylactically effective amount," as used herein, pertains to that amount of a compound of the invention, or a material, composition or dosage from comprising said compound, which is effective for producing some desired prophylactic effect, commensurate with a reasonable benefit/risk ratio, when administered in accordance with a desired treatment regimen.

"Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

Combination Treatments and Monotherapy

The term "treatment" includes "combination" treatments and therapies, in which two or more treatments or therapies for the same neurodegenerative disorder are combined, for example, sequentially or simultaneously. These may be symptomatic or disease modifying treatments.

The particular combination would be at the discretion of the physician.

In combination treatments, the agents (i.e., an MT compound as described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

An example of a combination treatment of the invention (for AD) would be an agent which is an MT-containing compound at the specified dosage in combination with an agent which is an inhibitor of the processing of amyloid precursor protein to beta-amyloid (e.g., an inhibitor of amyloid precursor protein processing that leads to enhanced generation of beta-amyloid).

The invention also allows for co-administration of either or both of: an acetylcholinesterase inhibitor or an N-methyl-D-aspartate receptor antagonist.

As described herein, in relation to combination therapies, the invention provides methods of enhancing the therapeutic effectiveness of a first compound which is an MT compound at a dose described herein for the treatment of a neurodegenerative disorder in a subject, the method comprising administering to the subject a second compound, which second compound directly modifies synaptic neurotransmission in the brain of the subject (for example an acetylcholinesterase inhibitor or an N-methyl-D-aspartate receptor antagonist).

The invention further provides a first compound which is an MT compound at a dose described herein in a method of treatment of a neurodegenerative disorder in a subject in a treatment regimen which additionally comprises treatment with a second compound, which second compound directly modifies synaptic neurotransmission in the brain of the subject.

The invention further provides use of a compound which directly modifies synaptic neurotransmission in the brain of a subject to enhance the therapeutic effectiveness of an MT compound at a dose described herein in the treatment of a neurodegenerative disorder in the subject.

The invention further provides an MT compound at a dose described herein and a compound which directly modifies synaptic neurotransmission in the brain for use in a combination methods of the invention.

The invention further provides a compound which directly modifies synaptic neurotransmission in the brain of the subject for use in a method of enhancing the therapeutic effectiveness of an MT compound at a dose described herein in the treatment of a neurodegenerative disorder in a subject.

The invention further provides use of a first compound which is an MT compound at a dose described herein in combination with a second compound, which second compound directly modifies synaptic neurotransmission in the brain of the subject, in the manufacture of a medicament for treatment of a neurodegenerative disorder.

The invention further provides use of an MT compound at a dose described herein in the manufacture of a medicament for use in the treatment of a neurodegenerative disorder syndrome in a subject, which treatment further comprises use of a second compound, which second compound directly modifies synaptic neurotransmission in the brain of the subject.

The invention further provides use of a compound which directly modifies synaptic neurotransmission in the brain, in the manufacture of a medicament for use in the treatment of a neurodegenerative disorder in a subject, which treatment further comprises use of an MT compound at a dose described herein and the compound which directly modifies synaptic neurotransmission in the brain of the subject.

In other embodiments the treatment is a "monotherapy", which is to say that the MT-containing compound is not used in combination (within the meaning discussed above) with another active agent for treating the same neurodegenerative disorder of protein aggregation in the subject.

Duration of Treatment

For treatment of the neurodegenerative disorder described herein, a treatment regimen based on the low dose MT compounds will preferably extend over a sustained period of time. The particular duration would be at the discretion of the physician.

For example, the duration of treatment may be:

At least 1, 2, 3, 4, 5, 6, 7, 8, 9, 10, 11, 12 months, or longer.

At least 2, 3, 4, 5 years, or longer.

Between 6 and 12 months.

Between 1 and 5 years.

For prophylaxis, the treatment may be ongoing.

In all cases the treatment duration will generally be subject to advice and review of the physician.

Desired Endpoints

The methods (dosage regimens) described herein may be utilised to achieve a specific particular therapeutic or prophylactic outcome. That specific outcome may be quantified according to a scale relevant to the neurodegenerative disorder. Such scales may for example measure change of cognitive, functional or physical criteria relevant to the disorder. The Examples herein illustrate appropriate scales by which the effect of the dosage regimen may be confirmed, as compared to placebo or other reference point (e.g. different dosage regimens). These include the Alzheimer's Disease Assessment Scale—cognitive subscale (ADAS-cog) used in relation to AD, and the Addenbrooke's Cognitive Examination—revised (ACE-R) used in relation to bvFTD.

Thus, by way of non-limiting example, in one embodiment wherein the treatment is an AD treatment achieves (or is for achieving) a reduction in cognitive decline in the subject, which is optionally an at least 1, 2, 2.5, 3, 4, 5 or 6-point reduction in decline on the 11-item Alzheimer's Disease Assessment Scale-cognitive subscale (ADAS-cog) over a 65-week period compared to a corresponding control or control population not being treated according to the invention.

In one embodiment the treatment is a bfFTD treatment which achieves (or is for achieving): (i) a reduction in cognitive decline in the subject, which is optionally an at least 1, 2, 3, 4, 5, 6, 7 or 8-point reduction in decline on the Addenbrooke's Cognitive Examination—revised (ACE-R) scale over a 52-week period; or (ii) a reduction in functional decline in the subject, which is optionally an at least 1, 2, 3, 4, 5, or 6 point reduction in decline on the Functional Activities Questionnaire (FAQ) over a 52-week period, in each case compared to a corresponding control or control population not being treated according to the invention.

Pharmaceutical Dosage Forms

The MT compound of the invention, or pharmaceutical composition comprising it, is administered to a subject/patient orally.

Typically in the practice of the invention the compound will be administered as a composition comprising the compound, and a pharmaceutically acceptable carrier or diluent.

In some embodiments, the composition is a pharmaceutical composition (e.g., formulation, preparation, medicament) comprising a compound as described herein, and a pharmaceutically acceptable carrier, diluent, or excipient.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

In some embodiments, the composition is a pharmaceutical composition comprising at least one compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In some embodiments, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, New York, USA), Remington's Pharmaceutical Sciences, 20th edition, pub. Lippincott, Williams & Wilkins, 2000; and Handbook of Pharmaceutical Excipients, 2nd edition, 1994.

One aspect of the present invention pertains to a dosage unit (e.g., a pharmaceutical tablet or capsule) comprising an MT compound as described herein (e.g., obtained by, or obtainable by, a method as described herein; having a purity as described herein; etc.), and a pharmaceutically acceptable carrier, diluent, or excipient.

The "MT compound", although present in relatively low amount, is the active agent of the dosage unit, which is to say is intended to have the therapeutic or prophylactic effect in respect of a neurodegenerative disorder of protein aggregation. Rather, the other ingredients in the dosage unit will be therapeutically inactive e.g. carriers, diluents, or excipients. Thus, preferably, there will be no other active ingredient in the dosage unit, no other agent intended to have a therapeutic or prophylactic effect in respect of a disorder for which the dosage unit is intended to be used.

In some embodiments, the dosage unit is a tablet.

In some embodiments, the dosage unit is a capsule.

In some embodiments, said capsules are gelatine capsules.

In some embodiments, said capsules are HPMC (hydroxypropylmethylcellulose) capsules.

The appropriate quantity of MT in the composition will depend on how often it is taken by the subject per day.

An example dosage unit may contain 8 to 32 mg of MT.

A further example dosage unit may contain 8 to 16 mg of MT.

In some embodiments, the amount is about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 mg of MT.

Using the weight factors described or explained herein, one skilled in the art can select appropriate amounts of an MT-containing compound to use in oral formulations.

As explained above, the MT weight factor for LMTM is 1.67. Since it is convenient to use unitary or simple fractional amounts of active ingredients, non-limiting example LMTM dosage units may include 13.4, 15, 16.7 mg etc.

In one embodiment there is provided a dosage unit pharmaceutical composition which comprises about 34, 67 or 100 mg of LMTM.

Nutraceutical Compositions

The MT-containing compositions utilised in the invention may be present in a "nutraceutical composition" containing an appropriate dose of MT compound, as described herein, in combination with one or more nutrients in an edible form (for example an oral dosage form).

The novel nutraceutical compositions of the invention can find use as supplements to food and beverages, and as pharmaceutical compositions. These nutraceutical compositions, having the MT compound dose described herein, form another aspect of the invention per se.

"Nutrients" as used herein refers to the components of nutraceutical compositions that serve a biochemical and/or physiological role in the human or animal body. "Nutrients" includes such substances as vitamins, minerals, trace elements, micronutrients, antioxidants and the like, as well as other bioactive materials, such as enzymes, or compounds biosynthetically produced by human or animal enzymes; as well as herbs and herbal extracts; fatty acids, amino acids and derivatives thereof.

"Edible form" denotes a composition that can be ingested directly or converted to an ingestible form, such as, by dissolving in water.

Alternatively, the nutraceutical composition can be in the form of a food or drink, such as a defined portion of a foodstuff (which term includes both food and drink) supplemented with the defined dosage of MT compound. These foodstuffs will typically comprise one or more of a fat, a protein, or a carbohydrate.

The term "nutraceutical" as used herein denotes a usefulness in both the nutritional and pharmaceutical field of application, and the disclosure herein relating to pharmaceutical dosage forms applies mutatis mutandis to the nutraceutical compositions.

Oral dosage forms particularly suitable for nutraceutical compositions are well known in the art and described in more detail elsewhere herein. They include powders, capsules, pills, tablets, caplets, gelcaps, and defined portions of edible food items. Liquid forms include solutions or suspensions. General examples of dosage forms and nutraceutical forms are given, for example in WO2010/078659.

Some examples of nutrients useful in the compositions of the present invention are as follows. Any combination of these nutrients is envisaged by the present invention:

Vitamins

It is reported that B-vitamin supplementation (folic acid [folate, vitamin $B_9$], vitamin $B_{12}$, vitamin $B_6$) can slow the atrophy of specific brain regions that are a key component of the AD process and that are associated with cognitive decline. This is particularly the case for elderly subjects with high homocysteine levels (Douaud, Gwenaëlle, et al. "Preventing Alzheimer's disease-related gray matter atrophy by B-vitamin treatment." Proceedings of the National Academy of Sciences 110.23 (2013): 9523-9528; see also Quadri, Pierluigi, et al. "Homocysteine, folate, and vitamin $B_{12}$ in mild cognitive impairment, Alzheimer disease, and vascular dementia." *The American journal of clinical nutrition* 80.1

(2004): 114-122; Rosenberg I H, Miller J W. Nutritional factors in physical and cognitive functions of elderly people. The American Journal of Clinical Nutrition. 1992 Jun. 1; 55(6):1237S-1243S.).

It has been suggested that, along with other antioxidants (see below), vitamin C may have utility in protecting neural tissue, as well as potentially decreasing β-amyloid generation and acetylcholinesterase activity and prevents endothelial dysfunction by regulating nitric oxide (see e.g. Heo J H, Hyon-Lee, Lee K M. The possible role of antioxidant vitamin C in Alzheimer's disease treatment and prevention. American Journal of Alzheimer's Disease & Other Dementias. 2013 March; 28(2):120-5).

It has also been suggested that Vitamin E supplementation may have a role to play in AD treatment (see e.g. Mangialasche, Francesca, et al. "Serum levels of vitamin E forms and risk of cognitive impairment in a Finnish cohort of older adults." Experimental Gerontology 48.12 (2013): 1428-1435).

Micronutrients, Antioxidants

Micronutrients or antioxidants, such as polyphenols, have been reported to have benefits in relation to protection or treatment of age-related diseases including neurodegenerative ones, particularly cognitive impairment and AD.

Micronutrients and\or antioxidants which may be utilised in the nutraceutical compositions described herein include the flavonoids shown in the Table below (reproduced from Mecocci, Patrizia, et al. "Nutraceuticals in cognitive impairment and Alzheimer's disease." *Frontiers in Pharmacology* 5:147 (2014)):

Flavonoid Chemical Subgroups and Relative Food Sources:

| Groups | Molecules | Food source |
| --- | --- | --- |
| FLAVANOLS | Catechin, epicatechin, epigallocathechin, epigallocatechin gallate (EGCG) | Cocoa and chocolate, green tea, grapes |
| FLAVONOLS | Kaempferol, quercetin | Onions, apples, green tea, capers, leeks, broccoli |
| FLAVONES | Luteolin, apigenin | Celery, parsley, rosemary |
| ISOFLAVONES | Daidzein, genistein | Soy |
| FLAVANONES | Hesperetin, naringenin | Citrus fruit, tomatoes |
| ANTHOCYANIDINS | Pelargonidin, cyanidine, malvidin | Berry fruits, red wine |

Other micronutrients having potential utility in relation to protection or treatment of age-related diseases, and described by Mecocci et al include:
  Non-flavonoid polyphenols: resveratrol and curcumin,
  Carotenoids: lycopene, lutein, zeaxanthin, β-cryptoxanthin, α-carotene, and the most prominent carotenoid, β-carotene,
  Crocin (the main chemical compound identified in saffron),
  Diterpenes: for example carnosic and rosmarinic acids are two of the most important antioxidant compounds in rosemary.

Herbs and Plant Extracts

In addition to the plants described or cross-referenced above in relation to micronutrients and antioxidants, other plant extracts and herbs are reported to have benefit in CNS disorders—see Kumar, Vikas. "Potential medicinal plants for CNS disorders: an overview." *Phytotherapy Research* 20.12 (2006): 1023-1035. These include *Ginkgo biloba*, *Hypericum perforatum* (St John's wort), *Piper methysticum* Forst. (Family Piperaceae) also called kava kava, *Valeriana officinalis* L. (Valerian), *Bacopa monniera* (which in India is locally known as Brahmi or Jalanimba), *Convolvulus pluricaulis* (also known as Shankhpushpi or shankapushpi)

Oils and Fats

It is reported that ω-3 poyunsaturated fatty acid (PUFA), for example, may be a promising tool for preventing age-related brain deterioration. Sources of PUFA such as (docosahexaenoic acid (DHA, 22:6) and eicosapentenoic acid (EPA, 20:5) include fish oils (Denis, I., et al. "Omega-3 fatty acids and brain resistance to ageing and stress: body of evidence and possible mechanisms." *Ageing Research Reviews* 12.2 (2013): 579-594.)

Subjects, Patients and Patient Groups

The teachings of the invention may be applied to a subject/patient which is an animal, a mammal, a placental mammal, a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), a monotreme (e.g. platypus), an ape (e.g., gorilla, chimpanzee, orangutan, gibbon), or a human.

In preferred embodiments, the subject/patient is a human who has been diagnosed as having one of the cognitive or CNS disorders described herein, or (for prophylactic treatment) assessed as being susceptible to one of the neurodegenerative disorders of protein aggregation (e.g. cognitive or CNS disorder) described herein—for example based on familial or genetic or other data.

The patient may be an adult human, and the population based dosages described herein are premised on that basis (typical weight 50 to 70 kg). If desired, corresponding dosages may be utilised for subjects falling outside of this range by using a subject weight factor whereby the subject weight is divided by 60 kg to provide the multiplicative factor for that individual subject.

Thus, for example, for diagnosis of AD, and assessment of severity, the initial selection of a patient may involve any one or more of: rigorous evaluation by experienced clinician; exclusion of non-AD diagnosis as far as possible by supplementary laboratory and other investigations; objective evaluation of level of cognitive function using neuropathologically validated battery.

Diagnosis of AD and other disorders described herein can be performed by physicians by methods well known to those skilled in the art.

As explained herein, MT compounds of an appropriate dosage may demonstrate benefit (for example in relation to slower rate of decline as measured by ADAS-Cog) even in subjects or patient populations being treated in respect of AD using an acetylcholinesterase inhibitor or an N-methyl-D-aspartate receptor antagonist.

Examples of acetylcholinesterase inhibitors include Donepezil (Aricept™), Rivastigmine (Exelon™) or Galantamine (Reminyl™). An examples of an NMDA receptor antagonist is Memantine (Ebixa™, Namenda™). Examples of the total daily dose of these neurotransmission modifying compound is as follows: Donepezil: between 5 and 23 mg; Rivastigmine: between 3 and 12 mg; Galantamine: between 4 and 24 mg; Memantine: between 5 and 20 mg.

Thus in one embodiment of the present invention provides a method of treatment (or prophylaxis) of AD in a subject, which method comprises orally administering to said subject a methylthioninium (MT) containing compound in the dosage described herein, wherein said treatment further comprises administration of either or both of an acetylcholinesterase inhibitor or an N-methyl-D-aspartate receptor antagonist.

In other embodiments the AD subject or patient group may be entirely nave to these other treatments, and have not historically received one or both of an acetylcholinesterase inhibitor or an N-methyl-D-aspartate receptor antagonist.

Alternatively the AD subject or patient group may have historically received one or both of them, but ceased that medication at least 1, 2, 3, 4, 5, 6, 7 days, or 2, 3, 4, 5, 6, 7, 8, 12, or 16 weeks, or more preferably at least 1, 2, 3, 4, 5 or 6 months etc. prior to treatment with an MT compound according to the present invention.

Any aspect of the present invention may include the active step of selecting the AD subject or patient group according to these criteria, or selecting an AD subject or patient group who is or are receiving treatment with either or both an acetylcholinesterase inhibitor or an N-methyl-D-aspartate receptor antagonist, and discontinuing that treatment (instructing the subject or patient group to discontinue that treatment) prior to treatment with an MT compound according to the present invention.

Such treatment may optionally be started or re-started after commencement of treatment with the MT compound.

Labels, Instructions and Kits of Parts

The unit dosage compositions described herein (e.g. a low dose MT-containing compound plus optionally other ingredients, or MT composition more generally for treatment in AD) may be provided in a labelled packet along with instructions for their use.

In one embodiment, the pack is a bottle, such as are well known in the pharmaceutical art. A typical bottle may be made from pharmacopoeial grade HDPE (High-Density Polyethylene) with a childproof, HDPE pushlock closure and contain silica gel desiccant, which is present in sachets or canisters. The bottle itself may comprise a label, and be packaged in a cardboard container with instructions for us and optionally a further copy of the label.

In one embodiment, the pack or packet is a blister pack (preferably one having aluminium cavity and aluminium foil) which is thus substantially moisture-impervious. In this case the pack may be packaged in a cardboard container with instructions for us and label on the container.

Said label or instructions may provide information regarding the neurodegenerative disorders of protein aggregation (e.g. cognitive or CNS disorder) for which the medication is intended.

Where the medication is indicated for AD, said label or instructions may provide information instructing the user that the compositions should not be used in conjunction with any of: an acetylcholinesterase inhibitor or an N-methyl-D-aspartate receptor antagonist.

Said label or instructions may provide information regarding the maximum permitted daily dosage of the compositions as described herein—for example based on once daily, b.i.d., or t.i.d.

Said label or instructions may provide information regarding the suggested duration of treatment, as described herein.

Reversing and/or Inhibiting the Aggregation of a Protein

One aspect of the invention is the use of an MT compound or composition as described herein, to regulate (e.g., to reverse and/or inhibit) the aggregation of a protein, for example, aggregation of a protein associated with a neurodegenerative disease and/or clinical dementia. The aggregation will be associated with a disease state as discussed below.

Similarly, one aspect of the invention pertains to a method of regulating (e.g., reversing and/or inhibiting) the aggregation of a protein in the brain of a mammal, which aggregation is associated with a disease state as described herein, the treatment comprising the step of administering to said mammal in need of said treatment, a prophylactically or therapeutically effective amount of an MT compound or composition as described herein, that is an inhibitor of said aggregation.

Disease conditions treatable via the present invention are discussed in more detail below.

Methods of Treatment

Another aspect of the present invention, as explained above, pertains to a method of treatment comprising administering to a patient in need of treatment a prophylactically or therapeutically effective amount of a compound as described herein, preferably in the form of a pharmaceutical composition.

Use in Methods of Therapy

Another aspect of the present invention pertains to a compound or composition as described herein, for use in a method of treatment (e.g., of a disease condition) of the human or animal body by therapy.

Use in the Manufacture of Medicaments

Another aspect of the present invention pertains to use of an MT compound or composition as described herein, in the manufacture of a medicament for use in treatment (e.g., of a disease condition).

In some embodiments, the medicament is a composition e.g. a low-dose unit dose composition as described herein.

Neurodegenerative Disorders of Protein Aggregation

The findings described herein have implications for the dosing of MT compounds in different diseases. In particular, adopting a dosing regimen which maximises the proportion of subjects in which the MT concentration will exceed the Cmax threshold, while nevertheless maintaining a relatively low dose so as to maintain a desirable clinical profile, can be applied in the treatment or prophylaxis of various diseases of protein aggregation in which MT has been described as being effective.

Thus, in some embodiments, the disease condition is a disease of protein aggregation, and, for example, the treatment is with an amount of a compound or composition as described herein, sufficient to inhibit the aggregation of the protein associated with said disease condition.

The following Table lists various disease-associated aggregating proteins and the corresponding neurodegenerative disease of protein aggregation. The use of the dosage regimens of the invention in respect of these proteins or diseases is encompassed by the present invention.

| Protein | Disease | Aggregating domain and/or mutations | Fibril subunit size (kDa) | Reference |
| --- | --- | --- | --- | --- |
| Prion protein | Prion diseases | Inherited and sporadic forms | 27 | Prusiner (1998) |
| | (CJD, nvCJD, Fatal familial insomnia, Gerstmann-Straussler-Scheinker syndrome, Kuril) | PrP-27-30; many mutations. | 27 | Prusiner (1998) |

-continued

| Protein | Disease | Aggregating domain and/or mutations | Fibril subunit size (kDa) | Reference |
|---|---|---|---|---|
| Tau protein | Alzheimer's disease, Down's syndrome, FTDP-17, CBD, post-encephalitic parkinsonism, Pick's disease, parkinsonism with dementia complex of Guam | Fibrillogenic domains: 113-120, 178-191, 202-218. | | Gasset et al. (1992) |
| | | Inherited and sporadic forms | 10-12 | Wischik et al. (1988) |
| | | Truncated tau (tubulin-binding domain) 297-391. | 10-12 | Wischik et al. (1988) |
| | | Mutations in tau in FTDP-17. | | Hutton et al. (1998) |
| | | Many mutations in presenilin proteins. | | Czech et al. (2000) |
| Amyloid β-protein | Alzheimer's disease, Down's syndrome | Inherited and sporadic forms | 4 | Glenner & Wong, (1984) |
| | | Amyloid β-protein; 1-42(3). Mutations in APP in rare families. | 4 | Glenner & Wong, (1984) Goate et al. (1991) |
| Huntingtin | Huntington's disease | N-termini of protein with expanded glutamine repeats. | 40 | DiFiglia et al. (1997) |
| Ataxin) | Spinocerebellar ataxias (SCA1, 2, 3, 7) | Proteins with expanded glutamine repeats. | | Paulson et al. (1999) |
| Atrophin | Dentatorubropallidoluysian atrophy (DRPLA) | Proteins with expanded glutamine repeats. | | Paulson et al. (1999) |
| Androgen receptor | Spinal and bulbar muscular atrophy | Proteins with expanded glutamine repeats. | | Paulson et al. (1999) |
| Neuroserpin | Familial encephalopathy with neuronal inclusion bodies (FENIB) | Neuroserpin; S49P, S52R. | 57 | Davis et al. (1999) |
| α-Synuclein | Parkinson's disease, dementia with Lewy bodies, multiple system atrophy | Inherited and sporadic forms | 19 | Spillantini et al. (1998) also PCT/GB2007/001105 |
| | | A53T, A30P in rare autosomal-dominant PD families. | | Polymeropoulos et al. (1997) |
| TDP-43 | FTLD-TDP | Several TDP-43 mutations | 10-43 | Mackenzie et al. (2010) |
| | Amyotrophic lateral sclerosis | Several TDP-43 mutations | 10-43 | Mackenzie et al. (2010) |
| Cystatin C | Hereditary cerebral angiopathy (Icelandic) | Cystatin C less 10 residues; L68Q. | 12-13 | Abrahamson et al. (1992) |
| Superoxide dismutase 1 | Amyotrophic lateral sclerosis | SOD1 mutations. | 16 | Shibata et al. (1996) |

As described in WO 02/055720, WO2007/110630, and WO2007/110627, diaminophenothiazines have utility in the inhibition of such protein aggregating diseases.

Thus it will be appreciated that, except where context requires otherwise, description of embodiments with respect to tau protein or tau-like proteins (e.g., MAP2; see below), should be taken as applying equally to the other proteins discussed herein (e.g., TDP-43, β-amyloid, synuclein, prion, etc.) or other proteins which may initiate or undergo a similar pathological aggregation by virtue of conformational change in a domain critical for propagation of the aggregation, or which imparts proteolytic stability to the aggregate thus formed (see, e.g., the article by Wischik et al. in "Neurobiology of Alzheimer's Disease", 2nd Edition, 2000, Eds. Dawbarn, D. and Allen, S. J., The Molecular and Cellular Neurobiology Series, Bios Scientific Publishers, Oxford). All such proteins may be referred to herein as "aggregating disease proteins."

Likewise, where mention is made herein of "tau-tau aggregation", or the like, this may also be taken to be applicable to other "aggregating-protein aggregation", such as β-amyloid aggregation, prion aggregation, synuclein aggregation, etc. The same applies for "tau proteolytic degradation" etc.

Preferred Aggregating Disease Target Proteins

Preferred embodiments of the invention are based on tau protein. The term "tau protein," as used herein, refers generally to any protein of the tau protein family. Tau proteins are characterised as being one among a larger number of protein families which co-purify with microtubules during repeated cycles of assembly and disassembly (see, e.g., Shelanski et al., 1973, Proc. Natl. Acad. Sci. USA, Vol. 70, pp. 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

MAP2 is the predominant microtubule-associated protein in the somatodendritic compartment (see, e.g., Matus, A., in "Microtubules" [Hyams and Lloyd, Eds.] pp. 155-166, John Wiley and Sons, New York, USA). MAP2 isoforms are almost identical to tau protein in the tandem repeat region, but differ substantially both in the sequence and extent of the N-terminal domain (see, e.g., Kindler and Garner, 1994, Mol. Brain Res., Vol. 26, pp. 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation, and so on.

In some embodiments, the protein is tau protein.

In some embodiments, the protein is a synuclein, e.g., α- or β-synuclein.

In some embodiments, the protein is TDP-43.

TAR DNA-Binding Protein 43 (TDP-43) is a 414 amino acid protein encoded by TARDBP on chromosome 1p36.2. The protein is highly conserved, widely expressed, and predominantly localised to the nucleus but can shuttle between the nucleus and cytoplasm (Mackenzie et al 2010). It is involved in transcription and splicing regulation and may have roles in other processes, such as: microRNA processing, apoptosis, cell division, stabilisation of messenger RNA, regulation of neuronal plasticity and maintenance of dendritic integrity. Furthermore, since 2006 a substantial body of evidence has accumulated in support of the TDP-43 toxic gain of function hypothesis in amyotrophic lateral sclerosis (ALS). TDP-43 is an inherently aggregation-prone protein and aggregates formed in vitro are ultrastructurally similar to the TDP-43 deposits seen in degenerating neurones in ALS patients (Johnson et al 2009). Johnson et al (2008) showed that when TDP-43 is overexpressed in a yeast model only the aggregated form is toxic. Several in vitro studies have also shown that C-terminal fragments of TDP-43 are more likely than full-length TDP-43 to form insoluble cytoplasmic aggregates that become ubiquitinated, and toxic to cells (Arai et al 2010; Igaz et al 2009; Nonaka et al 2009; Zhang et al 2009). Though Nonaka et al (2009) suggested that these cytoplasmic aggregates bind the endogenous full-length protein depleting it from the nucleus, Zhang et al (2009) found retention of normal nuclear expression, suggesting a purely toxic effect for the aggregates. Yang et al (2010) have described the capture of full-length TDP-43 within aggregates of C- and N-terminal fragments of TDP-43 in NSC34 motor neurons in culture. Neurite outgrowth, impaired as a result of the presence of such truncated fragments, could be rescued by overexpression of the full-length protein. Although the role of neurite outgrowth in vivo has not been established, this model would support the suggestion made by Nonaka and colleagues for a role of TDP-43 aggregation in ALS pathogenesis.

Mutant TDP-43 expression in cell cultures has repeatedly been reported to result in increased generation of C-terminal fragments, with even greater cytoplasmic aggregation and toxic effects than the wild-type protein (Kabashi et al 2008; Sreedharan et al 2008; Johnson et al 2009; Nonaka et al 2009; Arai et al 2010; Barmarda et al 2010; Kabashi et al 2010).

Where the protein is tau protein, in some embodiments of the present invention, there is provided a method of inhibiting production of protein aggregates (e.g. in the form of paired helical filaments (PHFs), optionally in neurofibrillary tangles (NFTs) in the brain of a mammal, the treatment being as described above.

Preferred Indications—Diseases of Protein Aggregation

In one embodiment the present invention is used for the treatment of Alzheimer's disease (AD)—for example mild, moderate or severe AD.

Notably it is not only Alzheimer's disease (AD) in which tau protein (and aberrant function or processing thereof) may play a role. The pathogenesis of neurodegenerative disorders such as Pick's disease and progressive supranuclear palsy (PSP) appears to correlate with an accumulation of pathological truncated tau aggregates in the dentate gyrus and stellate pyramidal cells of the neocortex, respectively. Other dementias include fronto-temporal dementia (FTD); FTD with parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see, e.g., the article by Wischik et al. in "Neurobiology of Alzheimer's Disease", 2nd Edition, 2000, Eds. Dawbarn, D. and Allen, S. J., The Molecular and Cellular Neurobiology Series, Bios Scientific Publishers, Oxford; especially Table 5.1). All of these diseases, which are characterized primarily or partially by abnormal tau aggregation, are referred to herein as "tauopathies".

Thus, in some embodiments, the disease condition is a tauopathy.

In some embodiments, the disease condition is a neurodegenerative tauopathy.

In some embodiments, the disease condition is selected from Alzheimer's disease (AD), Pick's disease, progressive supranuclear palsy (PSP), fronto temporal dementia (FTD), FTD with parkinsonism linked to chromosome 17 (FTDP 17), frontotemporal lobar degeneration (FTLD) syndromes; disinhibition-dementia-parkinsonism-amyotrophy complex (DDPAC), pallido-ponto-nigral degeneration (PPND), Guam-ALS syndrome, pallido nigro luysian degeneration (PNLD), cortico-basal degeneration (CBD), dementia with argyrophilic grains (AgD), dementia pugilistica (DP) or chronic traumatic encephalopathy (CTE), Down's syndrome (DS), dementia with Lewy bodies (DLB), subacute sclerosing panencephalitis (SSPE), MCI, Niemann-Pick disease, type C (NPC), Sanfilippo syndrome type B (mucopolysaccharidosis III B), or myotonic dystrophies (DM), DM1 or DM2, or chronic traumatic encephalopathy (CTE).

In some embodiments, the disease condition is a lysosomal storage disorder with tau pathology. NPC is caused by mutations in the gene NPC1, which affects cholesterol metabolism (Love et al 1995) and Sanfilippo syndrome type B is caused by a mutation in the gene NAGLU, in which there is lysosomal accumulation of heparin sulphate (Ohmi et al. 2009). In these lysosomal storage disorders, tau pathology is observed and its treatment may decrease the progression of the disease. Other lysosomal storage disorders may also be characterised by accumulation of tau.

Use of phenothiazine diammonium salts in the treatment of Parkinson's disease and MCI is described in more detail in PCT/GB2007/001105 and PCT/GB2008/002066.

In some embodiments, the disease condition is Parkinson's disease, MCI, or Alzheimer's disease.

In some embodiments, the disease condition is Huntington's disease or other polyglutamine disorder such as spinal bulbar muscular atrophy (or Kennedy disease), and dentatorubropallidoluysian atrophy and various spinocerebellar ataxias.

In some embodiments, the disease condition is an FTLD syndrome (which may for example be a tauopathy or TDP-43 proteinopathy, see below).

In some embodiments, the disease condition is PSP or ALS.

TDP-43 proteinopathies include amyotrophic lateral sclerosis (ALS; ALS-TDP) and frontotemporal lobar degeneration (FTLD-TDP).

The role of TDP-43 in neurodegeneration in ALS and other neurodegenerative disorders has been reviewed in several recent publications (Chen-Plotkin et al 2010; Gendron et al 2010; Geser et al 2010; Mackenzie et al 2010).

ALS is a neurodegenerative disease, characterised by progressive paralysis and muscle wasting, consequent on the degeneration of both upper and lower motor neurones in the primary motor cortex, brainstem and spinal cord. It is sometimes referred to as motor neuron disease (MND) but there are diseases other than ALS which affect either upper or lower motor neurons. A definite diagnosis requires both upper and lower motor neurone signs in the bulbar, arm and leg musculature with clear evidence of clinical progression that cannot be explained by any other disease process (Wijesekera and Leigh 2009).

Although the majority of cases are ALS-TDP, there are other cases where the pathological protein differs from TDP-43. Misfolded SOD1 is the pathological protein in ubiquitin-positive inclusions in ALS with SOD1 mutations (Seetharaman et al 2009) and in a very small subset (approximately 3-4%) of familial ALS, due to mutations in FUS (fused in sarcoma protein), the ubiquitinated pathological protein is FUS (Vance et al 2009; Blair et al 2010). FUS, like TDP-43, appears to be important in nuclear-cytoplasmic shuttling although the ways in which impaired nuclear import of FUS remains unclear. A new molecular classification of ALS, adapted from Mackenzie et al (2010), reflects the distinct underlying pathological mechanisms in the different subtypes (see Table below).

New Molecular Classification of ALS (modified from Mackenzie et al 2010). In the majority of cases, TDP-43 is the pathological ubiquitinated protein found in ALS.

| | Ubiquitin-positive inclusions in ALS | | |
|---|---|---|---|
| | Ubiquitinated disease protein | | |
| | TDP-43 | FUS | SOD1 |
| Clinico-pathologic subtype | ALS-TDP | ALS-FUS | ALS-SOD1 |
| Associated genotype | TARDBP | FUS | SOD1 |

-continued

| | Ubiquitin-positive inclusions in ALS | | |
|---|---|---|---|
| | Ubiquitinated disease protein | | |
| | TDP-43 | FUS | SOD1 |
| Frequency of ALS cases | Common | Rare | Rare |

Amyotrophic lateral sclerosis has been recognised as a nosological entity for almost a century and a half and it is recognised in ICD-10 and is classified as a subtype of MND in ICD 10, codeG12.2. Reliable clinical diagnostic are available for ALS, which differ little from Charcot's original description, and neuropathological criteria, reflecting the underlying molecular pathology, have also been agreed.

While ALS is classified pathologically into three subgroups, ALS-TDP, ALS-SOD1 and ALS-FUS, both latter conditions are rare. The largest study to date showed all sporadic ALS cases to have TDP-43 pathology (Mackenzie et al 2007). Only around 5% of ALS is familial (Byrne et al 2010) and mutations in SOD1, the commonest mutations found in FALS, account for between 12-23% of cases (Andersen et al 2006). SOD1 may also be implicated in 2-7% of SALS. Mutations in FUS appear to be far less common, accounting for only around 3-4% of FALS (Blair et al 2010). So it can be reliably predicted that a clinical case of SALS will have TDP-43 based pathology. Similarly this can be reliably predicted in FALS due to mutations in TDP-43, which account for around 4% of cases (Mackenzie et al 2010). ALS with mutations in: VCP, accounting for 1-2% of FALS (Johnson et al 2010), ANG (Seilhean et al 2009), and CHMP2B (Cox et al 2010) have also been reported to be associated with TDP-43 positive pathology. Although SOD1, FUS and ATXN2 mutations have not been found to be associated with TDP-43 positive aggregates, it has however been reported that TDP-43 is implicated in the pathological processes putatively arising from these mutations (Higashi et al 2010; Ling et al 2010; Elden et al 2010).

It is therefore established that TDP-43 has an important, and potentially central role, in the pathogenesis of the vast majority of SALS cases and may be implicated in the pathogenesis of a significant proportion of FALS. ALS is now widely considered to be a TDP-43 proteinopathy (Neumann et al 2009) and numerous in vitro, and in vivo studies provide support to the hypothesis that toxic gain of function, due to TDP-43 aggregation is responsible for at least some of the neurotoxicity in the disease.

FTLD syndromes are insidious onset, inexorably progressive, neurodegenerative conditions, with peak onset in late middle age. There is often a positive family history of similar disorders in a first degree relative.

Behavioural variant FTD is characterised by early prominent change in social and interpersonal function, often accompanied by repetitive behaviours and changes in eating pattern. In semantic dementia there are prominent word finding problems, despite otherwise fluent speech, with degraded object knowledge and impaired single word comprehension on cognitive assessment. Progressive non-fluent aphasia presents with a combination of motor speech problems and grammatical deficits. The core clinical diagnostic features for these three FTLD syndromes are shown in the Table below and the full criteria in Neary et al (1998).

Clinical Profile and Core Diagnostic Features of FTLD Syndromes

| FTLD Syndrome -Clinical Profile | Core Diagnostic Features |
|---|---|
| Frontotemporal Dementia<br>Character change and disordered social conduct are the dominant features initially and throughout the disease course. Instrumental functions of perception, spatial skills, praxis and memory are intact or relatively well preserved. | 1. Insidious onset and gradual progression<br>2. Early decline in social interpersonal conduct<br>3. Early impairment in regulation of personal conduct<br>4. Early emotional blunting<br>5. Early loss of insight |
| Semantic Dementia<br>Semantic disorder (impaired understanding of word meaning and/or object identity) is the dominant feature initially and throughout the disease course. Other aspects of cognition, including autobiographic memory, are intact or relatively well preserved. | A) Insidious onset and gradual progression<br>B) Language disorder characterised by<br>  1. Progressive, fluent empty speech<br>  2. Loss of word meaning manifest by impaired naming and comprehension<br>  3. Semantic paraphasias and/or<br>  4.<br>Perceptual disorder characterised by<br>  1. Prosopagnosia: impaired recognition of identity of familiar faces and/or<br>  2. Associative agnosia: impaired recognition of object identity<br>C) Preserved perceptual matching and drawing reproduction<br>D) Preserved single word repetition<br>E) Preserved ability to read aloud and write to dictation orthographically regular words |
| Progressive Non-fluent Aphasia<br>Disorder of expressive language is the dominant feature initially and throughout the disease course. Other aspects of cognition are intact or relatively well preserved. | A) Insidious onset and gradual progression<br>B) Non-fluent spontaneous speech with at least one of the following: agrammatism, phonemic paraphasias or anomia |

The discovery that TDP-43-positive inclusions characterize ALS and FTLD-TDP (Neumann et al 2006) was quickly followed by the identification of missense mutations in the TARDBP gene in both familial and sporadic cases of ALS (Gitcho et al 2008; Sreedharan et al., 2008). So far, 38 different TARDBP mutations have been reported in 79 genealogically unrelated families worldwide (Mackenzie et al 2010). TARDBP mutations account for approximately 4% of all familial and around 1.5% of sporadic ALS cases.

As of December 2010, mutations in thirteen genes which are associated with familial and sporadic ALS have been identified. Linkage of ALS to five other chromosome loci has been demonstrated but thus far specific mutations have not been identified.

TDP-43 Proteinopathies

MT has a mode of action which targets and can reduce TDP-43 protein aggregation in cells, which is a pathological feature of the vast majority of both familial and sporadic ALS and is also characteristic of FTLD-P.

In addition laboratory data shows that methylthioninium inhibits the formation of TDP-43 aggregates in SH-SY5Y cells. Following treatment with 0.05 µM MT, the number of TDP-43 aggregates was reduced by 50%. These findings were confirmed by immunoblot analysis (Yamashita et al 2009).

The compounds and compositions of the invention may therefore be useful for the treatment of amyotrophic lateral sclerosis (ALS) and frontotemporal lobar degeneration (FTLD).

Huntington's Disease and Polyglutamine Disorders

MT can reduce polyglutamine protein aggregation in cells, which is a pathological feature of Huntington's disease. Huntington's disease is caused by expansion of a translated CAG repeat located in the N-terminus of huntingtin. Wild-type chromosomes contain 6-34 repeats whereas, in Huntington's disease, chromosomes contain 36-121 repeats. The age of onset of disease correlates inversely with the length of the CAG tracts that code for polyglutamine repeats within the protein.

Laboratory data shows that methylthioninium inhibits the formation of aggregates of a huntingtin derivative containing a polyglutamine stretch of 102 residues in zebrafish (van Bebber et al. 2010). MT, when tested at 0, 10 and 100 µM, prevented the formation of such aggregates in zebrafish in a dose-dependent manner.

The compounds and compositions of the invention may therefore be useful for the treatment of Huntington's disease and other polyglutamine disorders such as spinal bulbar muscular atrophy (or Kennedy disease), and dentatorubropallidoluysian atrophy and various spinocerebellar ataxias (Orr & Zoghbi, 2007).

Mitochondrial Diseases and Lafora Disease

The organ most frequently affected in mitochondrial disorders, particularly respiratory chain diseases (RCDs), in addition to the skeletal muscle, is the central nervous system (CNS). CNS manifestations of RCDs comprise stroke-like episodes, epilepsy, migraine, ataxia, spasticity, movement disorders, psychiatric disorders, cognitive decline, or even dementia (mitochondrial dementia). So far mitochondrial dementia has been reported in MELAS, MERRF, LHON, CPEO, KSS, MNGIE, NARP, Leigh syndrome, and Alpers-Huttenlocher disease (Finsterer, 2009). There are four complexes in the mitochondrial respiration chain, involving a series of electron transfers. Abnormal function of any of these complexes can result in mitochondrial diseases secondary to an abnormal electron transport chain and subsequent abnormal mitochondrial respiration. Complex Ill of the mitochondrial respiration chain acts to transfer electrons to cytochrome c.

Compounds and compositions of the invention may also be used to treat mitochondrial diseases which are associated with a deficient and/or impaired complex Ill function of the respiration chain. The compounds have the ability to act as effective electron carrier and/or transfer, as the thioninium moiety has a low redox potential converting between the oxidised and reduced form. In the event of an impaired and/or deficient function of Complex Ill leading to mitochondrial diseases, compounds of the invention are also able to perform the electron transportation and transfer role of complex Ill because of the ability of the thioninium moiety to shuttle between the oxidised and reduced form, thus acting as an electron carrier in place of sub-optimally functioning complex Ill, transferring electrons to cytochrome c.

Compounds and compositions of the invention also have the ability to generate an active thioninium moiety that has the ability to divert misfolded protein/amino acid monomers/oligomers away from the Hsp70 ADP-associated protein accumulation and/or refolding pathways, and instead rechannel these abnormal folded protein monomers/oligomers to the pathway that leads directly to the Hsp70 ATP-dependent ubiquitin-proteasome system (UPS), a pathway which removes these misfolded proteins/amino acid monomers/oligomers via the direct route (Jinwal et al. 2009).

Lafora disease (LD) is an autosomal recessive teenage-onset fatal epilepsy associated with a gradual accumulation of poorly branched and insoluble glycogen, termed polyglucosan, in many tissues. In the brain, polyglucosan bodies, or Lafora bodies, form in neurons. Inhibition of Hsp70 ATPase by MT (Jinwal et al. 2009) may upregulate the removal of misfolded proteins. Lafora disease is primarily due to a lysosomal ubiquitin-proteasomal system (UPS) defect because of a mutation in either the Laforin or Malin genes, both located on Chromosome 6, which result in inclusions that may accelerate the aggregation of misfolded tau protein. Secondary mitochondrial damage from the impaired UPS may further result in a suppressed mitochondrial activity and impaired electron transport chain leading to further lipofuscin and initiating the seizures that are characteristic of Lafora disease.

The MT moiety may disaggregate existing tau aggregates, reduce more tau accumulating and enhance lysosomal efficiency by inhibiting Hsp70 ATPase. MT may lead to a reduction in tau tangles by enhancing the ubiquitin proteasomal system removal of tau monomers/oligomers, through its inhibitory action on Hsp70 ATPase.

Thus compounds and compositions of the present invention may have utility in the treatment of Lafora disease.

Mixtures of Oxidised and Reduced MT Compounds

The LMT-containing compounds utilised in the present invention may include oxidised (MT$^+$) compounds as 'impurities' during synthesis, and may also oxidize (e.g., autoxidize) after synthesis to give the corresponding oxidized forms. Thus, it is likely, if not inevitable, that compositions comprising the compounds of the present invention will contain, as an impurity, at least some of the corresponding oxidized compound. For example an "LMT" salt may include up to 15% e.g. 10 to 15% of MT$^+$ salt.

When using mixed MT compounds the MT dose can be readily calculated using the molecular weight factors of the compounds present.

Salts and Solvates

Although the MT-containing compounds described herein are themselves salts, they may also be provided in the form of a mixed salt (i.e., the compound of the invention in combination with another salt). Such mixed salts are intended to be encompassed by the term "and pharmaceutically acceptable salts thereof". Unless otherwise specified, a reference to a particular compound also includes salts thereof.

The compounds of the invention may also be provided in the form of a solvate or hydrate. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, a penta-hydrate etc. Unless otherwise specified, any reference to a compound also includes solvate and any hydrate forms thereof.

Naturally, solvates or hydrates of salts of the compounds are also encompassed by the present invention.

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1. Schematic of the simplified population PK model for MT.

Figure 2A:
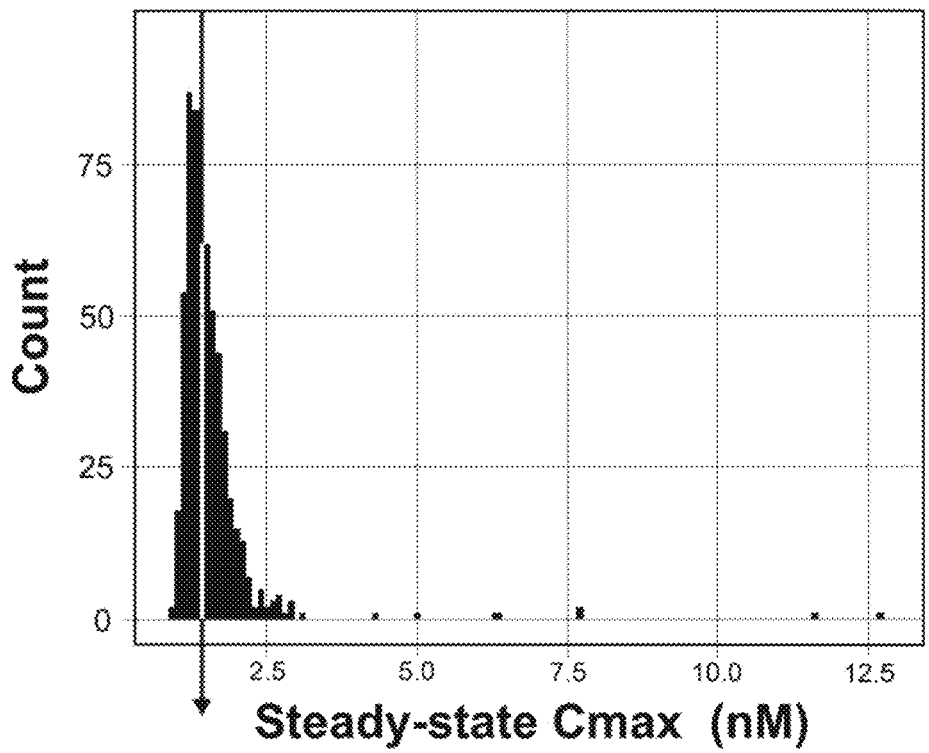
Figure 2B:
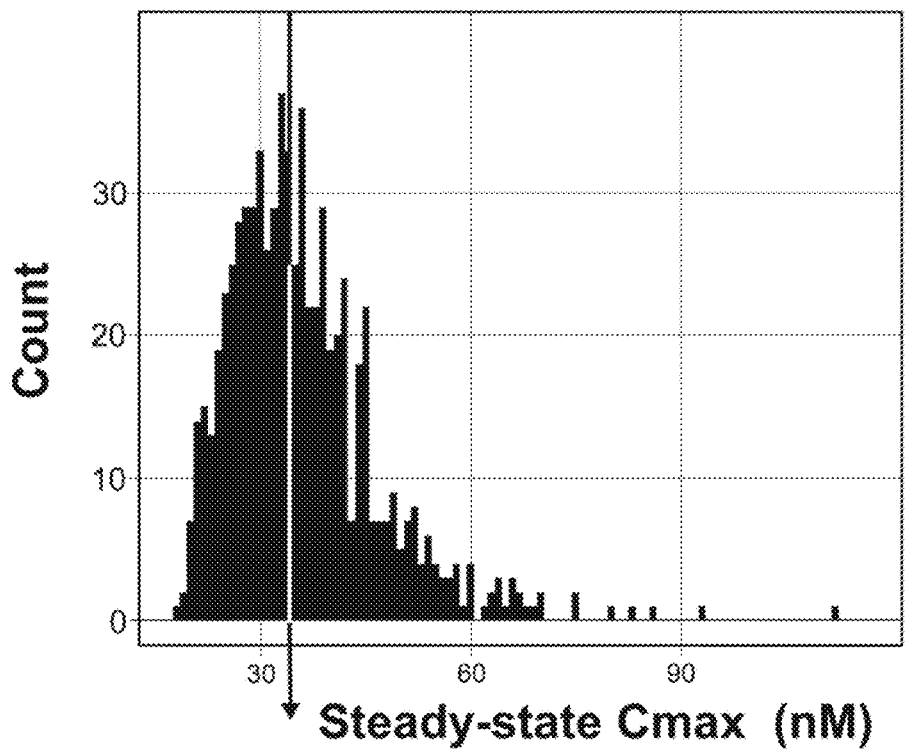

FIGS. 2A-2B. Histogram of Bayesian post-hoc estimates of steady-state parent MT Cmax in AD patients from Studies 005 and 015 who received LMTM 4 mg BID or c. 200 mg/day.

Figure 3B:
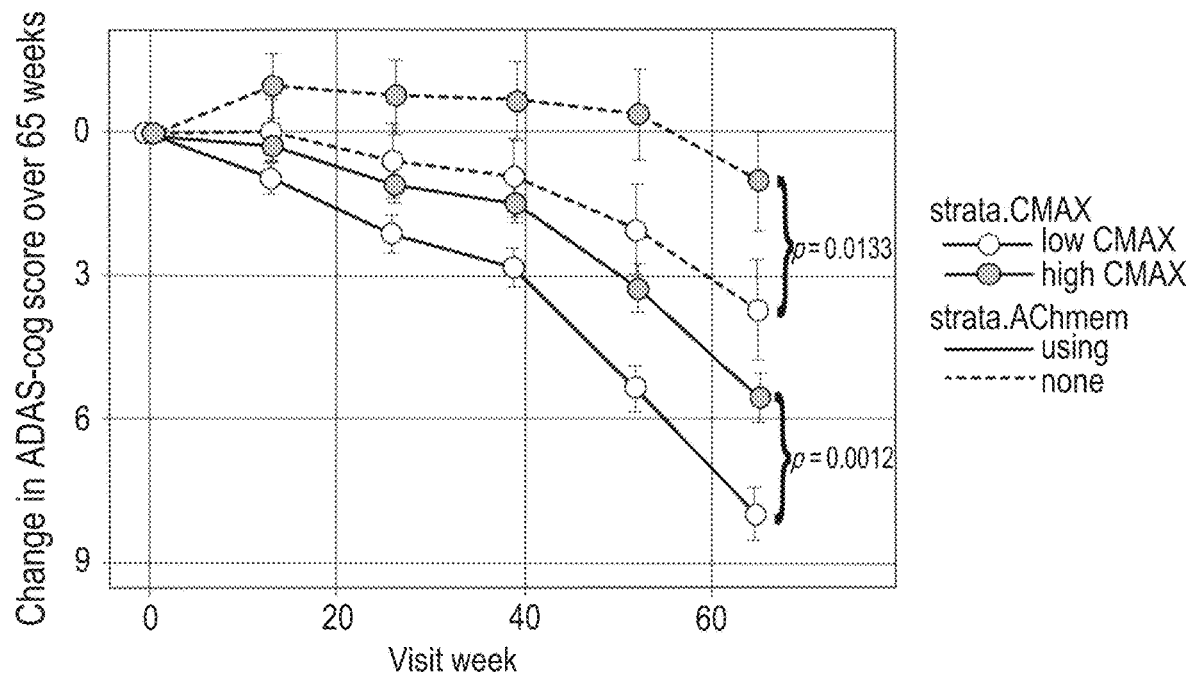

FIGS. 3A-3B. ADAS-cog change over 65 weeks for pooled 8 mg/day dose as mono- or add-on therapy in AD subjects from Studies 005 and 015 according to estimated steady-state Cmax. Note the lower p-value in 'strata.Acmem' is due to larger number of subjects receiving LMTM as add-on treatment.

FIGS. 4A-4C. Analysis of AD subjects showing reduced brain atrophy and ventricular expansion in high Cmax group both as monotherapy and as add-on.

FIG. 5. Estimation of proportion of AD subjects in high Cmax group according to dose. The Y axis shows the % over the threshold. 4 mg BID is 50% reflecting the original median split of the high and low Cmax groups at this dosage.

Figure 6A:
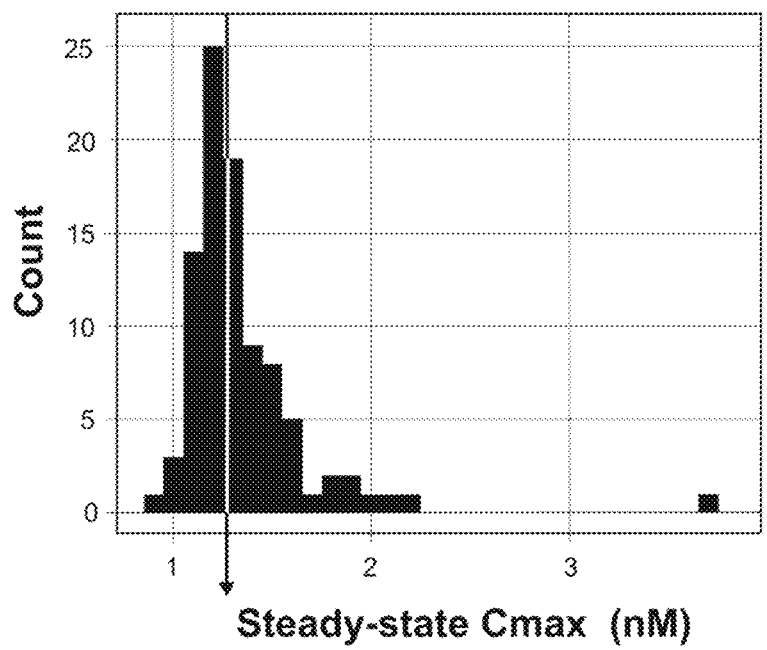
Figure 6B:
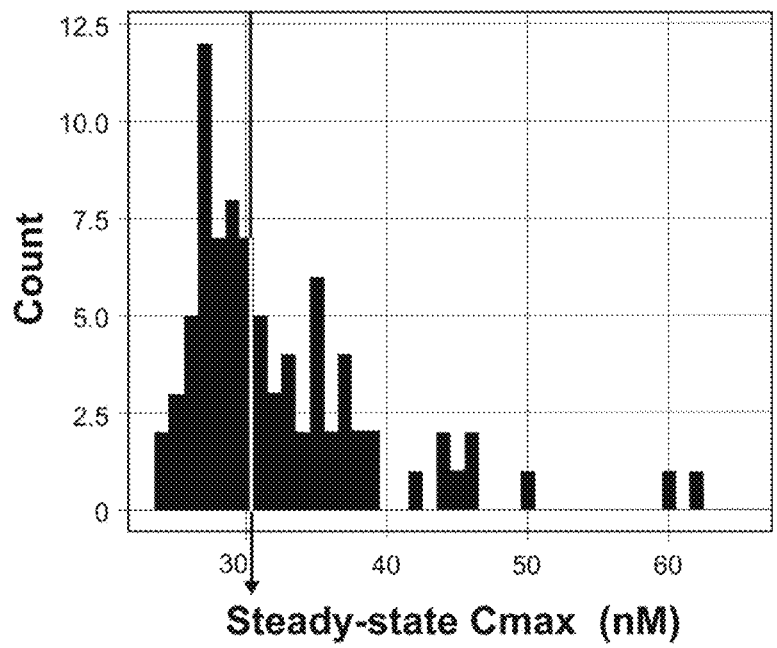

FIGS. 6A-6B. Distribution of estimated Cmax values for 8 and 200 mg/day in bvFTD trial subjects FIG. 7. Difference in decline on ACE-R scale according to Cmax group in bvFTD patients receiving LMTM 8 mg/day as monotherapy for treatment of bvFTD FIG. 8. Difference in decline on ACE-R scale according to Cmax group in bvFTD patients receiving LMTM 200 mg/day as monotherapy for treatment of bvFTD FIG. 9. Difference in decline on FAQ scale according to Cmax group in bvFTD patients receiving LMTM 8 mg/day as monotherapy FIG. 10. Difference in decline on FAQ scale according to Cmax group in bvFTD patients receiving LMTM 8 mg/day or 200 mg/day as monotherapy FIGS. 11A-11C. Difference in WBV, FTV and LVV according to Cmax group in bvFTD patients receiving LMTM 8 mg/day as monotherapy.

FIG. 12. Sigmoid $E_{max}$ analysis for ADAS-$cog_{11}$ decline at week 65 with model covariates at population mean values and 90% bootstrap confidence intervals using $C_{max,ss}$ at day 1 for low dose AD patients from studies TRx-237-005 and TRx-237-015.

FIGS. 13A-13D. Concentration-response relationships for clinical and MRI volumetric endpoints for $C_{max,ss}$ groupings of AD patients receiving LMTM at a dose of 8 mg/day FIGS. 14A-14D. Comparison of primary clinical and MRI volumetric endpoints for all AD patients: categorized by $C_{max,ss}$ above ("high exposure") or below ("low exposure") parent MT threshold of 0.373 ng/mL.

FIG. 15. Expected percentage of AD patients above the critical therapeutic threshold for $C_{max,ss}$ (0.393 ng/ml) and $C_{ave,ss}$ (0.223 ng/ml) according to once daily (qd) and twice daily (bid) dosing regimes.

FIGS. 16A-16D. Comparison of primary clinical and MRI endpoint in AD patients receiving LMTM, 8 mg/day: categorised by $C_{max,ss}$ above ("high exposure") or below ("low exposure") parent MT threshold of 0.373 ng/ml and AChEI and/or memantine use status.

FIG. 17. Pharmacokinetic-pharmacodynamic response on the ADAS-cog scale over 65 weeks in AD patients taking LMTM at a dose of 8 mg/day and categorized by co-medication status with AD-labelled treatments.

FIGS. 18A-18E. Concentration-response relationships for ACE-R, FAQ, FTV, LVV and WBV in bvFTD patients.

FIGS. 19A-19E. Estimated change from baseline over time in clinical and MRI neuroimaging endpoints in bvFTD patients taking 8 mg/day categorized by plasma levels above or below the $C_{max,ss}$ threshold of 0.346 ng/ml.

FIG. 20. Fit of expanded Hill equation with change in whole brain volume over 52 weeks for bvFTD patients.

EXAMPLES

Example 1—Provision of MT-Containing Compounds

Methods for the chemical synthesis of the MT-containing compounds described herein are known in the art. For example:

Synthesis of compounds 1 to 7 can be performed according to the methods described in WO2012/107706, or methods analogous to those.

Synthesis of compound 8 can be performed according to the methods described in WO2007/110627, or a method analogous to those.

Example 2—Provision of AD Symptomatic Treatments

AD symptomatic treatments includes those which directly modify synaptic neurotransmission in the brain are commercially available as acetylcholinesterase inhibitors (AChEIs) or NMDA receptor antagonists.

Examples of AChEIs include tacrine (Cognex™, First Horizon), donepezil (Aricept™, Eisai/Pfizer), rivastigmine (Exelon™, Novartis), and galantamine (Razadyne™, formerly Reminyl™, Ortho-McNeil). Memantine is available as Ebixa™ or Namenda™ e.g. from Forest.

Example 3—a Novel Population PK Model for MT

In an initial model (not shown), the disposition of all MT moieties (parent MT, desmethyl MT, and LMT-conjugate) was simultaneously characterized by a multi-compartment model. The disposition of parent MT post PO administration was adequately described by a two-compartment model with binding occurring in the plasma and tissue compartments and a delayed absorption occurring through two transit compartments. This model has a fixed Vc. There was a trend for absorption rate to be slower with increasing dose, which is incorporated into the model using a dose-dependent absorption rate constant (Ka). Apparent oral clearance (CL/F) of parent MT was related to renal function such that a small portion of the variability in parent CL is described by normalized creatinine clearance (CLCRN). A minor fraction of parent MT was metabolized into desmethyl MT, and the disposition of desmethyl MT was described by a two-compartment model with linear elimination. Parent MT was also converted into LMT-glucuronide, and its disposition was described by a one-compartment model with linear elimination. Of note, a fraction of LMT-conjugate underwent enterohepatic recycling (EHR), which was physiologically mimicked via a latent gallbladder compartment with a pulsatile pattern of bile secretion.

The above-described model was applied to the data from a single- and multiple-dose Phase 1 study in elderly subjects (Study 036) in order to assess the ability of the model to predict steady-state PK of parent MT. The model was successfully fit to data obtained from subjects who received either 4 mg BID or 10 mg QD of LMTM in Study 036.

This, the PK model was then further developed and simplified to a two compartment model fit to the parent MT concentrations only. A schematic of this simplified population PK model for MT is provided in FIG. 1. This model has a fixed Vc, but the dose-dependent Ka is removed.

This model was derived from Study 036 discussed above. The disposition of parent MT post PO administration of LMTM was adequately described by a two-compartment model with and a delayed absorption occurring through two transit compartments. Apparent oral clearance (CL/F) of parent MT was related to renal function such that a small portion of the variability in parent CL is described by normalized creatinine clearance (CLCRN).

The model was successfully fit to data obtained from subjects who received either 4 mg BID or 10 mg QD of LMTM in Study 036.

The simplified model provides similar fit to the previous more sophisticated model, but allows co-modelling of all of the data from Study 036.

Overall, excellent fits to the individual subject data were obtained suggesting that the model provided an adequate description of the PK of parent MT after administration of LMTM.

Example 4—Estimation of Cmax of Parent MT in the Patients Who Received 4 mg BID in the Phase 3 AD studies (Studies "005" and "015")

The trial design for the Phase 3 AD studies "005" and "015" are described in Examples 4 and 3 respectively of WO2018/019823, which Examples also discuss those results. The disclosure of those Examples is specifically incorporated herein by reference. Briefly, those Phase 3 trials compared high doses of LMTM (150-250 mg/day) with a low dose (8 mg/day) intended as a mask for potential urine discolouration (Gauthier 2016; Wilcock 2018). These showed the potential utility for LMTM, particularly as monotherapy, in delaying disease progression on clinical and brain imaging endpoints, and that the high doses conferred no greater potential benefit than the 8 mg/day dose.

The population PK model was then used to estimate Cmax of parent MT in the patients who received 4 mg or high dose (c. 200 mg/day) in these Phase 3 AD studies. This Bayesian process involved fixing the population mean and inter-individual variability parameters to the estimates from the fit of the population PK model to the steady-state data from Study 036 and allowing the program to select a set of parameters, given those Bayesian priors, which best predicts the parent MT concentrations from Day 1 in each individual.

The distribution of resultant Cmax estimates are provided in FIGS. 2a and 2b. The ~200 mg/day group represents pooled high dose subjects from Study 015 (150 & 250 mg/day) and Study 005 (200 mg/day).

In these Figures the vertical black line indicates median for each distribution, which can be used to divide patients into low and high Cmax groups.

Example 5—assessment of different effects of pooled 8 mg/day dose as mono- or add-on Therapy from Studies 005 and 015 in High and Low Cmax Groups at Steady-State Using an Mixed effect Model Repeat Measurement (MMRM) approach, ADAS-cog change over 65 weeks for pooled 8 mg/day dose as mono- or add-on therapy from Studies 005 and 015 was then calculated for the "High Cmax" and "Low Cmax" groups, in each case divided into those receiving LMTM as monotherapy, or in combination ("add-on") with symptomatic treatments (AChEIs and\or memantine). The results are shown in FIGS. 3a and 3b which show the same data. Patients using symptomatic treatments are labelled "Achmem".

FIG. 3a emphasises the findings in WO2018/019823 that Symptomatic treatments interfere with LMTM treatment effect. The mean difference between monotherapy and add-on can be seen to be ~4 ADAS-cog units.

As highlighted in FIG. 3b, unexpectedly, the analysis of this low (8 mg/day) dose also revealed a difference between Cmax high and low groups for monotherapy of ~2.4 ADAS-cog units, and a difference between Cmax high and low groups for the add-on groups of ~2.7 ADAS-cog units i.e. the same concentration-dependent difference seen for monotherapy and add-on treatment.

In further analyses, FIG. 4 shows that the high Cmax group has less whole brain and temporal lobe atrophy, and less expansion of ventricles both as monotherapy and add-on therapy. As expected there was less brain atrophy in monotherapy than in add-on groups. It should be noted that the differences achieve statistical significance only for the add-on group, which had substantially larger number of subjects.

Corresponding analysis of the pooled high dose group (average 200 mg/day) did not show a corresponding different treatment effect between Cmax high and low groups, whether as monotherapy or add-on (data not shown).

Example 6—Safety and Adverse Events: Benefits in Using Minimal Effective Dose of LMT Compounds Three Phase 3, double-blind, controlled studies of LMTM have been completed (one each in subjects with mild and mild to moderate AD and one in subjects with bvFTD). Results of the AD studies have been published (Gauthier et al., 2016; Wilcock et al., 2018).

In these three studies, 1897 subjects received at least one dose of LMTM (Safety Population [Five additional subjects with AD, participating at one site in Study TRx-237-005, received a dose of study drug but were excluded from all analyses due to GCP violations], 1679 subjects with AD and 218 subjects with bvFTD). Of these, 860 subjects received the control (LMTM 8 mg/day, 750 with AD and 110 with bvFTD) and 1037 subjects received at least one dose of LMTM in the higher doses of 150 to 250 mg/day (929 with AD and 108 with bvFTD).

The mean ages of study participants were 71 years (ranging up to 89 years) for subjects with AD and 63 years (ranging up to 79 years) for subjects with bvFTD. Overall, there was a comparable representation by sex (55% female), with more AD subjects being female (58%) and more bvFTD subjects being male (63%). Most subjects were White (88% AD and 91% bvFTD). Approximately 17% of the AD subjects received LMTM as monotherapy (as recorded on the concomitant medication case report form rather than by stratification [overall, 87% of subjects were receiving AChEI and/or memantine based on the stratified randomisation]), with the remainder receiving concomitant AChEI and/or memantine. On the other hand, most subjects with bvFTD received LMTM as monotherapy (79%). Psychiatric disorders/symptoms were common, with depression reported for 23% of the subjects overall and anxiety for 12%. Concomitant use of antidepressants and antipsychotics was more common in subjects with bvFTD (50% and 22%, respectively) as compared with AD (36% and 10%, respectively).

The most common Treatment emergent adverse events (TEAEs) considered at least possibly associated with LMTM given in a dose of 8 mg/day are GI (mostly diarrhea and nausea), genitourinary (mostly pollakiuria and urinary incontinence), haematologic (anaemia, decreased folate, and folate deficiency), and nervous system related (mostly fatigue, dizziness, headache, agitation, and insomnia). Other common events are considered to represent events that are expected in these patient populations over a 12- to 18-month duration.

At the higher LMTM doses studied, 150 to 250 mg/day, there was a dose-related increase in the incidence of anaemia-related TEAEs (decreased haemoglobin in addition to anaemia, decreased folate, and folate deficiency), gastrointestinal events (including vomiting and the possibly associated observation of decreased weight in addition to diarrhoea and nausea), and genitourinary events (including dysuria, micturition urgency, and apparent urinary tract infections in addition to pollakiuria and urinary incontinence). The lack of a dose response in falls and nervous system/psychiatric events (other than agitation) suggests that these are associated with the subjects' underlying condition rather than treatment.

The incidence of the most common TEAEs are summarised by dose in the following Table EX1. This includes TEAEs that occurred at an incidence of ≥2.0% either in subjects randomised to LMTM 8 mg/day or higher doses (150 to 250 mg/day). The subset of TEAEs that were severe in intensity are also included. As can be seen, few events occurred in severe intensity, regardless of dose.

TABLE EX1

Incidence of Treatment-emergent Adverse Events in ≥2.0% of Subjects by Dose:
LMTM 8 mg/day versus Higher Doses
(Phase 3, Double-blind, LMTM Pooled Safety Population)

| MedDRA System Organ Class/Preferred Term | LMTM 8 mg/day (N = 860) | | Higher Doses (150-250 mg/day) (N = 1037) | |
|---|---|---|---|---|
| | All n (%) | Severe Intensity n (%) | All n (%) | Severe Intensity n (%) |
| No. (%) of Subjects Reporting at Least One TEAE | 720 (83.7%) | 86 (10.0%) | 902 (87.0%) | 126 (12.2%) |
| Blood and Lymphatic System Disorders | | | | |
| Anaemia | 19 (2.2%) | 1 (0.1%) | 59 (5.7%) | 0 |
| Cardiac Disorders | | | | |
| Atrial fibrillation | 17 (2.0%) | 3 (0.3%) | 10 (1.0%) | 2 (0.2%) |
| Gastrointestinal Disorders | | | | |
| Abdominal pain | 16 (1.9%) | 1 (0.1%) | 30 (2.9%) | 1 (0.1%) |
| Abdominal pain upper | 10 (1.2%) | 1 (0.1%) | 21 (2.0%) | 0 |
| Constipation | 23 (2.7%) | 2 (0.2%) | 24 (2.3%) | 1 (0.1%) |
| Diarrhoea | 109 (12.7%) | 5 (0.6%) | 278 (26.8%) | 14 (1.4%) |
| Nausea | 39 (4.5%) | 1 (0.1%) | 86 (8.3%) | 1 (0.1%) |
| Vomiting | 20 (2.3%) | 0 | 80 (7.7%) | 3 (0.3%) |
| General Disorders and Administration Site Conditions | | | | |
| Fatigue | 26 (3.0%) | 0 | 38 (3.7%) | 1 (0.1%) |
| Oedema peripheral | 19 (2.2%) | 0 | 20 (1.9%) | 0 |
| Infections and Infestations | | | | |
| Bronchitis | 27 (3.1%) | 0 | 19 (1.8%) | 0 |
| Nasopharyngitis | 40 (4.7%) | 0 | 43 (4.1%) | 0 |
| Upper respiratory tract infection | 35 (4.1%) | 0 | 34 (3.3%) | 0 |
| Urinary tract infection | 76 (8.8%) | 1 (0.1%) | 116 (11.2%) | 3 (0.3%) |
| Injury, Poisoning and Procedural Complications | | | | |
| Contusion | 24 (2.8%) | 0 | 15 (1.4%) | 0 |
| Fall | 90 (10.5%) | 4 (0.5%) | 78 (7.5%) | 7 (0.7%) |
| Laceration | 17 (2.0%) | 0 | 14 (1.4%) | 1 (0.1%) |
| Investigations | | | | |
| Blood creatine phosphokinase increased | 18 (2.1%) | 0 | 31 (3.0%) | 0 |
| Blood folate decreased | 45 (5.2%) | 0 | 76 (7.3%) | 0 |
| Creatinine renal clearance decreased | 20 (2.3%) | 0 | 26 (2.5%) | 0 |
| Haemoglobin decreased | 6 (0.7%) | 0 | 34 (3.3%) | 0 |
| Vitamin B12 decreased | 23 (2.7%) | 0 | 21 (2.0%) | 0 |
| Weight decreased | 18 (2.1%) | 0 | 39 (3.8%) | 0 |
| Metabolism and Nutrition Disorders | | | | |
| Decreased appetite | 13 (1.5%) | 0 | 39 (3.8%) | 1 (0.1%) |
| Dehydration | 17 (2.0%) | 4 (0.5%) | 18 (1.7%) | 2 (0.2%) |
| Folate deficiency | 17 (2.0%) | 0 | 45 (4.3%) | 0 |

TABLE EX1-continued

Incidence of Treatment-emergent Adverse Events in ≥2.0% of Subjects by Dose:
LMTM 8 mg/day versus Higher Doses
(Phase 3, Double-blind, LMTM Pooled Safety Population)

| MedDRA System Organ Class/Preferred Term | LMTM 8 mg/day (N = 860) | | Higher Doses (150-250 mg/day) (N = 1037) | |
|---|---|---|---|---|
| | All n (%) | Severe Intensity n (%) | All n (%) | Severe Intensity n (%) |
| Musculoskeletal and Connective Tissue Disorders | | | | |
| Arthralgia | 28 (3.3%) | 0 | 31 (3.0%) | 1 (0.1%) |
| Back pain | 31 (3.6%) | 1 (0.1%) | 44 (4.2%) | 2 (0.2%) |
| Pain in extremity | 19 (2.2%) | 1 (0.1%) | 17 (1.6%) | 0 |
| Nervous System Disorders | | | | |
| Cerebral microhaemorrhage | 24 (2.8%) | 0 | 16 (1.5%) | 0 |
| Dizziness | 49 (5.7%) | 3 (0.3%) | 64 (6.2%) | 2 (0.2%) |
| Headache | 55 (6.4%) | 1 (0.1%) | 61 (5.9%) | 3 (0.3%) |
| Syncope | 26 (3.0%) | 1 (0.1%) | 28 (2.7%) | 5 (0.5%) |
| Tremor | 20 (2.3%) | 0 | 13 (1.3%) | 0 |
| Psychiatric Disorders | | | | |
| Agitation | 46 (5.3%) | 1 (0.1%) | 61 (5.9%) | 7 (0.7%) |
| Anxiety | 52 (6.0%) | 0 | 39 (3.8%) | 2 (0.2%) |
| Confusional state | 22 (2.6%) | 2 (0.2%) | 45 (4.3%) | 2 (0.2%) |
| Depression | 41 (4.8%) | 0 | 37 (3.6%) | 2 (0.2%) |
| Hallucination | 13 (1.5%) | 0 | 21 (2.0%) | 4 (0.4%) |
| Insomnia | 29 (3.4%) | 0 | 32 (3.1%) | 0 |
| Suicidal ideation | 27 (3.1%) | 2 (0.2%) | 30 (2.9%) | 0 |
| Renal and Urinary Disorders | | | | |
| Dysuria | 6 (0.7%) | 0 | 75 (7.2%) | 1 (0.1%) |
| Micturition urgency | 11 (1.3%) | 0 | 35 (3.4%) | 0 |
| Pollakiuria | 19 (2.2%) | 0 | 71 (6.8%) | 2 (0.2%) |
| Urinary incontinence | 34 (4.0%) | 0 | 63 (6.1%) | 1 (0.1%) |
| Respiratory, Thoracic and Mediastinal Disorders | | | | |
| Cough | 37 (4.3%) | 0 | 42 (4.1%) | 0 |
| Skin and Subcutaneous Tissue Disorders | | | | |
| Rash | 21 (2.4%) | 0 | 30 (2.9%) | 0 |
| Vascular Disorders | | | | |
| Hypertension | 20 (2.3%) | 0 | 22 (2.1%) | 1 (0.1%) |

The TEAEs are further analysed by using groupings of related MedDRA (Medical Dictionary for Regulatory Activities) preferred terms to better estimate the incidence of potentially treatment related adverse events. The incidence of all groupings for subjects categorised by dose (8 mg/day versus higher doses of 150 to 250 mg/day) is shown in the following Table EX2:

TABLE EX2

Incidence of Treatment-emergent Adverse Events groupedLMTM
8 mg/day versus Higher Doses
(Phase 3, Double-blind, LMTM Pooled Safety Population)

| TauRx Grouping Term | LMTM 8 mg/day (N = 860) n (%) | Higher Doses (150-250 mg/day) (N = 1037) n (%) |
|---|---|---|
| Affective/Anxiety Symptoms | 60 (7.0%) | 55 (5.3%) |
| Anaemia | 111 (12.9%) | 219 (21.1%) |
| Behavioral Symptoms | 114 (13.3%) | 118 (11.4%) |
| Falls and Related Terms | 188 (21.9%) | 202 (19.5%) |
| Hepatic Function Impairment | 13 (1.5%) | 34 (3.3%) |
| Hypersensitivity | 42 (4.9%) | 63 (6.1%) |
| Ischaemic Events, Inclusive of Myocardial Infarction | 20 (2.3%) | 35 (3.4%) |

TABLE EX2-continued

Incidence of Treatment-emergent Adverse Events groupedLMTM
8 mg/day versus Higher Doses
(Phase 3, Double-blind, LMTM Pooled Safety Population)

| TauRx Grouping Term | LMTM 8 mg/day (N = 860) n (%) | Higher Doses (150-250 mg/day) (N = 1037) n (%) |
|---|---|---|
| Psychotic Symptoms | 28 (3.3%) | 34 (3.3%) |
| Renal Function Impairment | 29 (3.4%) | 42 (4.1%) |
| Renal and Urinary Disorders (Including Infections) | 135 (15.7%) | 326 (31.4%) |
| Sleep Disorders | 41 (4.8%) | 48 (4.6%) |
| Targeted Gastrointestinal Events | 183 (21.3%) | 401 (38.7%) |

The groupings occurring in ≥10.0% of subjects treated with LMTM 8 mg/day include falls and related terms (22%), GI events (21%), renal and urinary disorders including infections (16%), behavioural symptoms and terms indicative of anaemia (each grouping in 13%).

There is a dose-related trend for increased incidence for all of these (other than falls and behavioural symptoms). For the less common groupings, there is also evidence of a dose-related trend for hepatic function impairment.

The fact that several TEAEs appear to be dose related clearly indicates the desirability of utilising a minimal effective dose of MT.

Example 7—Effect of Cmax on Treatment Effects Using Other Scales

From the data available, the Cmax effect was not seen when assessing Temporal lobe FDG-PET decline. For this measure it appeared that high dose LMTM (pooled 200 mg/day) actually attenuated benefit otherwise seen for LMTM monotherapy, although some monotherapy benefit remained (results not shown).

From the data available, the Cmax effect was not seen when assessing outcome measures: Alzheimer's Disease Cooperative Study Activities of Daily Living (ADCS-ADL) decline.

Example 8—Providing an Optimised Dosage Regimen in AD Subject Populations

In summary a PK model has been developed on the basis of data from closely-sampled Phase 1 studies. From this per-subject steady state Cmax was estimated and used to split patients taking 8 mg/day dose into high (above median) and low (below median) Cmax groups. Unexpectedly, High and low Cmax groups differed in cognitive decline (as assessed using ADAS-cog) by ~2.5 units, with the effect being was observed in both monotherapy and add-on treatment groups. Interestingly there was evidence of an inverse dose-response relationship for FDG-PET at high doses.

Thus treatment response is determined by two factors:
1 Monotherapy vs add-on treatment status
2 Plasma concentration, which will vary in subject populations even for a given dose.

For both groups (mono-therapy and add-on) there is therefore benefit in dosing at sufficient level to maximise the proportion of subjects in the high Cmax group (while also avoiding high dosages which have a less desirable clinical profile). FIG. 5 estimates the proportion of subjects expected to be in the high Cmax group according to dose.

By way of illustration:
At 4 mg bid, 50% of subjects above Cmax threshold, with a predicted treatment effect relative to placebo ~5 ADAS-cog units over 65 weeks
By utilising at least 16 mg bid, or more preferably ~20 mg/day (10 mg bid), for which the estimated proportion is ~100%, even higher ADAS-cog treatment effects may be seen.

Thus, based on FIG. 5, a dosage regimen of higher than 4 mg bid is desirable. However there is likely to be little benefit in exceeding around 20 mg bid (40 mg total), since at that level it is estimated that the vast majority of the treated subjects will be in the high Cmax group irrespective of whether the dose is split.

There are at least two distinct reasons for wanting to use the minimal concentration which maximises the cognitive benefit treatment effect. Firstly TEAEs, most notably GI events, renal and urinary disorders including infections, and haemolytic anaemia, occurred in a dose-related fashion. Hence avoiding higher dosages than are necessary is clearly desirable in order to maintain an optimal clinical profile. Secondly, there is evidence of an inverse dose-response relationship for FDG-PET at high doses i.e. that benefit may actually be attenuated at high doses.

Overall these novel findings indicate that there is benefit in using slightly higher "low dose" LMT treatments than had previously been assumed, and further indicate that LMT treatments can be used as add-on to symptomatic treatments (albeit with less effect than for monotherapy).

Example 9—Providing an Optimised Dosage Regimen in bvFTD Subject Populations

The trial design for the Phase 3 trial of LMTM in behavioural variant frontotemporal dementia (bvFTD) is described in Examples 3 to 10 of WO2018/041739, which Examples also discuss those results. The disclosure of those Examples is specifically incorporated herein by reference.

It was concluded in WO2018/041739 that there was less cognitive decline (as assessed using ACE-R) seen at 4 mg b.i.d. and 100 mg b.i.d. than would have been predicted from historical studies. This could be explained if both the 4 mg b.i.d. (the "control" arm) and 100 mg b.i.d. (the "active" arm) demonstrated efficacy.

Furthermore AD-comedication status and severity were found to be significant covariates. Taking account of these covariates showed significant benefits on ACE-R in patients taking LMTM in combination with off-label AD treatments (acetylcholinesterase inhibitors and/or memantine) versus LMTM alone. There also appeared to be directionally supportive benefits on FAQ, MMSE and temporal volume.

The population PK model described above was used to estimate Cmax of parent MT in the patients in the bvFTD study. As with the AD trials described above, the median value at each dose was taken as a threshold for dividing patients into "High Cmax" and "Low Cmax" groups.

FIG. 6 shows the distribution of Cmax values in bvFTD. Vertical black line indicates median dividing low from high Cmax groups.

Figure 7:
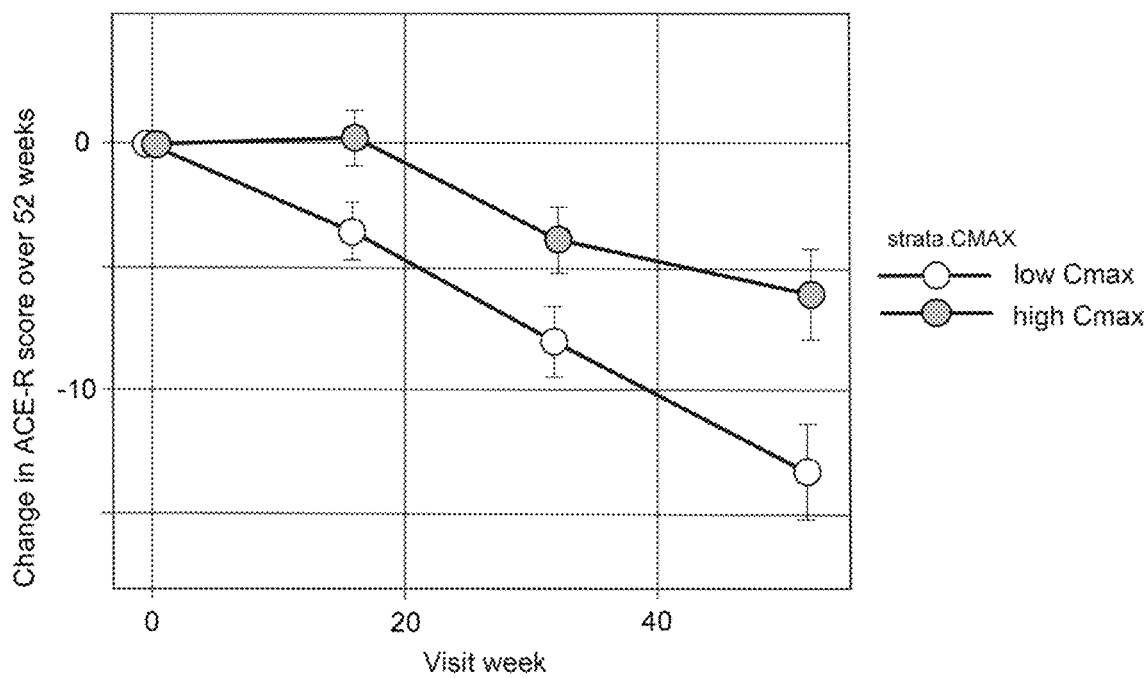

FIG. 7 shows the difference in decline on Addenbrooke's Cognitive Examination—revised (ACE-R) scale according to Cmax group in bvFTD patients receiving LMTM 8 mg/day as monotherapy. The decline in Cmax low group was found to be −13.3±1.8 (which is comparable to Kipps et al., (2008)=−15.3±1.4). However the decline in the Cmax high group was much reduced (−6.1±1.8). All efficacy analyses are based on an MMRM approach The difference between the low and high Cmax groups at 32 weeks was 4.2±2.0 (p=0.0389) and at 52 weeks 7.3±2.6 (p=0.0059).

Figure 8:
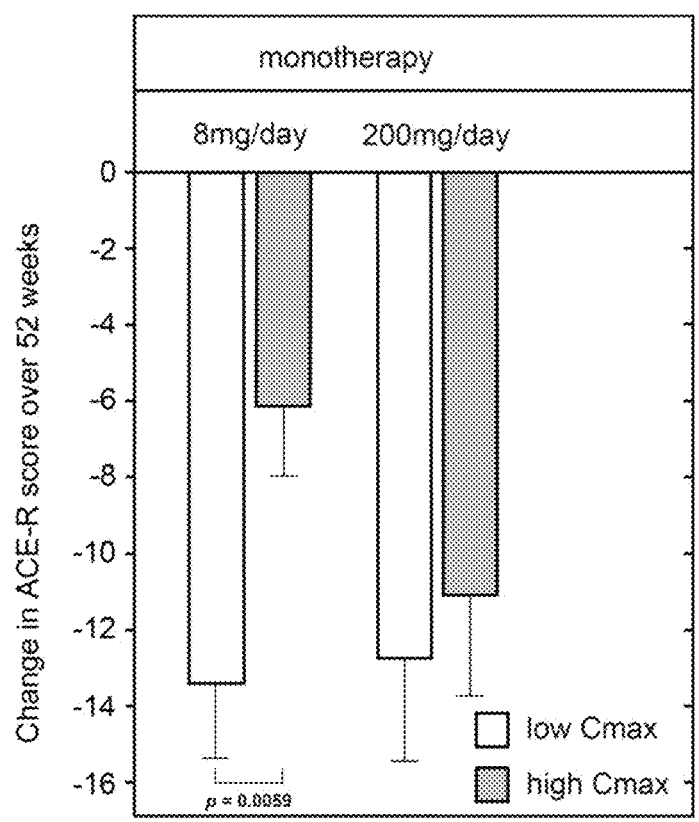

As illustrated in FIG. 8, highly significant difference between Cmax high/low groups for 8 mg/day. For 200 mg/day there appeared actually to be an inverse dose-response.

Figure 9:
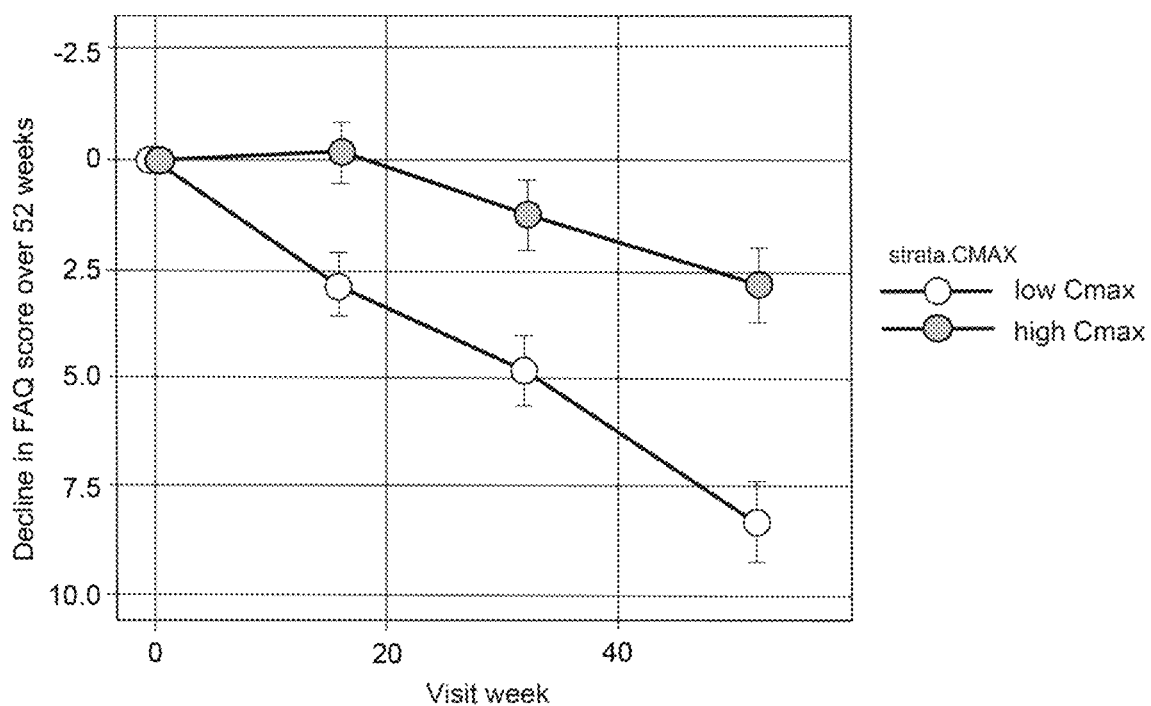

FIG. 9 shows the difference in decline on the Functional Activities Questionnaire (FAQ) scale according to Cmax group in bvFTD patients receiving LMTM 8 mg/day as monotherapy. Again decline was lower in the high C max group on this scale (decline in Cmax low group at 52 wk: 8.3±0.9; decline in Cmax high group at 52 wk: 2.9±0.9; difference at 32 weeks: −3.6±1.2 (p=0.0022); difference at 52 weeks: −5.4±1.3 (p<0.0001).

Figure 10:
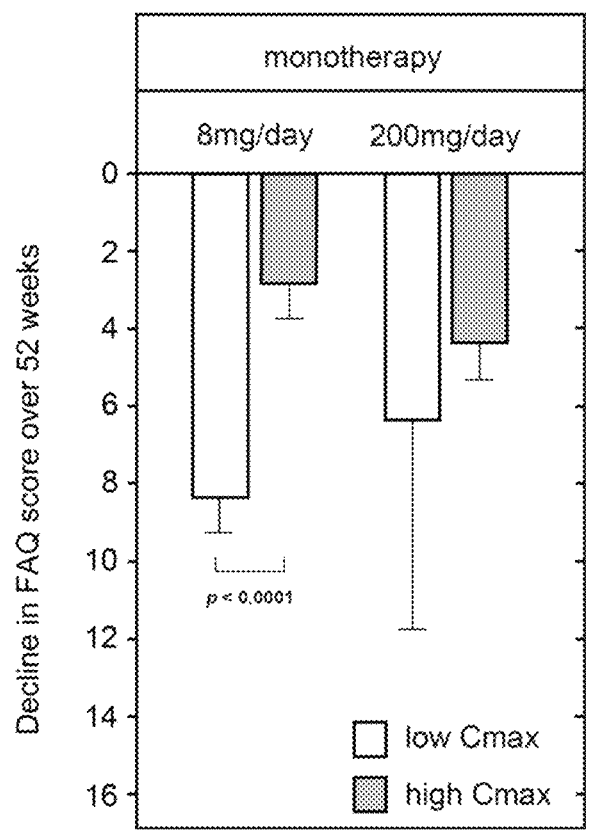

FIG. 10 illustrates that the FAQ benefit seen for high Cmax at 8 mg/day is greatly reduced at 200 mg/day. Furthermore there is an inverse dose-response so that the overall benefit is reduced for 200 mg/day.

Figure 11A:
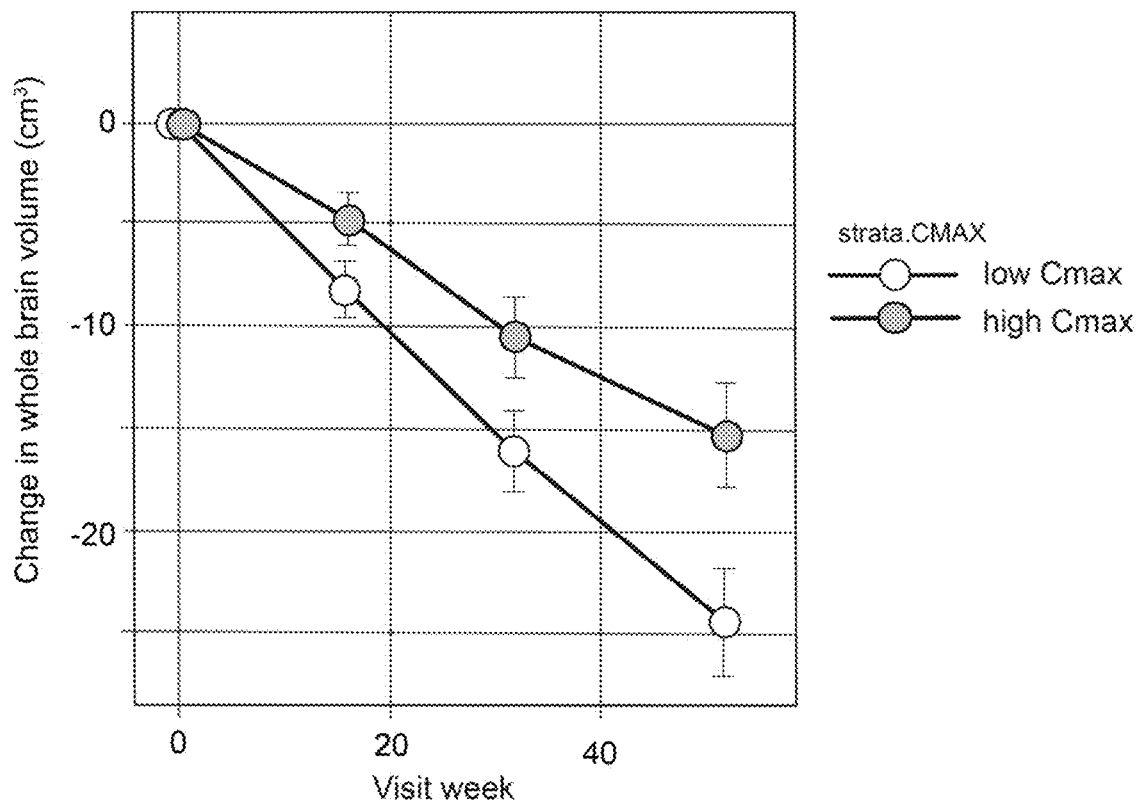
Figure 11B:
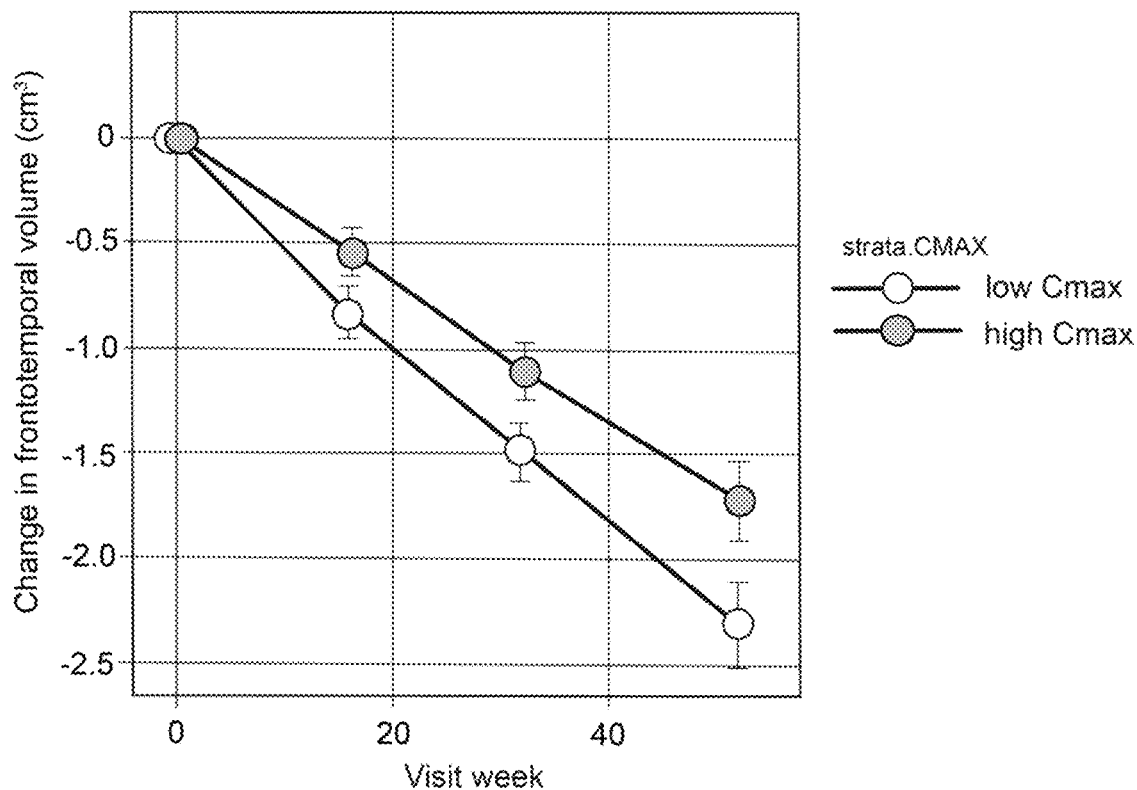
Figure 11C:
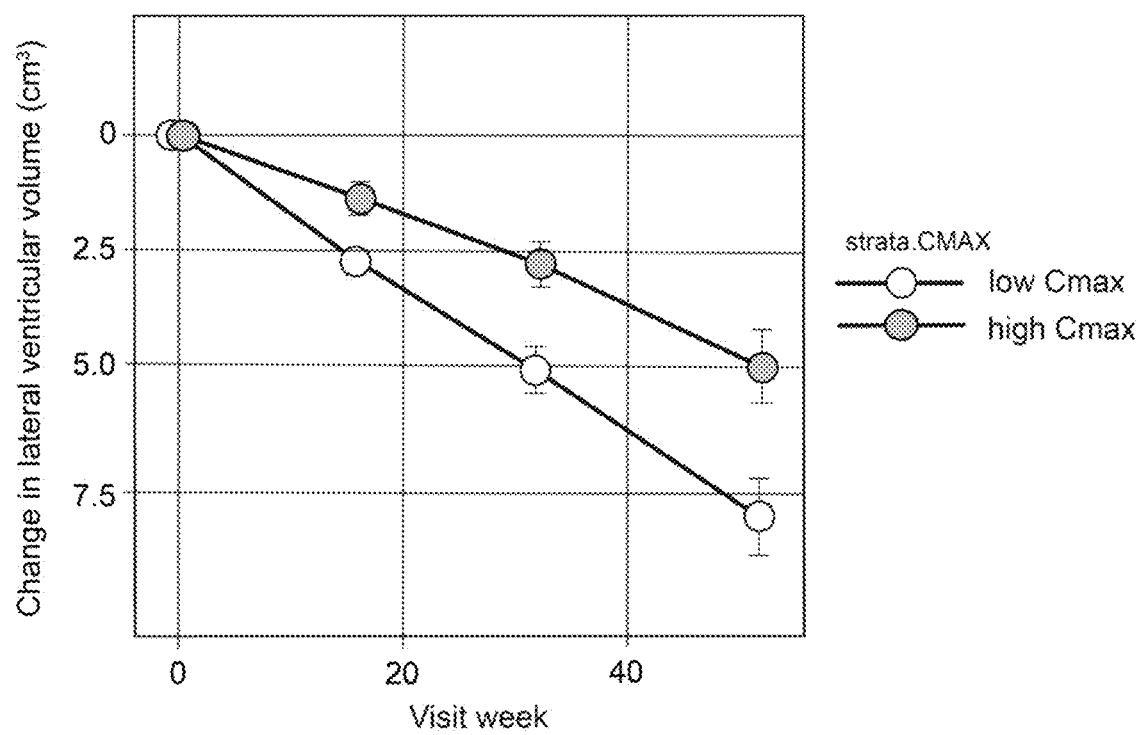

FIGS. 11*a*, 11*b* and 11*c* shows the corresponding changes in whole brain volume (WBV), temporal atrophy and lateral ventricular volume (LVV) in bvFTD patients.

For WBV in FIG. 11*a* the decline in Cmax low group at 52 wk was −24.5±2.6 ($cm^3$). The decline in the Cmax high group at 52 wk was −15.3±2.5. The difference at 52 weeks was 9.2±3.5 (p=0.0089).

FIG. 11*b* shows the difference in progression fronto-temporal atrophy according to Cmax group in bvFTD patients receiving LMTM 8 mg/day as mono (decline in Cmax low group at 52 wk: −2.3±0.2 ($cm^3$); decline in Cmax high group at 52 wk: −1.7±0.2; difference at 52 weeks: 0.6±0.3 (p=0.0247)).

FIG. 11*c* difference in ventricular expansion according to Cmax group in patients receiving LMTM 8 mg/day as mono (increase in Cmax low group at 52 wk: 8.3±0.8 ($cm^3$); increase in Cmax high group at 52 wk: 5.0±0.8; difference at 52 weeks: −3.3±1.1 (p=0.0027)).

Interestingly, in ACE-R, there was again an inverse dose-response for high dose, 200 mg/day.

As was concluded in WO2018/041739, this further analysis confirmed additional benefit from combination with symptomatic treatments, with triple therapy (MT, acetylcholinesterase inhibitors and memantine) potentially offering benefits. For the combined therapy the benefit of exceeding Cmax (in relation to ACE-R and FAQ) could not be confirmed, having regard to the smaller groups and hence larger error bars in the estimates (data not shown). Furthermore the same data indicated that the addition of symptomatic treatments overcomes high dose impairment (inverse dose response), at least in relation to these scales (data not shown). Significant MRI volumetric benefits for Cmax were best seen as add-on therapy (data not shown).

These results confirmed the concentration-response relationship for 8 mg/day monotherapy for cognitive function in bvFTD similar to that seen in AD. There was also a concentration-response relationship for 8 mg/day monotherapy on functional FAQ scale in bvFTD and an inverse dose-response for high dose monotherapy (i.e. 200 mg/day was worse than 8 mg/day).

Overall, a low dose administered in a regimen ensuring high Cmax (e.g. ~20 mg/day (10 mg bid)) appears to be an optimal monotherapy treatment for bvFTD.

However, as previously seen, and in contrast to AD, there is an additional benefit from combination with symptomatic treatments, which can particularly be seen in the low Cmax group.

In light of these factors one regimen may be starting with LMTX monotherapy at 8 mg/day and then increasing dose to ~20 mg/day, with the possibility of adding AD symptomatic treatments in bvFTD as the disease progresses.

Example 10—Further Analyses in Relation to Optimised Dosage Regimen in AD Subject Populations A more informative approach which permits statistical analyses to be conducted is to categorise patients receiving LMTM at a dose of 8 mg/day on the basis of $C_{max,ss}$ using a threshold that defines the upper limit of the lowest 35% of patients, corresponding to the 35% of patients with plasma levels below the validated limit of quantitation (0.2-10 ng/ml; N=208) following the first dose on day 1. That threshold was <0.373 ng/mL.

The remaining 65% were categorized into three $C_{max,ss}$ groups of comparable size (N ~128 per group) to permit better visualisation of the concentration-response relationship. Higher doses were grouped according to dose (N=187-329 per group). The model-based estimates of plasma exposure in these groups, as well as the higher doses, are shown in the Table EX3 below:

TABLE EX3

Plasma-modelled parent MT $C_{max,ss}$ for all patients with available plasma data in studies TRx-237-015 and TRx-237-005 according to either plasma $C_{max,ss}$ subgroups (LMTM, 8 mg/day) or dose (LMTM, 150-250 mg/day):

| Dose groups | n (%) | $C_{max,ss}$ (ng/mL) Mean (SD) | Range |
|---|---|---|---|
| 8 mg/day - Group 1 | 208 (35%) | 0.334 (0.0251) | 0.257-0.373 |
| 8 mg/day - Group 2 | 127 (21%) | 0.393 (0.0125) | 0.373-0.414 |
| 8 mg/day - Group 3 | 129 (22%) | 0.449 (0.0189) | 0.415-0.478 |
| 8 mg/day - Group 4 | 128 (22%) | 0.565 (0.0810) | 0.479-0.812 |
| 150 mg/day | 188 (100%) | 7.820 (1.787) | 5.099-18.611 |
| 200 mg/day | 329 (100%) | 10.126 (2.374) | 6.557-21.291 |
| 250 mg/day | 187 (100%) | 12.573 (2.460) | 8.833-21.188 |

Least squares mean and standard error estimates for change in $ADAS-cog_{11}$, $ADCS-ADL_{23}$, LVV, and WBV show clear concentration-responses as a function of $C_{max,ss}$ grouping in patients receiving LMTM at a dose of 8 mg/day (FIG. 13). There is a general tendency for outcomes to be worse at the high exposure levels associated with doses in the range 150-250 mg/day, implying the existence of a biphasic dose-response.

Example 11—Analyses Based on Critical Therapeutic $C_{max,ss}$ Threshold of 0.393 Ng/Ml in Relation to Optimised Dosage Regimen in AD Subject Populations Based on splitting of patients according to the threshold of 0.373 ng/ml, the treatment difference in patients receiving the 8 mg/day dose is −3.4 ADAS-cog units (see Table EX4 below; cf. Example 8 concerning median split showing about ~2 to 3 ADAS-cog units):

TABLE EX4

|  | A. All patients split by $C_{max,ss}$ 0.373 ng/mL | | | | | B. Patients receiving LMTM, 8 mg/day, split by $C_{max,ss}$ 0.373 ng/mL | | | | |
| --- | --- | --- | --- | --- | --- | --- | --- | --- | --- | --- |
|  | Difference ± SEM | CI | p-value | $N_{low}$ | $N_{high}$ | Difference ± SEM | CI | p-value | $N_{low}$ | $N_{high}$ |
| ADAS-cog | −2.99 ± 0.67 | −4.32 − −1.67 | <0.0001 | 193 | 969 | −3.41 ± 0.76 | −4.89 − −1.92 | <0.0001 | 193 | 373 |
| ADCS-ADL | 0.54 ± 0.94 | −1.30 − 2.38 | 0.5634 | 192 | 967 | 1.22 ± 1.01 | −0.77 − 3.21 | 0.2283 | 192 | 373 |
| LVV (cm$^3$) | −1.52 ± 0.34 | −2.18 − −0.83 | <0.0001 | 184 | 863 | −1.78 ± 0.38 | −2.53 − −1.03 | <0.0001 | 184 | 335 |
| WBV (cm$^3$) | 3.55 ± 1.06 | 1.48 − 5.62 | 0.0008 | 180 | 859 | 4.39 ± 1.18 | 2.07 − 6.71 | 0.0002 | 180 | 332 |

The corresponding longitudinal trajectories over 65 weeks according to $C_{max,ss}$ above or below the threshold value of 0.373 ng/mL are shown in FIG. 14.

Since only 65% of patients receiving the 8 mg/day have plasma concentrations above the threshold required for significant treatment benefit, it is desirable to determine the minimum dose at which 100% patients would be expected to have plasma levels within the therapeutic range. Given the population variability observed in the large available data set, it was possible to estimate the expected percentage of patients above the critical therapeutic threshold for $C_{max,ss}$ (0.393 ng/ml) and $C_{ave,ss}$ (0.223 ng/ml) according to once daily (QD) and twice daily (BID) dosing regimes. As can be seen in FIG. 15, using either criterion and dosing regime, LMTM needs to be given at a dose of at least 16 mg/day for 100% of patients to have plasma levels in the therapeutic range.

Example 12—Incorporation of Discriminator Between Monotherapy and Add-on Therapy A further consideration is whether patients are dosed with LMTM alone or in combination with approved treatments for AD (AChEIs and/or memantine). Patients receiving the 8 mg/day dose were examined further according co-medication status with these drugs. As can be seen in the Table EX5 below, the differences between patients having steady-state plasma levels below or above a threshold of 0.373 ng/ml reach statistical significance whether LMTM is taken as monotherapy or as add-on therapy on cognitive (ADAS-cog) and brain atrophy (LVV and WBV) endpoints.

TABLE EX5

Comparison of AD patients receiving LMTM, 8 mg/day, with $C_{max,ss}$ above or below parent MT threshold of 0.373 ng/mL: categorized according to AChEI and/or memantine use status at baseline.

|  | LMTM, 8 mg/day, as monotherapy | | | | | LMTM, 8 mg/day, as add-on therapy | | | | |
| --- | --- | --- | --- | --- | --- | --- | --- | --- | --- | --- |
|  | Difference ± SEM | CI | p-value | $N_{low}$ | $N_{high}$ | Difference ± SEM | CI | p-value | $N_{low}$ | $N_{high}$ |
| ADAS-cog$_{11}$ | −2.60 ± 1.16 | −4.88 − −0.33 | 0.0251 | 33 | 67 | −3.52 ± 0.78 | −5.05 − −2.00 | <0.0001 | 160 | 306 |
| ADCS-ADL$_{23}$ | 0.46 ± 1.47 | −2.43 − 3.34 | 0.7552 | 32 | 67 | 1.32 ± 1.04 | −0.71 − 3.36 | 0.2016 | 160 | 306 |
| LVV (cm$^3$) | −1.46 ± 0.45 | −2.33 − −0.58 | 0.0011 | 33 | 61 | −1.35 ± 0.37 | −2.08 − −0.62 | 0.0003 | 151 | 274 |
| WBV (cm$^3$) | 2.76 ± 1.66 | −0.49 − 6.01 | 0.0966 | 32 | 61 | 4.69 ± 1.21 | 2.32 − 7.06 | 0.0001 | 148 | 271 |

The corresponding longitudinal trajectories over 65 weeks are illustrated below for ADAS-cog$_{11}$, ADCS-ADL$_{23}$, LVV and WBV in FIG. 16.

Example 13—Analysis of ADAS-Cog$_{11}$ Decline Vs. Plasma Concentration

A further analysis of ADAS-cog decline over 65 weeks was undertaken using a modified form of the Hill equation (Wagner, 1968) in order to estimate the minimum and maximum plasma concentrations for expected treatment response over 65 weeks. The Hill equation was applied under the assumption of non-cooperativity and used an imposed overall zero where there was no-effect level was taken as 11 units at a $C_{max,ss}$ concentration of 0.29 ng/ml based on visual inspection of the data. Use of different limiting values did not meaningfully change the results. In addition, a linear term was added to permit trends occurring at high concentrations to be included in the model using data for doses in the range 150-250 mg/day. The expanded Hill equation was applied to the data in the form:

$$\text{change in parameter} = E_{min} - (E_{max}*([C]-0.29))/(EC_{50} + ([C]-0.29)) + (A*([C]-0.29))$$

where $E_{min}$ is the imposed zero value, $E_{max}$ is the maximum treatment effect assumed in the standard Hill equation, $EC_{50}$ is the $C_{max,ss}$ at which the treatment effect is 50% of the maximum assumed in the standard Hill equation and A is a further linear term estimated by the model to take account of a potential biphasic response. $C_{max,ss}$ was also expressed as the estimated equivalent mean dose using a relationship obtained by fitting a linear model to the mean plasma concentrations at the 8, 150, 200 and 250 mg/day doses:

$$\text{estimated dose (mg/day)} = 0.045*C_{max,ss} + 0.016$$

As can be seen from FIG. 17, there is an overall biphasic concentration-response for LMTM taken alone or in combination with symptomatic treatments. The dose range in which the treatment response is estimated to be maximal is 20-60 mg/day.

Compared with monotherapy, the estimated maximum treatment is reduced by about 4 ADAS-cog units when LMTM is combined with symptomatic treatments. A further effect is to shift the $C_{max,ss}$ concentration required for half-maximal treatment response to the right from 0.32±0.01 ng/ml to 0.40±0.05 ng/ml.

It will be apparent that the effects of plasma concentration and co-medication status are additive. This permits an overall estimate of treatment benefit comparing patients receiving the 8 mg/day dose as monotherapy and having plasma levels above the threshold of 0.373 ng/ml with patients receiving the same dose in combination with symptomatic treatments and having plasma levels below this threshold. As can be seen from FIG. 17, the latter group comes nearest to approximating the minimum measurable treatment response. This analysis shows that treatment effect for the 8 mg/day dose as monotherapy in patients with therapeutic plasma levels of the drug is −7.53 (CI −9.93 − −5.13, p<0.0001) ADAS-cog$_{11}$ units, with corresponding treatment effects for ADCS-ADL$_{23}$, LVV and WBV (Table EX6 below):

TABLE EX6

Comparison of LMTM as add-on versus monotherapy and between low $C_{max}$ add-on and high $C_{max}$ monotherapy.

| | Comparison of LMTM, 8 mg/day, low $C_{max}$ add-on vs high $C_{max}$ monotherapy | | | | |
|---|---|---|---|---|---|
| | Difference ± SEM | CI | p-value | $N_{low, add-on}$ | $N_{high, mono}$ |
| ADAS-cog11 | −7.53 ± 1.22 | −9.93−−5.13 | <0.0001 | 160 | 67 |
| ADCS-ADL23 | 6.14 ± 1.64 | 2.93-9.34 | 0.0002 | 160 | 67 |
| LVV (cm$^3$) | −3.15 ± 0.62 | −4.37−−1.93 | <0.0001 | 151 | 61 |
| WBV (cm$^3$) | 11.54 ± 1.87 | 7.88-15.21 | <0.0001 | 148 | 61 |

Example 14—Implications of Findings Relating to Monotherapy Vs. Add-on Therapy in Relation to Dosing Regimens As is evident from the foregoing, there is a reduction in the maximum effect of LMTM when it is combined with symptomatic treatments. It should be noted however, that this relates to a context in which patients have received LMTM against a background of chronic pre-treatment with symptomatic drugs. The mechanism of this has been elucidated in a series of experiments in a well characterised tau transgenic mouse model. If these animals are pretreated chronically with a cholinesterase inhibitor (rivastigmine), almost all of the neurobiological effects seen when LMTM is administered alone are reduced or eliminated entirely, leading to elimination of the beneficial effect of LMTM on spatial learning memory. Pre-treatment with memantine likewise eliminated the effect on spatial learning memory (results not shown).

The mechanism appears to be a generalised homeostatic downregulation affecting many synaptic and neurotransmitter systems in the brain that counteracts the activating effects of the symptomatic drugs. Thus, LMTM-induced effects are subject to dynamic downregulation if the brain is already subject to prior chronic stimulation by symptomatic treatments.

Example 15—Further Analysis in Relation to Providing an Optimised Dosage Regimen in FTD Subject Populations The cut-off that defined the upper limit of the lowest 35% group (corresponding to the percentage of patients with plasma levels below the validated limit of quantitation in Day 1) was 0.346 ng/ml for the bvFTD population.

As for AD (see Example 10) the remainder with Day 1 plasma levels within the validated range of quantitation at the 8 mg/day dose were distributed in 3 groups having approximately equal numbers (22% each; see Table EX7 below).

TABLE EX7

Plasma-modelled parent MT $C_{max,\,ss}$ for LMTM groups

| Dose groups | n (%) | $C_{max,\,ss}$ (ng/mL) Mean (SD) | Range |
|---|---|---|---|
| 8 mg/day | | | |
| 8 mg/day - Group 1 | 32 (35%) | 0.321 (0.0198) | 0.281-0.346 |
| 8 mg/day - Group 2 | 20 (22%) | 0.355 (0.0082) | 0.346-0.372 |
| 8 mg/day - Group 3 | 19 (21%) | 0.387 (0.0121) | 0.373-0.409 |
| 8 mg/day - Group 4 | 20 (22%) | 0.470 (0.0537) | 0.413-0.583 |
| 200 mg/day | 81 | 9.040 (1.6259) | 6.800-14.235 |

There is a similar concentration-response relationship for measures of progression of brain atrophy by MRI (fronto-temporal volume, lateral ventricular volume, whole brain volume). This is shown in FIG. 18.

Alternative efficacy analyses were performed in which the group of patients with minimal systemic exposure to the drug was used as a proxy for placebo. These are shown in the Table EX8 below and illustrated in FIG. 19.

Example 16—Analysis of Chance in Outcomes Vs. Plasma Concentration

As can be seen from FIG. 18 above, treatment effects were worse at the high dose of 200 mg/day on all outcomes, implying a biphasic concentration-response relationship in bvFTD.

As for AD, an expanded Hill equation was applied under the assumption of non-cooperativity and used imposed overall zero values where the no-effect level was taken as −12 ACE-R units, 8 FAQ units or −30 cm³ for whole brain volume at a $C_{max,ss}$ concentration of 0.29 ng/ml based on visual inspection of the data. Use of different limiting values did not meaningfully change the results. In addition, a linear term was added to permit trends occurring at high concentrations to be included in the model using mean decline occurring at the 200 mg/day dose.

The expanded Hill equation provided a robust fit to the mean concentration-response for change in ACE-R, FAQ and whole brain volume over 52 weeks. The model fit for all outcomes is consistent with the assumption that the lower limiting plasma concentration required for treatment response is 0.29 ng/ml in patients receiving the 8 mg/day dose. Subgrouping the whole brain volume data in patients receiving the 200 mg/day dose into terciles (FIG. 20) made it possible to estimate the maximum limiting concentration at which the treatment effect was lost, namely 13.57 ng/ml (corresponding to a predicted dose of 301 mg/day).

TABLE EX8

Comparison of patients categorized by above ("high") or below ("low") parent MT threshold of 0.346 ng/mL

| | All patients | | | | | Patients receiving LMTM 8 mg/day | | | | | |
|---|---|---|---|---|---|---|---|---|---|---|---|
| | Difference ± SEM for $C_{max,ss}$ > 0.346 ng/ml | CI | p-value | $N_{low}$ | $N_{high}$ | Difference ± SEM for $C_{max,ss}$ > 0.346 ng/ml | CI | p-value | $N_{low}$ | $N_{high}$ | Decline ± SEM for $C_{max,ss}$ ≤ 0.346 ng/ml |
| ACE-R | 1.37 ± 2.60 | −3.73 – 6.47 | 0.5973 | 31 | 125 | 5.06 ± 2.62 | −0.08 – 10.21 | 0.0536 | 31 | 57 | −11.33 ± 2.09 |
| FAQ | −2.98 ± 1.10 | −5.15 – −0.82 | 0.0069 | 31 | 114 | −3.27 ± 1.32 | −5.85 – −0.69 | 0.0131 | 31 | 57 | 7.13 ± 1.06 |
| WBV (cm³) | 9.05 ± 3.06 | 3.06 – 15.04 | 0.0031 | 28 | 112 | 11.67 ± 3.41 | 5.00 – 18.36 | 0.0006 | 28 | 51 | −27.72 ± 2.73 |
| LVV (cm³) | −3.41 ± −0.95 | −5.27 – −1.55 | 0.0003 | 28 | 104 | −4.12 ± 1.06 | −6.19 – −2.05 | <0.0001 | 28 | 45 | 9.13 ± 0.82 |
| FTV (cm³) | 0.73 ± 0.24 | 0.26 – 1.19 | 0.0023 | 28 | 112 | 0.72 ± 0.27 | 0.19 – 1.26 | 0.0076 | 28 | 51 | −2.47 ± 0.22 |

REFERENCES FOR DISCUSSION OF BACKGROUND ART

Alzheimer A. Über eine eigenartige Erkrankung der Hirnrinde. *Allg Z Psych Psych-gerich Med* 1907; 64:146-8 [German].

Alzheimer's Disease International. World Alzheimer Report 2015: The global impact of dementia, an analysis of prevalence, incidence, cost and trends. *World Alzheimer Report* 2015.

Arriagada P W, Growdon J H, Hedley-White E T, Hyman B T. Neurofibrillary tangles but not senile plaques parallel duration and severity of Alzheimer's disease. *Neurology* 1992; 42: 631-9.

Baddeley T, C., McCaffrey J, Storey J M D, et al. Complex disposition of methylthioninium redox forms determines efficacy in tau aggregation inhibitor therapy for Alzheimer's disease. *J Pharmacol Exptl Therapeutics* 2015; 352: 110-8.

Braak H, Del Tredici K. The pathological process underlying Alzheimer's disease in individuals under thirty. *Acta Neuropathol* 2011; 121: 171-81.

Brier M R, Gordon B, Friedrichsen K, et al. Tau and As imaging, CSF measures, and cognition in Alzheimer's disease. *Science Transl Med* 2016; 8: 338ra66.

DiSanto A R, Wagner J G. Pharmacokinetics of highly ionized drugs. I I. Methylene blue—absorption, metabolism, and excretion in man and dog after oral administration. *J Pharmaceut Sci* 1972; 61: 1086-90.

Geerts H, Spiros A, Roberts P, Carr R. A strategy for developing new treatment paradigms for neuropsychiatric and neurocognitive symptoms in Alzheimer's disease. *Front Pharmacol* 2013; 4: 47.

Giannakopoulos P, Herrmann F R, Bussiere T, et al. Tangle and neuron numbers, but not amyloid load, predict cognitive status in Alzheimer's disease. *Neurology* 2003; 60: 1495-500.

Harrington C R, Storey JMD, Clunas S, et al. Cellular models of aggregation-dependent template-directed proteolysis to characterize tau aggregation inhibitors for treatment of Alzheimer's disease. *J Biol Chem* 2015; 290: 10862-75.

Huang Y, Mucke L. Alzheimer mechanisms and therapeutic strategies. *Cell* 2012; 148: 1204-22.

Josephs K A, Whitwell J L, Ahmed Z, et al. b-Amyloid burden is not associated with rates of brain atrophy. *Ann Neurol* 2008; 63: 204-12.

Lai R Y K, Harrington C R, Wischik C M. Absence of a role for phosphorylation in the tau pathology of Alzheimer's disease. *Biomolecules* 2016; 6: 19.

Maruyama M, Shimada H, Suhara T, et al. Imaging of tau pathology in a tauopathy mouse model and in Alzheimer patients compared to normal controls. *Neuron* 2013; 79: 1094-108.

May J M, Qu Z-c, Cobb C E. Reduction and uptake of methylene blue by human erythrocytes. *Am J Physiol—Cell Physiol* 2004; 286: C1390-8.

Melis V, Magbagbeolu M, Rickard J E, et al. Effects of oxidized and reduced forms of methylthioninium in two transgenic mouse tauopathy models. *Behav Pharmacol* 2015; 26: 353-68.

Mukaetova-Ladinska E B, Garcia-Sierra F, Hurt J, et al. Staging of cytoskeletal and b-amyloid changes in human isocortex reveals biphasic synaptic protein response during progression of Alzheimer's disease. *Am J Pathol* 2000; 157: 623-36.

Mullane K, Williams M. Alzheimer's therapeutics: Continued clinical failures question the validity of the amyloid hypothesis—but what lies beyond?*Biochem Pharmacol* 2013; 85: 289-305.

Peter C, Hongwan D, Küpfer A, Lauterburg B H. Pharmacokinetics and organ distribution of intravenous and oral methylene blue. *Eur J Clin Pharmacol* 2000; 56: 247-50.

Schneider A, Biernat J, von Bergen M, Mandelkow E, Mandelkow E-M. Phosphorylation that detaches tau protein from microtubules (Ser262, Ser214) also protects it against aggregation into Alzheimer paired helical filaments. *Biochemistry* 1999; 38: 3549-58.

Winblad B, Amouyel P, Andrieu S, et al. Defeating Alzheimer's disease and other dementias: a priority for European science and society. *Lancet Neurol* 2016; 15: 455-532.

Wischik C M, Crowther R A, Stewart M, Roth M. Subunit structure of paired helical filaments in Alzheimer's disease. *J Cell Biol* 1985; 100: 1905-12.

Wischik C M, Edwards P C, Lai R Y K, et al. Quantitative analysis of tau protein in paired helical filament preparations: implications for the role of tau protein phosphorylation in PHF assembly in Alzheimer's disease. *Neurobiol Aging* 1995; 16: 409-31.

Wischik C M, Edwards P C, Lai R Y K, Roth M, Harrington C R. Selective inhibition of Alzheimer disease-like tau aggregation by phenothiazines. *Proc Natl Acad Sci USA* 1996; 93:11213-8.

Wischik C M, Harrington C R, Storey JMD. Tau-aggregation inhibitor therapy for Alzheimer's disease. *Biochem Pharmacol* 2014; 88: 529-39.

Wischik C M, Novak M, Edwards P C, Klug A, Tichelaar W, Crowther R A. Structural characterization of the core of the paired helical filament of Alzheimer disease. *Proc Natl Acad Sci USA* 1988; 85: 4884-8.

Wischik C M, Novak M, Thogersen H C, et al. Isolation of a fragment of tau derived from the core of the paired helical filament of Alzheimer's disease. *Proc Natl Acad Sci USA* 1988; 85: 4506-10.

Wischik C M, Staff R T, Wischik D J, et al. Tau aggregation inhibitor therapy: an exploratory phase 2 study in mild or moderate Alzheimer's disease. *J Alzheimer's Dis* 2015; 44: 705-20.

Wischik C M, Wischik D J, Storey JMD, Harrington C R. Rationale for tau aggregation inhibitor therapy in Alzheimer's disease and other tauopathies. In: Martinez A, ed. Emerging drugs and targets for Alzheimer's disease Volume 1: Beta-amyloid, tau protein and glucose metabolism. Cambridge: Royal Society of Chemistry; 2010: 210-32.

REFERENCES FOR PROTEINS INVOLVED IN DISEASES OF PROTEIN AGGREGATION

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. *Human Genetics* 89, 377-380.

Andersen, P. (2006) Amyotrophic lateral sclerosis associated with mutations in the CuZn superoxide dismutase gene. *Current Neurology and Neuroscience Reports* 6, 37-46.

Arai, T., Hasegawa, M., Nonoka, T., Kametani, F., Yamashita, M., Hosokawa, M., Niizato, K., Tsuchiya, K., Kobayashi, Z., Ikeda, K., Yoshida, M., Onaya, M., Fujishiro, H. & Akiyama, H. (2010) Phosphorylated and cleaved TDP-43 in ALS, FTLD and other neurodegenerative disorders and in cellular models of TDP-43 proteinopathy. Neuropathology 30, 170-181.

Askanas, V., Engel, W. K. & Nogalska, A. (2009) Inclusion body myositis: a degenerative muscle disease associated with intra-muscle fiber multi-protein aggregates, proteasome inhibition, endoplasmic reticulum stress and decreased lysosomal degradation. Brain Pathology 19, 493-506.

Barmada, S. J., Skibinski, G., Korb, E., Rao, E. J., Wu, J. Y. & Finkbeiner, S. (2010) Cytoplasmic mislocalization of TDP-43 is toxic to neurons and enhanced by a mutation associated with familial amyotrophic lateral sclerosis. Journal of Neuroscience 30, 639-649.

Blair, I. P., Williams, K. L., Warraich, S. T., Durnall, J. C., Thoeng, A. D., Manavis, J., Blumbergs, P. C., Vucic, S., Kiernan, M. C. & Nicholson, G. A. (2010) FUS mutations in amyotrophic lateral sclerosis: clinical, pathological, neurophysiological and genetic analysis. Journal of Neurology Neurosurgery and Psychiatry 81, 639-645.

Booth, D. R., Sunde, M., Bellotti, V., Robinson, C. V., Hutchinson, W. L., Fraser, P. E., Hawkins, P. N., Dobson, C. M., Radford, S. E., Blake, C. C. F. & Pepys, M. B. (1997) Instability, unfolding and aggregation of human lysozyme variants underlying amyloid fibrillogenesis. Nature 385, 787-793.

Byrne, S., Walsh, C., Lynch, C., Bede, P., Elamin, M., Kenna, K., McLaughlin, R. & Hardiman, O. (2011) Rate of familial amyotrophic lateral sclerosis: a systematic review and meta-analysis. Journal of Neurology, Neurosurgery & Psychiatry 82, 623-627.

Carrell, R. W. & Gooptu, B. (1998) Conformational changes and disease—serpins, prions and Alzheimer's. *Current Opinion in Structural Biology* 8, 799-809.

Chen-Plotkin, A. S., Lee, V. M. Y. & Trojanowski, J. Q. (2010) TAR DNA-binding protein 43 in neurodegenerative disease. Nature Reviews Neurology 6, 211-220.

Chiti, F., Webster, P., Taddei, N., Clark, A., Stafani, M., Ramponi, G. & Dobson, C. (1999) Designing conditions for in vitro formation of amyloid protofilaments and fibrils. *Proceedings of the National Academy of Sciences*, USA 96, 3590-3594.

Cox, L. E., Ferraiuolo, L., Goodall, E. F., Heath, P. R., Higginbottom, A., Mortiboys, H., Hollinger, H. C., Hartley, J. A., Brockington, A., Burness, C. E., Morrison, K. E., Wharton, S. B., Grierson, A. J., Ince, P. G., Kirby, J. & Shaw, P. J. (2010) Mutations in CHMP2B in lower motor neuron predominant amyotrophic lateral sclerosis (ALS). PLOS One 5, e9872.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C.-M., Gooptu, B., Elliott, P. R., Finch, J. T., Carrell, R. W. & Lomas, D. A. (1999) Familial dementia caused by polymerization of mutant neuroserpin. Nature 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. Science 277, 1990-1993.

Dische, F. E., Wernstedt, C., Westermark, G. T., Westermark, P., Pepys, M. B., Rennie, J. A., Gilbey, S. G. & Watkins, P. J. (1988) Insulin as an amyloid-fibril protein at sites of repeated insulin injections in a diabetic patient. Diabetologia 31, 158-161.

Elden, A. C., Kim, H.-J., Hart, M. P., Chen-Plotkin, A. S., Johnson, B. S., Fang, X., Armakola, M., Geser, F., Greene, R., Lu, M. M., Padmanabhan, A., Clay-Falcone, D., McCluskey, L., Elman, L., Juhr, D., Gruber, P. J., Rub, U., Auburger, G., Trojanowski, J. Q., Lee, V. M. Y., Van Deerlin, V. M., Bonini, N. M. & Gitler, A. D. (2010) Ataxin-2 intermediate-length polyglutamine expansions are associated with increased risk for ALS. Nature 466, 1069-1075.

Finsterer, J (2009) Mitochondrial disorders, cognitive impairment and dementia. *J. Neurol. Sci.* 283:143-148

Gasset, M., Bladwin, M. A., Lloyd, D. H., Gabriel, J.-M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Gendron, T. F., Josephs, K. A. & Petrucelli, L. (2010) Review: Transactive response DNA– binding protein 43 (TDP-43): mechanisms of neurodegeneration. *Neuropathology and Applied Neurobiology* 36, 97-112.

Geser, F., Lee, V. M.-Y. & Trojanowski, J. Q. (2010) Amyotrophic lateral sclerosis and frontotemporal lobar degeneration: A spectrum of TDP-43 proteinopathies. Neuropathology 30, 103-112.

Gitcho, M. A., Baloh, R. H., Chakraverty, S., Mayo, K., Norton, J. B., Levitch, D., Hatanpaa, K. J., White, C. L., Ill, Bigio, E. H., Caselli, R., Baker, M., A I-Lozi, M. T., Morris, J. C., Pestronk, A., Rademakers, R., Goate, A. M. & Cairns, N. J. (2008) TDP-43 A315T mutation in familial motor neuron disease. Annals of Neurology 63, 535-538.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M.-C., Mullan, M., Brown, J., Crawford, F., Fidani, L., Giuffra, L., Haynes, A., Irving, N., James, L., Mant, R., Newton, P., Rooke, K., Roques, P., Talbot, C., Pericak-Vance, M., Roses, A., Williamson, R., Rossor, M., Owen, M. & Hardy, J. (1991) Segregation of a missense mutation in the amyloid precursor protein gene with familial Alzheimer's disease. Nature 349, 704-706.

Gorevic, P. D., Casey, T. T., Stone, W. J., DiRaimondo, C. R., Prelli, F. C. & Frangione, B. (1985) b-2 Microglobulin is an amyloidogenic protein in man. *Journal of Clinical Investigation* 76, 2425-2429.

Gustavsson, A., Engström, U. & Westermark, P. (1991) Normal transthyretin and synthetic transthyretin fragments form amyloid-like fibrils in vitro. *Biochemical and Biophysical Research Communications* 175, 1159-1164.

Higashi, S., Tsuchiya, Y., Araki, T., Wada, K. & Kabuta, T. (2010) TDP-43 physically interacts with amyotrophic lateral sclerosis-linked mutant CuZn superoxide dismutase. Neurochemistry International 57, 906-913.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, B. A., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Igaz, L. M., Kwong, L. K., Chen-Plotkin, A., Winton, M. J., Unger, T. L., Xu, Y., Neumann, M., Trojanowski, J. Q. & Lee, V. M. Y. (2009) Expression of TDP-43 C-terminal fragments in vitro recapitulates pathological features of TDP-43 proteinopathies. Journal of Biological Chemistry 284, 8516-8524.

Jinwal, U K, Miyata, Y, Koren, J, Ill, Jones, J R, Trotter, J H et al. (2009) Chemical manipulation of Hsp70 ATPase activity regulates tau stability. *J. Neurosci.* 29:12079-12088

Johansson, B., Wernstedt, C. & Westermark, P. (1987) Atrial natriuretic peptide deposited as atrial amyloid fibrils. *Biochemical and Biophysical Research Communications* 148, 1087-1092.

Johnson, B. S., McCaffery, J. M., Lindquist, S. & Gitler, A. D. (2008) A yeast TDP-43 proteinopathy model: Exploring the molecular determinants of TDP-43 aggregation and cellular toxicity. Proceedings of the National Academy of Sciences 105, 6439-6444.

Johnson, B. S., Snead, D., Lee, J. J., McCaffery, J. M., Shorter, J. & Gitler, A. D. (2009) TDP-43 is intrinsically aggregation-prone, and amyotrophic lateral sclerosis-linked mutations accelerate aggregation and increase toxicity. Journal of Biological Chemistry 284, 20329-20339.

Johnson, J. O., Mandrioli, J., Benatar, M., Abramzon, Y., Van Deerlin, V. M., Trojanowski, J. Q., Gibbs, J. R., Brunetti, M., Gronka, S., Wuu, J., Ding, J., McCluskey, L., Martinez-Lage, M., Falcone, D., Hernandez, D. G., Arepalli, S., Chong, S., Schymick, J. C., Rothstein, J., Landi, F., Wang, Y.-D., Calvo, A., Mora, G., Sabatelli, M., Monsurro, M. R., Battistini, S., Salvi, F., Spataro, R., Sola, P., Borghero, G., Galassi, G., Scholz, S. W., Taylor, J. P., Restagno, G., Chib, A. & Traynor, B. J. (2010) Exome sequencing reveals VCP mutations as a cause of familial ALS. Neuron 68, 857-864.

Kabashi, E., Lin, L., Tradewell, M. L., Dion, P. A., Bercier, V., Bourgouin, P., Rochefort, D., Bel Hadj, S., Durham, H. D., Velde, C. V., Rouleau, G. A. & Drapeau, P. (2010) Gain and loss of function of ALS-related mutations of TARDBP (TDP-43) cause motor deficits in vivo. Human Molecular Genetics 19, 671-683.

Kabashi, E., Valdmanis, P. N., Dion, P., Spiegelman, D., McConkey, B. J., Velde, C. V., Bouchard, J.-P., Lacomblez, L., Pochigaeva, K., Salachas, F., Pradat, P.-F., Camu, W., Meininger, V., Dupre, N. & Rouleau, G. A. (2008) TARDBP mutations in individuals with sporadic and familial amyotrophic lateral sclerosis. Nature Genetics 40, 572-574.

Ling, S.-C., Albuquerque, C. P., Han, J. S., Lagier-Tourenne, C., Tokunaga, S., Zhou, H. & Cleveland, D. W. (2010) ALS-associated mutations in TDP-43 increase its stability and promote TDP-43 complexes with FUS/TLS. Proceedings of the National Academy of Sciences 107, 13318-13323.

Lomas, D. A., Evans, D. L., Finch, J. T. & Carrell, R. W. (1992) The mechanism of Z a1-antitrypsin accumulation in the liver. *Nature* 357, 605-607.

Love, S., Bridges, L. R. & Case, C. P. (1995) Neurofibrillary tangles in Niemann-Pick disease type C. Brain 118, 119-129.

Mackenzie, I. R. A., Bigio, E. H., Ince, P. G., Geser, F., Neumann, M., Cairns, N. J., Kwong, L. K., Forman, M. S., Ravits, J., Stewart, H., Eisen, A., McClusky, L., Kretzschmar, H. A., Monoranu, C. M., Highley, J. R., Kirby, J., Siddique, T., Shaw, P. J., Lee, V. M. Y. & Trojanowski, J. Q. (2007) Pathological TDP-43 distinguishes sporadic amyotrophic lateral sclerosis from amyotrophic lateral sclerosis with SOD1 mutations. Annals of Neurology 61, 427-434.

Mackenzie, I. R. A., Rademakers, R. & Neumann, M. (2010) TDP-43 and FUS in amyotrophic lateral sclerosis and frontotemporal dementia. *The Lancet Neurology* 9, 995-1007.

Maury, C. P. & Baumann, M. (1990) Isolation and characterization of cardiac amyloid in familial amyloid polyneuropathy type I V (Finnish): relation of the amyloid protein to variant gelsolin. *Biochimica et Biophysica Acta* 1096, 84-86.

Neary, D., Snowden, J. S., Gustafson, L., Passant, U., Stuss, D., Black, S., Freedman, M., Kertesz, A., Robert, P. H., Albert, M., Boone, K., Miller, B. L., Cummings, J. & Benson, D. F. (1998) Frontotemporal lobar degeneration: a consensus on clinical diagnostic criteria. Neurology 51, 1546-1554.

Neumann, M. (2009) Molecular neuropathology of TDP-43 proteinopathies. International Journal of Molecular Sciences 10, 232-246.

Neumann, M., Sampathu, D. M., Kwong, L. K., Truax, A. C., Micsenyi, M. C., Chou, T. T., Bruce, J., Schuck, T., Grossman, M., Clark, C. M., McCluskey, L. F., Miller, B. L., Masliah, E., Mackenzie, I. R., Feldman, H., Feiden, W., Kretzschmar, H. A., Trojanowski, J. Q. & Lee, V. M. Y. (2006) Ubiquitinated TDP-43 in frontotemporal lobar degeneration and amyotrophic lateral sclerosis. Science 314, 130-133.

Nonaka, T., Kametani, F., Arai, T., Akiyama, H. & Hasegawa, M. (2009) Truncation and pathogenic mutations facilitate the formation of intracellular aggregates of TDP-43. Human Molecular Genetics 18, 3353-3364.

Ohmi, K., Kudo, L. C., Ryazantsev, S., Zhao, H.-Z., Karsten, S. L. & Neufeld, E. F. (2009) Sanfilippo syndrome type B, a lysosomal storage disease, is also a tauopathy. Proceedings of the National Academy of Sciences 106, 8332-8337.

Orr, H. T. & Zoghbi, H. Y. (2007) Trinucleotide repeat disorders. *Annual Review of Neuroscience* 30, 575-621.

Paulson, H. L. (1999) Human genetics '99: trinucleotide repeats. *American Journal of Human Genetics* 64, 339-345.

Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. & Hsuan, J. J. (1993) Human lysozyme gene mutations cause hereditary systemic amyloidosis. *Nature* 362, 553-557.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin, R. C., Di lorio, G., Golbe, L. I. & Nussbaum, R. L. (1997) Mutation in the a-synuclein gene identified in families with Parkinson's disease. *Science* 276, 2045-2047.

Prusiner, S. B., Scott, M. R., DeArmond, S. J. & Cohen, F. E. (1998) Prion protein biology. *Cell* 93, 337-348.

Seetharaman, S. V., Prudencio, M., Karch, C., Holloway, S. P., Borchelt, D. R. & Hart, P. J. (2009) Immature copper-zinc superoxide dismutase and familial amyotrophic lateral sclerosis. *Experimental Biology and Medicine* 234, 1140-1154.

Seilhean, D., Cazeneuve, C., Thuries, V., Russaouen, O., Millecamps, S., Salachas, F., Meininger, V., LeGuern, E. & Duyckaerts, C. (2009) Accumulation of TDP-43 and α-actin in an amyotrophic lateral sclerosis patient with the K17I ANG mutation Acta Neuropathologica 118, 561-573.

Shibata, N., Hirano, A., Kobayashi, M., Siddique, T., Deng, H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. *Journal of Neuropathology and Experimental Neurology* 55, 481-490.

Sletten, K., Westermark, P. & Natvig, J. B. (1976) Characterization of amyloid fibril proteins from medullary carcinoma of the thyroid. *Journal of Experimental Medicine* 143, 993-998.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. Proceedings of the National Academy of Sciences, USA 95, 6469-6473.

Sreedharan, J., Blair, I. P., Tripathi, V. B., Hu, X., Vance, C., Rogelj, B., Ackerley, S., Durnall, J. C., Williams, K. L., Buratti, E., Baralle, F., de Belleroche, J., Mitchell, J. D., Leigh, P. N., A I-Chalabi, A., Miller, C. C., Nicholson, G. & Shaw, C. E. (2008) TDP-43 mutations in familial and sporadic amyotrophic lateral sclerosis. Science 319, 1668-1672.

Uemichi, T., Liuepnicks, J. J. & Benson, M. D. (1994) Hereditary renal amyloidosis with a novel variant fibrinogen. *Journal of Clinical Investigation* 93, 731-736.

van Bebber, F., Paquet, D., Hruscha, A., Schmid, B. & Haass, C. (2010) Methylene blue fails to inhibit Tau and polyglutamine protein dependent toxicity in zebrafish. *Neurobiology of Disease* 39, 265-271.

Vance, C., Rogelj, B., Hortobagyi, T., De Vos, K. J., Nishimura, A. L., Sreedharan, J., Hu, X., Smith, B., Ruddy, D., Wright, P., Ganesalingam, J., Williams, K. L., Tripathi, V., A I-Saraj, S., A I-Chalabi, A., Leigh, P. N., Blair, I. P., Nicholson, G., de Belleroche, J., Gallo, J.-M., Miller, C. C. & Shaw, C. E. (2009) Mutations in FUS, an RNA processing protein, cause familial amyotrophic lateral sclerosis type 6. Science 323, 1208-1211.

Westermark, P., Engstrom, U., Johnson, K. H., Westermark, G. T. & Betsholtz, C. (1990) Islet amyloid polypeptide: pinpointing amino acid residues linked to amyloid fibril formation. *Proceedings of the National Academy of Sciences, USA* 87, 5036-5040.

Westermark, P., Johnson, K. H. & Pitkanen, P. (1985) Systemic amyloidosis: A review with emphasis on pathogenesis. *Applied Physiology* 3, 55-68.

Westermark, P., Johnson, K. H., O'Brien, T. D. & Betsholtz, C. (1992) Islet amyloid polypeptide—a novel controversy in diabetes research. *Diabetologia* 35, 297-303.

Wijesekera, L. & Leigh, P. N. (2009) Amyotrophic lateral sclerosis. Orphanet Journal of Rare Diseases 4, 3.

Wischik, C. M., Novak, M., Thogersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences*, USA 85, 4506-4510.

Yamashita, M., Nonaka, T., Arai, T., Kametani, F., Buchman, V. L., Ninkina, N., Bachurin, S. O., Akiyama, H., Goedert, M. & Hasegawa, M. (2009) Methylene blue and dimebon inhibit aggregation of TDP-43 in cellular models. *FEBS Letters* 583, 2419-2424.

Zhang, Y.-J., Xu, Y.-F., Cook, C., Gendron, T. F., Roettges, P., Link, C. D., Lin, W.-L., Tong, J., Castanedes-Casey, M., Ash, P., Gass, J., Rangachari, V., Buratti, E., Baralle, F., Golde, T. E., Dickson, D. W. & Petrucelli, L. (2009) Aberrant cleavage of TDP-43 enhances aggregation and cellular toxicity. Proceedings of the National Academy of Sciences 106, 7607-7612.

REFERENCES FOR EXAMPLES

Gauthier, S., Feldman, H. H., Schneider, L. S., Wilcock, G. K., Frisoni, G. B., Hardlund, J. H., Moebius, H. J., Bentham, P., Kook, K. A., Wischik, D. J., Schelter, B. O., Davis, C. S., Staff, R. T., Bracoud, L., Shamsi, K., Storey, J. M. D., Harrington, C. R. & Wischik, C. M. (2016) Efficacy and safety of tau-aggregation inhibitor therapy in patients with mild or moderate Alzheimer's disease: a randomised, controlled, double-blind, parallel-arm, phase 3 trial. The Lancet 388, 2873-2884.

Wilcock, G. K., Gauthier, S., Frisoni, G. B., Jia, J., Hardlund, J. H., Moebius, H. J., Bentham, P., Kook, K. A., Schelter, B. O., Wischik, D. J., Davis, C. S., Staff, R. T., Vuksanovic, V., Ahearn, T., Bracoud, L., Shamsi, K., Marek, K., Seibyl, J., Reidel, G., Storey, J. M. D., Harrington, C. R. & Wischik, C. M. (2018) Potential of low dose leuco-methylthioninium bis(hydromethanesulphonate) (LMTM) monotherapy for treatment of mild Alzheimer's disease: cohort analysis as modified primary outcome in a phase 3 clinical trial. Journal of Alzheimer's Disease 61, 635-657.

Kipps, C. M., Nestor, P. J., Dawson, C. E., Mitchell, J., Hodges, J. R. (2008) Measuring progression in frontotemporal dementia: Implications for therapeutic interventions. Neurology 70:2046-2052.

Wagner J G. Kinetics of pharmacologic response I. Proposed relationships between response and drug concentration in the intact animal and man. *J Theor Biol.* 1968; 20(2):173-201.

The invention claimed is:

1. A method of therapeutic treatment of a neurodegenerative disorder of protein aggregation in a human subject, which method comprises orally administering to said subject a methylthioninium (MT)-containing compound,
wherein said administration provides a total daily dose of between 20.5 and 60 mg of MT to the subject per day, optionally split into 2 or more doses,
wherein the MT-containing compound is LMTM:

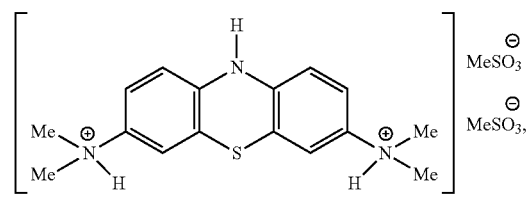

wherein said neurodegenerative disorder is behavioral-variant frontotemporal dementia (bvFTD), and
wherein the therapeutic treatment is not combined with an acetylcholinesterase inhibitor or an N-methyl-D-aspartate receptor antagonist.

2. The method as claimed in claim 1, wherein the total daily dose is between 20.5 and 40 mg.

3. The method as claimed in claim 2, wherein the total daily dose is 21 to 40 mg.

4. The method as claimed in claim 3, wherein the total daily dose is 21 to 32 mg.

5. The method as claimed in claim 3, wherein the total daily dose is or 24 to 32 mg.

6. The method as claimed in claim 2, wherein the total daily dose is about 30 mg.

7. The method as claimed in claim 1, wherein the total daily dose of the MT-containing compound is administered as a split dose twice a day or three times a day.

8. The method as claimed in claim 7, wherein the total daily dose of the MT-containing compound is administered as a split dose twice a day.

9. The method as claimed in claim 7, wherein the total daily dose of the MT-containing compound is administered as a split dose three times a day.

10. The method as claimed in claim 1, wherein the subject has not historically received treatment with an acetylcholinesterase inhibitor or an N-methyl-D-aspartate receptor antagonist.

11. The method as claimed in claim 1, wherein the treatment is part of a treatment regimen which comprises:
    (i) orally administering to said subject the MT-containing compound for a first period of time, wherein said administration provides a total daily dose of between 1 and 10 mg of MT to the subject per day;
    (ii) orally administering to said subject the MT-containing compound for a further period of time, wherein said administration provides a total daily dose of between 20.5 and 60 mg of MT to the subject per day.

12. The method as claimed in claim 11, wherein the administration of step (i) provides a total daily dose of 8 mg of MT to the subject per day.

13. The method as claimed in claim 11, wherein the administration of step (ii) provides a total daily dose of between 20.5 and 50 mg of MT to the subject per day.

14. The method as claimed in claim 13, wherein the administration of step (ii) provides a total daily dose of between 20.5 and 40 mg of MT to the subject per day.

15. The method as claimed in claim 1, wherein the MT-containing compound is administered once per day.

16. The method as claimed in claim 1, wherein the subject has historically received treatment with an acetylcholinesterase inhibitor or an N-methyl-D-aspartate receptor antagonist, but ceased that treatment at least 1, 2, 3, 4, 5, 6, 7, or 8 weeks prior to treatment with the MT-containing compound.

17. The method as claimed in claim 16, wherein the subject has historically received treatment with an acetylcholinesterase inhibitor or an N-methyl-D-aspartate receptor antagonist, but ceased that treatment at least 1, 2, 3, 4, 5, or 6 months prior to treatment with the MT-containing compound.

18. The method as claimed in claim 1, wherein the subject is selected as one who is receiving treatment with an acetylcholinesterase inhibitor or an N-methyl-D-aspartate receptor, wherein said treatment with the acetylcholinesterase inhibitor and/or N-methyl-D-aspartate receptor antagonist is discontinued prior to treatment with the MT-containing compound.

19. The method as claimed in claim 1, wherein administration provides a total daily dose of between 20.5 and 60 mg of MT to the subject per day, split into 2 or more doses.

20. The method as claimed in claim 1, wherein the MT-containing compound is administered in a powder, capsule, pill, tablet, caplet, or gelcap.

* * * * *